(12) United States Patent
Shelton, IV et al.

(10) Patent No.: US 12,046,358 B2
(45) Date of Patent: Jul. 23, 2024

(54) CONFIGURATION OF THE DISPLAY SETTINGS AND DISPLAYED INFORMATION BASED ON THE RECOGNITION OF THE USER(S) AND AWARENESS OF PROCEDURE, LOCATION OR USAGE

(71) Applicant: Cilag GmbH International, Zug (CH)

(72) Inventors: Frederick E. Shelton, IV, Hillsboro, OH (US); Taylor Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/384,553

(22) Filed: Jul. 23, 2021

(65) Prior Publication Data

US 2023/0021920 A1   Jan. 26, 2023

Related U.S. Application Data

(60) Provisional application No. 63/224,813, filed on Jul. 22, 2021.

(51) Int. Cl.
*G06F 13/40* (2006.01)
*A61B 17/00* (2006.01)
(Continued)

(52) U.S. Cl.
CPC .............. *G16H 40/20* (2018.01); *A61B 17/00* (2013.01); *A61B 18/1206* (2013.01);
(Continued)

(58) Field of Classification Search
CPC ......... G06F 3/1423; G06F 3/167; G08B 5/22; G10L 15/22; G10L 2015/223; A61B 90/37; A61B 2090/365
See application file for complete search history.

(56) References Cited

U.S. PATENT DOCUMENTS

| 6,766,373 | B1 | 7/2004 | Beadle et al. |
| 8,565,073 | B2 | 10/2013 | Rahman et al. |

(Continued)

FOREIGN PATENT DOCUMENTS

| EP | 3506287 A1 | 7/2019 |
| JP | 2017504019 A5 | 12/2017 |

(Continued)

OTHER PUBLICATIONS

Jagannath, et al., "An Analysis of Speech as a Modality for Activity Recognition during Complex Medical Teamwork", Pervasive Computing Technologies for Healthcare, May 2018, pp. 1-10.

(Continued)

*Primary Examiner* — Robert J Michaud
(74) *Attorney, Agent, or Firm* — Condo Roccia Koptiw LLP

(57) ABSTRACT

Systems, methods, and/or instrumentalities for a surgical hub configuring a display may be provided. In examples, a health care provider (HCP) and/or a medical instrument may be tracked within an operating room. In examples, a first HCP and a second HCP may be tracked within an operating room. In examples, an HCP and/or a patient may be tracked within an operating room. A surgical task that uses the medical instrument during a medical procedure may be determined.

20 Claims, 28 Drawing Sheets

(51) Int. Cl.

| | |
|---|---|
| A61B 18/12 | (2006.01) |
| A61B 34/00 | (2016.01) |
| A61B 34/10 | (2016.01) |
| A61B 34/20 | (2016.01) |
| A61B 34/30 | (2016.01) |
| A61B 34/32 | (2016.01) |
| A61B 90/00 | (2016.01) |
| G05B 13/02 | (2006.01) |
| G06F 3/14 | (2006.01) |
| G06F 3/16 | (2006.01) |
| G06F 9/48 | (2006.01) |
| G06F 9/54 | (2006.01) |
| G06F 16/21 | (2019.01) |
| G06F 16/28 | (2019.01) |
| G06N 20/00 | (2019.01) |
| G06Q 10/30 | (2023.01) |
| G06T 11/60 | (2006.01) |
| G08B 5/22 | (2006.01) |
| G10L 15/22 | (2006.01) |
| G16H 10/60 | (2018.01) |
| G16H 15/00 | (2018.01) |
| G16H 20/40 | (2018.01) |
| G16H 30/40 | (2018.01) |
| G16H 40/20 | (2018.01) |
| G16H 40/40 | (2018.01) |
| G16H 40/63 | (2018.01) |
| G16H 40/67 | (2018.01) |
| G16H 50/20 | (2018.01) |
| G16H 50/70 | (2018.01) |
| H04L 1/22 | (2006.01) |
| H04L 41/12 | (2022.01) |
| H04L 65/80 | (2022.01) |
| H04L 67/12 | (2022.01) |
| H04L 67/125 | (2022.01) |
| H04N 5/272 | (2006.01) |
| H04N 7/15 | (2006.01) |
| A61B 8/06 | (2006.01) |
| A61B 18/00 | (2006.01) |
| G06F 21/62 | (2013.01) |
| G06F 40/169 | (2020.01) |
| G16H 30/20 | (2018.01) |
| H02J 7/00 | (2006.01) |

(52) U.S. Cl.
CPC .............. *A61B 34/10* (2016.02); *A61B 34/20* (2016.02); *A61B 34/25* (2016.02); *A61B 34/30* (2016.02); *A61B 34/32* (2016.02); *A61B 90/08* (2016.02); *A61B 90/37* (2016.02); *G05B 13/0265* (2013.01); *G06F 3/14* (2013.01); *G06F 3/1423* (2013.01); *G06F 3/167* (2013.01); *G06F 9/4881* (2013.01); *G06F 9/542* (2013.01); *G06F 13/4068* (2013.01); *G06F 16/211* (2019.01); *G06F 16/284* (2019.01); *G06F 16/285* (2019.01); *G06N 20/00* (2019.01); *G06Q 10/30* (2013.01); *G06T 11/60* (2013.01); *G08B 5/22* (2013.01); *G10L 15/22* (2013.01); *G16H 10/60* (2018.01); *G16H 15/00* (2018.01); *G16H 20/40* (2018.01); *G16H 30/40* (2018.01); *G16H 40/40* (2018.01); *G16H 40/63* (2018.01); *G16H 40/67* (2018.01); *G16H 50/20* (2018.01); *G16H 50/70* (2018.01); *H04L 1/22* (2013.01); *H04L 41/12* (2013.01); *H04L 65/80* (2013.01); *H04L 67/12* (2013.01); *H04L 67/125* (2013.01); *H04N 5/272* (2013.01); *H04N 7/15* (2013.01); *A61B 8/06* (2013.01); *A61B 2017/00221* (2013.01); *A61B 2018/00702* (2013.01); *A61B 2018/00994* (2013.01); *A61B 2034/2072* (2016.02); *A61B 2034/254* (2016.02); *A61B 2090/364* (2016.02); *A61B 2090/365* (2016.02); *A61B 2090/373* (2016.02); *G06F 21/6245* (2013.01); *G06F 40/169* (2020.01); *G10L 2015/223* (2013.01); *G16H 30/20* (2018.01); *H02J 7/0063* (2013.01)

(56) References Cited

U.S. PATENT DOCUMENTS

| | | | |
|---|---|---|---|
| 8,908,678 | B1 | 12/2014 | Mcgonigal et al. |
| 9,011,427 | B2 | 4/2015 | Price et al. |
| 9,283,054 | B2 | 3/2016 | Morgan et al. |
| 9,345,481 | B2 | 5/2016 | Hall et al. |
| 11,146,690 | B2 | 10/2021 | Minert |
| 2002/0000464 | A1 | 1/2002 | Ramberg et al. |
| 2005/0210070 | A1 | 9/2005 | Macneil |
| 2008/0030345 | A1 | 2/2008 | Austin et al. |
| 2013/0051220 | A1 | 2/2013 | Ryshakov |
| 2013/0149967 | A1 | 6/2013 | Ma et al. |
| 2014/0160259 | A1 | 6/2014 | Blanquart et al. |
| 2014/0160260 | A1 | 6/2014 | Blanquart et al. |
| 2014/0263552 | A1 | 9/2014 | Hall et al. |
| 2014/0267655 | A1 | 9/2014 | Richardson et al. |
| 2015/0119035 | A1 | 4/2015 | Ganu et al. |
| 2015/0128274 | A1 | 5/2015 | Giokas |
| 2015/0182118 | A1 | 7/2015 | Bradbury et al. |
| 2015/0215159 | A1 | 7/2015 | Liao et al. |
| 2017/0296213 | A1 | 10/2017 | Swensgard et al. |
| 2018/0344308 | A1 | 12/2018 | Nawana et al. |
| 2018/0360452 | A1 | 12/2018 | Shelton, IV et al. |
| 2019/0019163 | A1 | 6/2019 | Kuhn et al. |
| 2019/0191963 | A1 | 6/2019 | Kuhn et al. |
| 2019/0200844 | A1 | 7/2019 | Shelton, IV et al. |
| 2019/0200906 | A1 | 7/2019 | Shelton, IV et al. |
| 2019/0200980 | A1 | 7/2019 | Shelton, IV et al. |
| 2019/0200988 | A1 | 7/2019 | Shelton, IV |
| 2019/0201033 | A1 | 7/2019 | Yates et al. |
| 2019/0201102 | A1 | 7/2019 | Shelton, IV et al. |
| 2019/0201104 | A1 | 7/2019 | Shelton, IV et al. |
| 2019/0201115 | A1 | 7/2019 | Shelton, IV et al. |
| 2019/0201123 | A1 | 7/2019 | Shelton, IV et al. |
| 2019/0201124 | A1 | 7/2019 | Shelton, IV et al. |
| 2019/0201125 | A1 | 7/2019 | Shelton, IV et al. |
| 2019/0201126 | A1 | 7/2019 | Shelton, IV et al. |
| 2019/0201127 | A1 | 7/2019 | Shelton, IV et al. |
| 2019/0201129 | A1 | 7/2019 | Shelton, IV et al. |
| 2019/0201137 | A1 | 7/2019 | Shelton, IV et al. |
| 2019/0201140 | A1 | 7/2019 | Yates et al. |
| 2019/0204201 | A1 | 7/2019 | Shelton, IV et al. |
| 2019/0205441 | A1 | 7/2019 | Shelton, IV et al. |
| 2019/0205566 | A1 | 7/2019 | Shelton, IV et al. |
| 2019/0205567 | A1 | 7/2019 | Shelton, IV et al. |
| 2019/0206216 | A1 | 7/2019 | Shelton, IV et al. |
| 2019/0206542 | A1 | 7/2019 | Shelton, IV et al. |
| 2019/0206551 | A1 | 7/2019 | Yates et al. |
| 2019/0206556 | A1 | 7/2019 | Shelton, IV et al. |
| 2019/0206562 | A1 | 7/2019 | Shelton, IV et al. |
| 2019/0206569 | A1 | 7/2019 | Shelton, IV et al. |
| 2019/0206576 | A1 | 7/2019 | Shelton, IV et al. |
| 2019/0207773 | A1 | 7/2019 | Shelton, IV et al. |
| 2019/0207911 | A1 | 7/2019 | Wiener et al. |
| 2019/0333626 | A1 | 10/2019 | Mansi et al. |
| 2020/0244734 | A1 | 7/2020 | Mendiola et al. |
| 2020/0405403 | A1 | 12/2020 | Shelton, IV et al. |
| 2021/0205031 | A1 | 7/2021 | Shelton, IV |
| 2021/0212717 | A1 | 7/2021 | Yates et al. |
| 2021/0236227 | A1 | 8/2021 | Kumar et al. |
| 2021/0290046 | A1 | 9/2021 | Nazareth et al. |
| 2022/0046292 | A1 | 2/2022 | Nair et al. |
| 2022/0079675 | A1 | 3/2022 | Lang |
| 2022/0104713 | A1 | 4/2022 | Shelton, IV |

(56) References Cited

U.S. PATENT DOCUMENTS

| | | |
|---|---|---|
| 2022/0104807 A1* | 4/2022 | Shelton, IV ..... A61B 17/07207 |
| 2022/0104896 A1 | 4/2022 | Shelton, IV et al. |
| 2022/0104910 A1* | 4/2022 | Shelton, IV ......... A61B 90/361 |
| 2022/0108789 A1 | 4/2022 | Shelton, IV et al. |
| 2022/0202508 A1 | 6/2022 | Hiranandani et al. |
| 2022/0233119 A1 | 7/2022 | Shelton, IV et al. |
| 2022/0233135 A1 | 7/2022 | Shelton, IV et al. |
| 2022/0233136 A1 | 7/2022 | Shelton, IV et al. |
| 2022/0233151 A1 | 7/2022 | Shelton, IV et al. |
| 2022/0233191 A1 | 7/2022 | Shelton, IV et al. |
| 2022/0233252 A1 | 7/2022 | Shelton, IV et al. |
| 2022/0233254 A1 | 7/2022 | Shelton, IV et al. |
| 2022/0238216 A1 | 7/2022 | Shelton, IV et al. |
| 2022/0240869 A1 | 8/2022 | Shelton, IV et al. |
| 2022/0241028 A1 | 8/2022 | Shelton, IV et al. |
| 2022/0241474 A1 | 8/2022 | Shelton, IV et al. |
| 2022/0265357 A1 | 8/2022 | Morvan et al. |
| 2022/0303945 A1 | 9/2022 | Tsuda |
| 2023/0021832 A1 | 1/2023 | Shelton, IV et al. |
| 2023/0022604 A1 | 1/2023 | Shelton, IV |
| 2023/0023083 A1 | 1/2023 | Shelton, IV et al. |
| 2023/0023635 A1 | 1/2023 | Shelton, IV et al. |
| 2023/0025061 A1 | 1/2023 | Shelton, IV et al. |
| 2023/0025790 A1 | 1/2023 | Shelton, IV et al. |
| 2023/0025827 A1 | 1/2023 | Shelton, IV et al. |
| 2023/0026634 A1 | 1/2023 | Shelton, IV et al. |
| 2023/0026893 A1 | 1/2023 | Shelton, IV et al. |
| 2023/0027210 A1 | 1/2023 | Shelton, IV et al. |
| 2023/0027543 A1 | 1/2023 | Shelton, IV et al. |
| 2023/0028059 A1 | 1/2023 | Shelton, IV et al. |
| 2023/0028633 A1 | 1/2023 | Shelton, IV et al. |
| 2023/0028677 A1 | 1/2023 | Shelton, IV et al. |
| 2023/0035775 A1 | 2/2023 | Kohada |

FOREIGN PATENT DOCUMENTS

| | | |
|---|---|---|
| WO | 2013174327 A1 | 11/2013 |
| WO | 2017089479 A1 | 6/2017 |
| WO | 2019119130 A1 | 6/2019 |
| WO | 2021048326 A1 | 3/2021 |

OTHER PUBLICATIONS

JP 2017-504019 A5, Non-final office action for related U.S. Appl. No. 17/384,265. Translation included.

WO 2013174327 A1, US2015215159 A1.

Hutchins, Andrew R., "Machine Learning Applications for Objectively Assessing Surgical Skill and Instrument Dynamics", Department of Mechanical Engineering & Materials Science, Duke University; Available from ProQuest Dissertations and Theses Professional, 2019, 151 pages.

* cited by examiner

CONFIGURATION OF THE DISPLAY SETTINGS AND DISPLAYED INFORMATION BASED ON THE RECOGNITION OF THE USER(S) AND AWARENESS OF PROCEDURE, LOCATION OR USAGE

CROSS-REFERENCE TO RELATED APPLICATIONS

This application claims the benefit of Provisional U.S. Patent Application No. 63/224,813, filed Jul. 22, 2021, the disclosure of which is incorporated herein by reference in its entirety.

This application is related to the following, filed contemporaneously, the contents of each of which are incorporated by reference herein:
U.S. patent application Ser. No. 17/384,274, filed Jul. 23, 2021, titled METHOD OF SURGICAL SYSTEM POWER MANAGEMENT, COMMUNICATION, PROCESSING, STORAGE AND DISPLAY
U.S. patent application Ser. No. 17/384,508, filed Jul. 23, 2021, titled HUB IDENTIFICATION AND TRACKING OF OBJECTS AND PERSONNEL WITHIN THE OR TO OVERLAY DATA THAT IS CUSTOM TO THE USER'S NEED

BACKGROUND

Surgical procedures are typically performed in surgical operating theaters or rooms in a healthcare facility such as, for example, a hospital. Various surgical devices and systems are utilized in performance of a surgical procedure. In the digital and information age, medical systems and facilities are often slower to implement systems or procedures utilizing newer and improved technologies due to patient safety and a general desire for maintaining traditional practices.

SUMMARY

Systems, methods, and/or instrumentalities for a surgical hub configuring a display may be provided. In examples, a health care provider (HCP) and/or a medical instrument may be tracked within an operating room. In examples, a first HCP and a second HCP may be tracked within an operating room. In examples, an HCP and/or a patient may be tracked within an operating room. A surgical task that uses the medical instrument during a medical procedure may be determined.

A display configuration for the display may be determined, for example, based on the surgical task and/or an interaction between the HCP and the medical instrument. In examples, a first display configuration may be determined based on a first interaction between the HCP and the medical instrument. For example, a second interaction may be determined between the HCP and the medical instrument, the HCP and the display, and/or the HCP and the patient. The display configuration may be modified based on the second interaction. The display configuration for the display may be determined based on the surgical task and an interaction between a first HCP and a second HCP. For example, the interaction between the first HCP and the second HCP may be a verbal communication. The verbal communication may be determined to be a request from the first HCP for assistance from the second HCP in performing the surgical task. The display configuration may be modified such that the display configuration may configure the display with one or more preferences that are relevant to the second HCP.

Systems, methods, and/or instrumentalities for a surgical hub providing a health care provider (HCP) with a data overlay may be provided. A state of a surgical object and/or an area of the operating room where the surgical object is located may be determined. Determining an area of the operating room where the surgical object is located may comprise using a sensor data associated with the area, a wearable device data, sensor data associated with the HCP, an image from a camera within the operating room, an ultrasonic sensor, a laser sensor, a laser doppler sensor, a radio frequency sensor, and/or a video form the camera within the operating room. A time associated with the surgical object and/or the area of the operating room may be determined. The state of the surgical object may be determined to indicate that the surgical object is ready for use in the surgical task.

A surgical task that uses the surgical object during a medical procedure may be determined. The surgical object entering the area of the operating room during the task and/or medical procedure may be determined. In examples, determining that the surgical object has entered the operating room may be based on the area of the operating where the surgical object is located. The time may indicate when the surgical object entered the operating room. In examples, it may be determined that the surgical object has left the area of the operating room. The time may indicate when the surgical object has left the area.

BRIEF DESCRIPTION OF THE DRAWINGS

FIG. 25 depicts a method that may be performed by a surgical hub for providing adaptations and/or controls that may change based on spatial awareness of objects and personnel within the surgical OR.

DETAILED DESCRIPTION

Applicant of the present application owns the following U.S. patent applications, each of which is herein incorporated by reference in its entirety:

U.S. Patent. Application Publication No. 2019-0201104 A1 (U.S. patent application Ser. No. 15/940,671), titled SURGICAL HUB SPATIAL AWARENESS TO DETERMINE DEVICES IN OPERATING THEATER, filed Mar. 29, 2018

U.S. Pat. No. 9,283,054 (U.S. patent application Ser. No. 13/974,208), titled SURGICAL APPARATUS WITH INDICATOR, which issued on Mar. 15, 2016

U.S. Pat. No. 9,011,427 (U.S. patent application Ser. No. 13/276,687), titled SURGICAL INSTRUMENT WITH SAFETY GLASSES, which issued on Apr. 21, 2015

U.S. Patent Application Publication 2019-0201140 A1 (U.S. patent application Ser. No. 15/940,654), entitled SURGICAL HUB SITUATIONAL AWARENESS, filed Mar. 29, 2018; and U.S. Patent. Application Publication No. 2019-0201129 A1 (U.S. patent application Ser. No. 16/182,269), titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018.

Figure 1A:
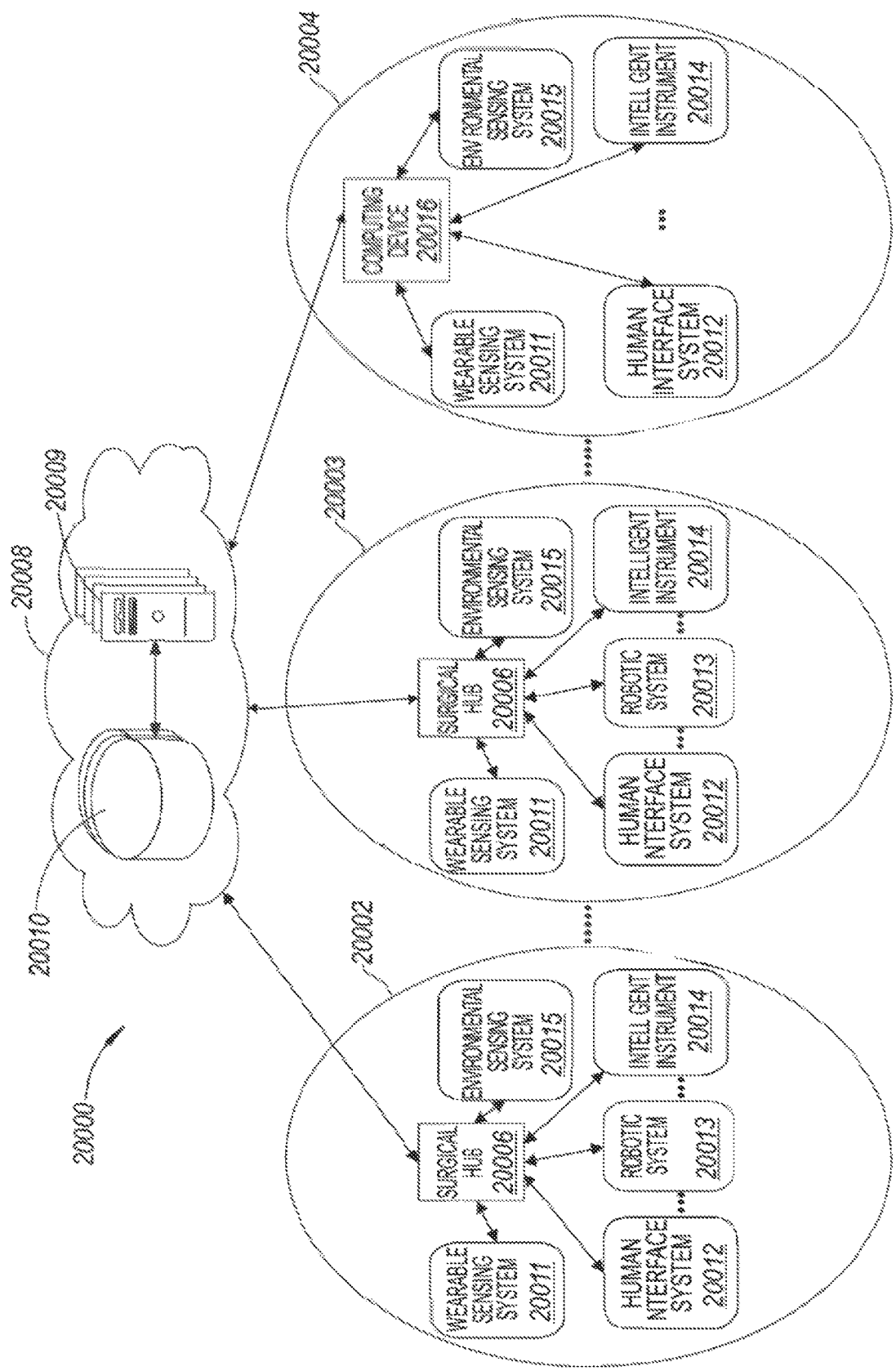
FIG. 1A is a block diagram of a computer-implemented surgical system.

FIG. 1A is a block diagram of a computer-implemented surgical system 20000. An example surgical system such as the surgical system 20000 may include one or more surgical systems (e.g., surgical sub-systems) 20002, 20003 and 20004. For example, surgical system 20002 may include a computer-implemented interactive surgical system. For example, surgical system 20002 may include a surgical hub 20006 and/or a computing device 20016 in communication with a cloud computing system 20008, for example, as described in FIG. 2. The cloud computing system 20008 may include at least one remote cloud server 20009 and at least one remote cloud storage unit 20010. Example surgical systems 20002, 20003, or 20004 may include a wearable sensing system 20011, an environmental sensing system 20015, a robotic system 20013, one or more intelligent instruments 20014, human interface system 20012, etc. The human interface system is also referred herein as the human interface device. The wearable sensing system 20011 may include one or more HCP sensing systems, and/or one or more patient sensing systems. The environmental sensing system 20015 may include one or more devices, for example, used for measuring one or more environmental attributes, for example, as further described in FIG. 2. The robotic system 20013 may include a plurality of devices used for performing a surgical procedure, for example, as further described in FIG. 2.

The surgical system 20002 may be in communication with a remote server 20009 that may be part of a cloud computing system 20008. In an example, the surgical system 20002 may be in communication with a remote server 20009 via an internet service provider's cable/FIOS networking node. In an example, a patient sensing system may be in direct communication with a remote server 20009. The surgical system 20002 and/or a component therein may communicate with the remote servers 20009 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

A surgical hub 20006 may have cooperative interactions with one of more means of displaying the image from the laparoscopic scope and information from one or more other smart devices and one or more sensing systems 20011. The surgical hub 20006 may interact with one or more sensing systems 20011, one or more smart devices, and multiple displays. The surgical hub 20006 may be configured to gather measurement data from the one or more sensing systems 20011 and send notifications or control messages to the one or more sensing systems 20011. The surgical hub 20006 may send and/or receive information including notification information to and/or from the human interface system 20012. The human interface system 20012 may include one or more human interface devices (HIDs). The surgical hub 20006 may send and/or receive notification information or control information to audio, display and/or control information to various devices that are in communication with the surgical hub.

For example, the sensing systems 20001 may include the wearable sensing system 20011 (which may include one or more HCP sensing systems and one or more patient sensing systems) and the environmental sensing system 20015 as discussed in FIG. 1A. The one or more sensing systems 20001 may measure data relating to various biomarkers. The one or more sensing systems 20001 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 20001 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 20000, for example. The information from the biomarkers may be determined and/or used by the computer-implemented patient and the surgical system 20000 to improve said systems and/or to improve patient outcomes, for example. The one or more sensing systems 20001, biomarkers 20005, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

Figure 1B:
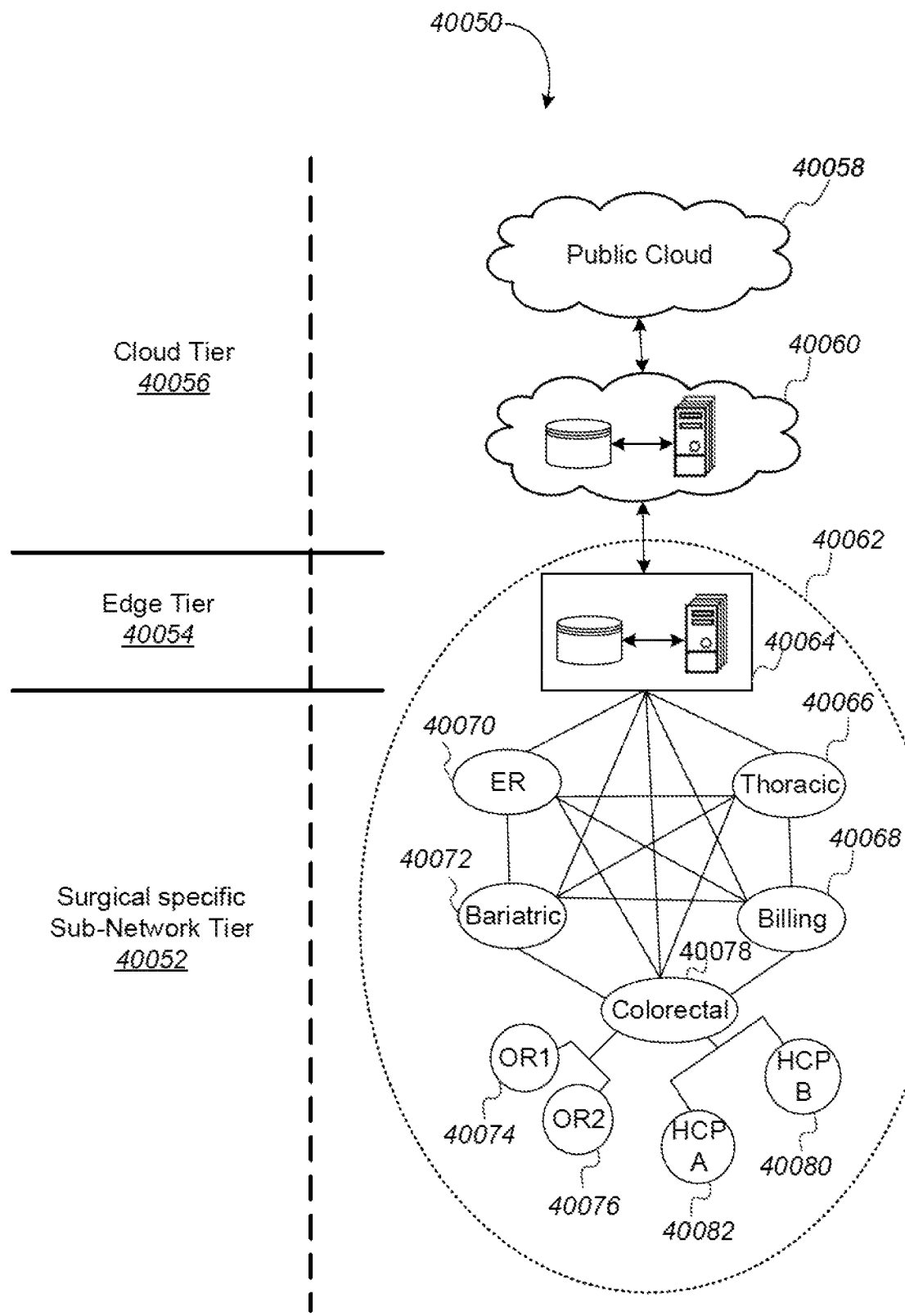
FIG. 1B is a block diagram of a computer-implemented multi-tier surgical system.

FIG. 1B is a block diagram of a computer-implemented multi-tier surgical system. As illustrated in FIG. 1B, a computer-implemented multi-tier surgical system 40050 may include multiple tiers of systems, such as a surgical specific sub-network tier system 40052, an edge tier system 40054 that is associated with the surgical specific sub-network tier system 40052, and a cloud tier system 40056.

A surgical specific sub-network tier system 40052 may include a plurality of interconnected surgical sub-systems. For example, the surgical sub-systems may be grouped by the type of surgical procedures and/or other departments in a medical facility or a hospital. For example, a medical facility or a hospital may include a plurality of surgical procedure specific departments, such as an emergency room (ER) department 40070, colorectal department 40078, bariatric department 40072, thoracic department 40066, and billing department 40068. Each of the surgical procedure specific departments may include one or more surgical sub-systems associated with an operating room (OR) and/or a healthcare care professional (HCP). For example, the colorectal department 40078 may include a set of surgical hubs (e.g., surgical hub 20006 as described in FIG. 1A). The surgical hubs may be designated for a respective HCP, such as HCP A, 40082 and HCP B, 40080. In an example, the colorectal department may include a group of surgical hubs that may be located in respective ORs, such as OR 1, 40074 and OR 2, 40076. The medical facility or the hospital may also include a billing department subsystem 40068. The billing department subsystem 40068 may store and/or manage billing data associated with a respective department, such as the ER department 40070, colorectal department 40078, bariatric department 40072, and/or thoracic department 40066.

An edge tier system 40054 may be associated with a medical facility or a hospital and may include one or more edge computing systems 40064, for example. An edge computing system 40064 may include a storage sub-system and a server sub-system. In an example, the edge computing system comprising an edge server and/or a storage unit may provide additional processing and/or storage services to a surgical hub that is part of one of the departmental ORs (e.g., OR1 and OR2 of the colorectal department).

The surgical specific sub-network tier system 40052 and the edge tier system 40054 may be located within a Health Insurance Portability and Accountability Act (HIPAA) boundary 40062. The surgical specific sub-network system 40052 and the edge tier system 40054 may be connected to the same local data network. The local data network may be a local data network of a medical facility or a hospital. The local data network may be within the HIPAA boundary. Because the surgical specific sub-network tier system 40052 and the edge tier system 40054 are located within the HIPAA boundary 40062, patient data between an edge computing system 40064 and a device located within one of the entities of the surgical specific sub-network tier system 40052 may flow without redaction and/or encryption. For example, patient data between an edge computing system 40064 and a surgical hub located in OR1 40074 of the colorectal department 40078 may flow without redaction and/or encryption.

The cloud tier system 40056 may include an enterprise cloud system 40060 and a public cloud system 40058. For example, the enterprise cloud system 40060 may be a cloud computing system 20008 that includes a remote cloud server sub-system and/or a remote cloud storage subsystem, as described in FIG. 1A. The enterprise cloud system 40060 may be managed by an organization, such as a private company. The enterprise cloud system 40060 may be in communication with one or more entities (e.g., edge computing systems 40064, surgical hubs located in ORs (e.g., OR1 40074) of the various departments (e.g., colorectal department 40078)) that are located within the HIPAA boundary 40062.

The public cloud system 40058 may be operated by a cloud computing service provider. For example, the cloud computing service provider may provide storage services and/or computing services to a plurality of enterprise cloud systems (e.g., enterprise cloud system 40060).

Figure 1C:
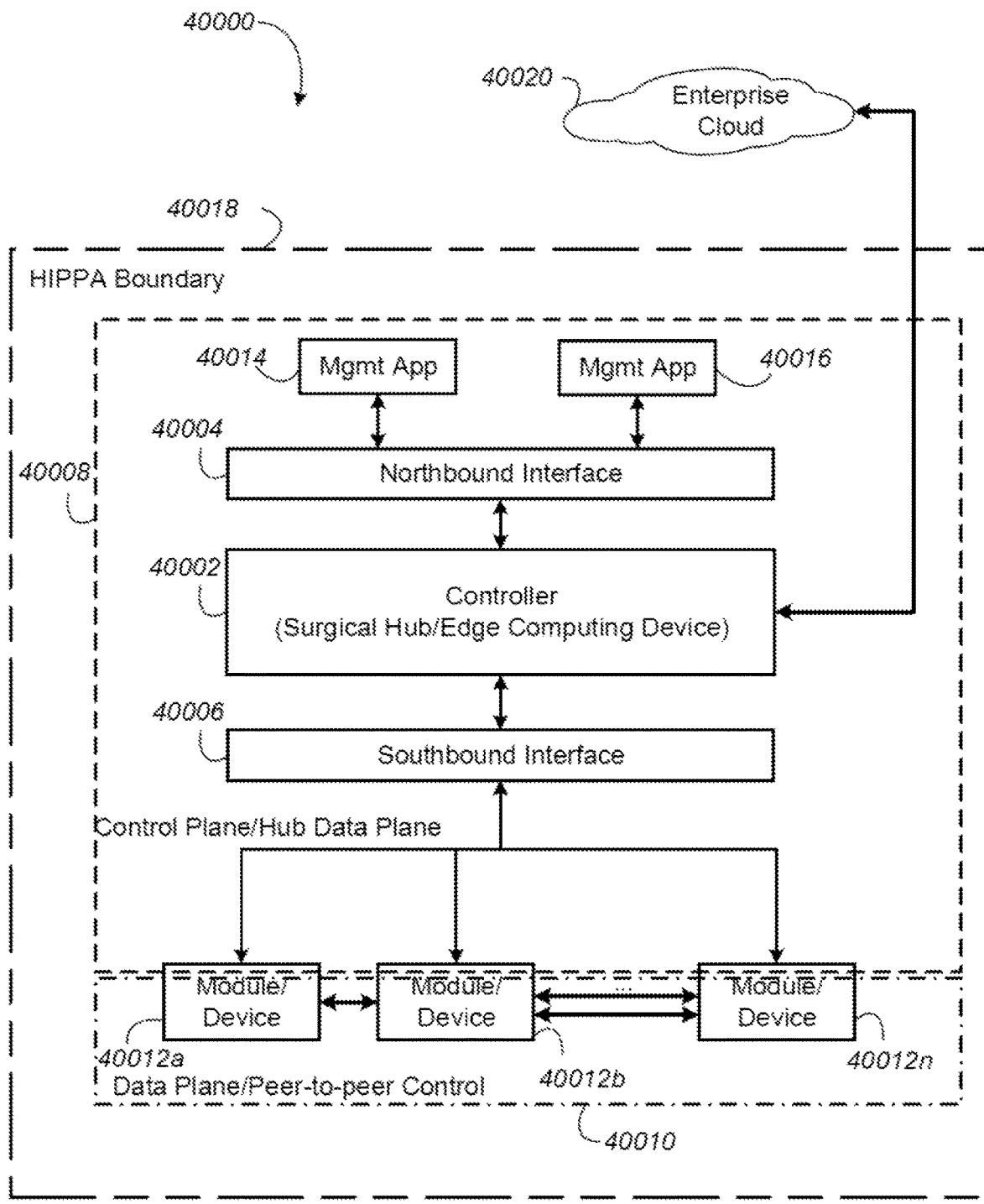
FIG. 1C is a logical diagram illustrating control plane and data plane of a surgical system.

FIG. 1C is a logical block diagram 40000 illustrating various communication planes in a surgical system. As illustrated in FIG. 1C, the communication planes between a controller 40002 and management applications 40014 and 40016 on one side and, the system modules and/or modular devices 40012*a* through 40012*n* on the other side, may use control plane 40008 and data plane 40010. In an example, in addition to the control plane 40008, a data plane may also exist between the system modules and/or modular devices 40012*a* through 40012*n* and the surgical hub. The data plane 40010 may provide data plane paths (e.g., redundant data plane paths) between the system modules and/or the modular devices 40012*a* through 40012*n* that are associated with one or more surgical hubs. A surgical hub or one of the surgical hubs (e.g., in case of a plurality of surgical hubs present in an operating room) may act as a controller 40002. In an example, the controller 40002 may be an edge computing system that may reside within a Health Insurance Portability and Accountability Act (HIPAA) boundary where the surgical system is located, for example, as illustrated in FIG. 1B. The controller 40002 may be in communication with an enterprise cloud system 40020. As illustrated in FIG. 1C, the enterprise cloud system 40020 may be located outside the HIPAA boundary 40018. Accordingly, the patient data flowing to and/or from the enterprise cloud system 40020 may be redacted and/or encrypted.

The controller 40002 may be configured to provide a northbound interface 40004 and a southbound interface 40006. The northbound interface 40004 may be used for providing a control plane 40008. The control plane 40008 may include one or more management applications 40014 and 40016 that may enable a user to configure and/or manage system modules and/or modular devices modular devices 40012*a* through 40012*n* associated with a surgical system. The management applications 40014 and 40016 may be used to obtain status of various system modules and/or the modular devices 40012*a* through 40012*n*.

The management applications 40014 and 40016 using the control plane may interact with the controller 40002, for example, using a set of application programming interface (API) calls. The management applications 40014 and 40016 may interact with the controller 40002 via a management protocol or an application layer protocol to configure and/or monitor the status of a system module and/or a modular device. The management protocols or the application layer protocols used to monitor the status and/or configure a system module or a modular device associated with a surgical system may include the simple network management protocol (SNMP), TELNET protocol, secure shell (SSH) protocol, network configuration protocol (NETCONF), etc.

SNMP or a similar protocol may be used to collect status information and/or send configuration related data (e.g., configuration related control programs) associated with system modules and/or modular devices to the controller. SNMP or a similar protocol may collect information by selecting devices associated with a surgical system from a central network management console using messages (e.g., SNMP messages). The messages may be sent and/or received at fixed or random intervals. The messages may include Get messages and Set messages. The Get messages or messages similar to the Get messages may be used for obtaining information from a system module or a modular device associated with a surgical system. The Set message or messages similar to the Set message may be used for changing a configuration associated with a system module or a modular device associated with a surgical system.

For example, the Get messages or similar messages may include the SNMP messages GetRequest, GetNextRequest, or GetBulkRequest. The Set messages may include SNMP SetRequest message. The GetRequest, GetNextRequest, GetBulkRequest messages or similar messages may be used by a configuration manager (e.g., an SNMP manager) running on the controller 40002. The configuration manager may be in communication with a communication agent (e.g., an SNMP agent) that may be a part of a system module and/or a modular device in a surgical system. The SNMP message SetRequest message or similar may be used by the communication manager on the controller 40002 to set the value of a parameter or an object instance in the communication agent on a system module and/or a modular device of a surgical system. In an example, SNMP modules, for example, may be used to establish communication path between system modules and/or modular devices associated with a surgical system.

Based on the query or configuration related messages received from a management application, such as management applications 40014 and 40016, the controller 40002 may generate configuration queries and/or configuration data for querying or configuring the system modules and/or the modular devices associated with the surgical hub or the surgical system. A surgical hub (e.g., the surgical hub 20006 shown in FIG. 1A) or an edge computing system (e.g., the edge computing system 40064 shown in FIG. 1B) may manage and/or control various system modules and/or modular devices 40012*a* through 40012*n* associated with a surgical system. For example, the northbound interface 40004 of the controller 40002 may be used for changing control interactions between one or more modules associated and/or devices associated with a surgical system. In an example, the controller 40002 may be used for establishing one or more communication data paths between a plurality of modules and/or devices associated with a surgical system. The controller 40002 may use its southbound interface 40006 to send the control programs comprising queries and/or configuration changes to the system modules and/or the modular devices of the surgical system.

The system modules and/or the modular devices 40012*a* through 40012*n* of a surgical system, or the communication agents that may be a part of the system modules and/or the modular devices, may send notification messages or traps to the controller 40002. The controller may forward the notification messages or traps via its northbound interface 40004 to the management application 40014 and 40016 for displaying on a display. In an example, the controller 40002 may send the notification to other system modules and/or modular devices 40012*a* through 40012*n* that are part of the surgical system.

The system modules and/or the modular devices 40012*a* through 40012*n* of a surgical system or the communication agents that are part of the system modules and/or the modular devices may send responses to the queries received from the controller 40002. For example, a communication agent that may be part of a system module or a modular device may send a response message in response to a Get or a Set message or messages similar to the Get or the Set messages received from the controller 40002. In an example, in response to a Get message or a similar message received from the controller 40002, the response message from the system module or the modular device 40012*a* through 40012*n* may include the data requested. In an example, in response to a Set message or a similar message received from a system module or a modular device 40012*a* through 40012*n*, the response message from the controller 40002 may include the newly set value as confirmation that the value has been set.

A trap or a notification message or a message similar to the trap or the notification message may be used by a system module or a modular device 40012*a* through 40012*n* to provide information about events associated with the system modules or the modular devices. For example, a trap or a notification message may be sent from a system module or a modular device 40012*a* through 40012*n* to the controller 40002 indicating a status of a communication interface (e.g., whether it available or unavailable for communication). The controller 40002 may send a receipt of the trap message back to the system module or the modular device 40012*a* through 40012*n* (e.g., to the agent on the system module or a modular device).

In an example, TELNET protocol may be used to provide a bidirectional interactive text-oriented communication facility between system modules and/or modular devices 40012*a* through 40012*n* and the controller 40002 TELNET protocol may be used to collect status information and/or send configuration data (e.g., control programs) from/to the controller 40002. TELNET may be used by one of the management applications 40014 or 40016 to establish a connection with the controller 40002 using the transmission control protocol port number 23.

In an example, SSH, a cryptographic encrypted protocol, may be used to allow remote login and to collect status information and/or send configuration data about system modules and/or modular devices 40012*a* through 40012*n* from/to the controller 40002. SSH may be used by one of the management applications 40014 or 40016 to establish an encrypted connection with the controller 40002 using the transmission control protocol port number 22.

In an example, NETCONF may be used to perform management functions by invoking remote procedure calls using, for example, <rpc>, <rpc-reply>, or <edit-config> operations. The <rpc> and <rpc-reply> procedure calls or similar procedure calls may be used for exchanging information from a system module and/or a modular device associated with a surgical system. The NETCONF <edit-config> operation or a similar operation may be used for configuring the system modules and/or the modular devices associated with the surgical system.

The controller 40002 may configure the system modules and/or modular device 40012*a* through 40012*n* to establish a data plane 40010. The data plane 40010 (e.g., also referred to as a user plane or a forwarding plane) may enable a communication data path between a plurality of system modules and/or modular device 40012*a* through 40012*n*. The data plane 40010 may be utilized by the system modules and/or the modular device 40012*a* through 40012*n* for communicating data flows of data between the system modules and/or modular devices associated with a surgical system. The data flows may be established using one or more dedicated communication interfaces between the system modules and/or the modular devices associated with one or more surgical hubs of a surgical system. In an example, the data flows may be established over one or more local area networks (LANs) and one or more wide area networks (WANs), such as the Internet.

In an example, the data plane 40010 may provide support for establishing a first and a second independent, disjointed, concurrent, and redundant communication path for data flow between the system modules and/or modular devices 40012*b* and 40012*n*. As illustrated in FIG. 1C. redundant communication paths may be established between system modules/modular devices 40012*b* and 40012*n*. The redundant communication paths may carry same/redundant data flows between the system modules and/or modular devices. In an example, when or if some of the data packets are dropped on one of the redundant communication paths due to problems with one of the communication interfaces on the system modules/modular devices 40012*b* and 40012*n*, the system modules and/or the modular devices may continue to send/receive at least one copy of the dropped data packets over the second communication path.

Figure 2:
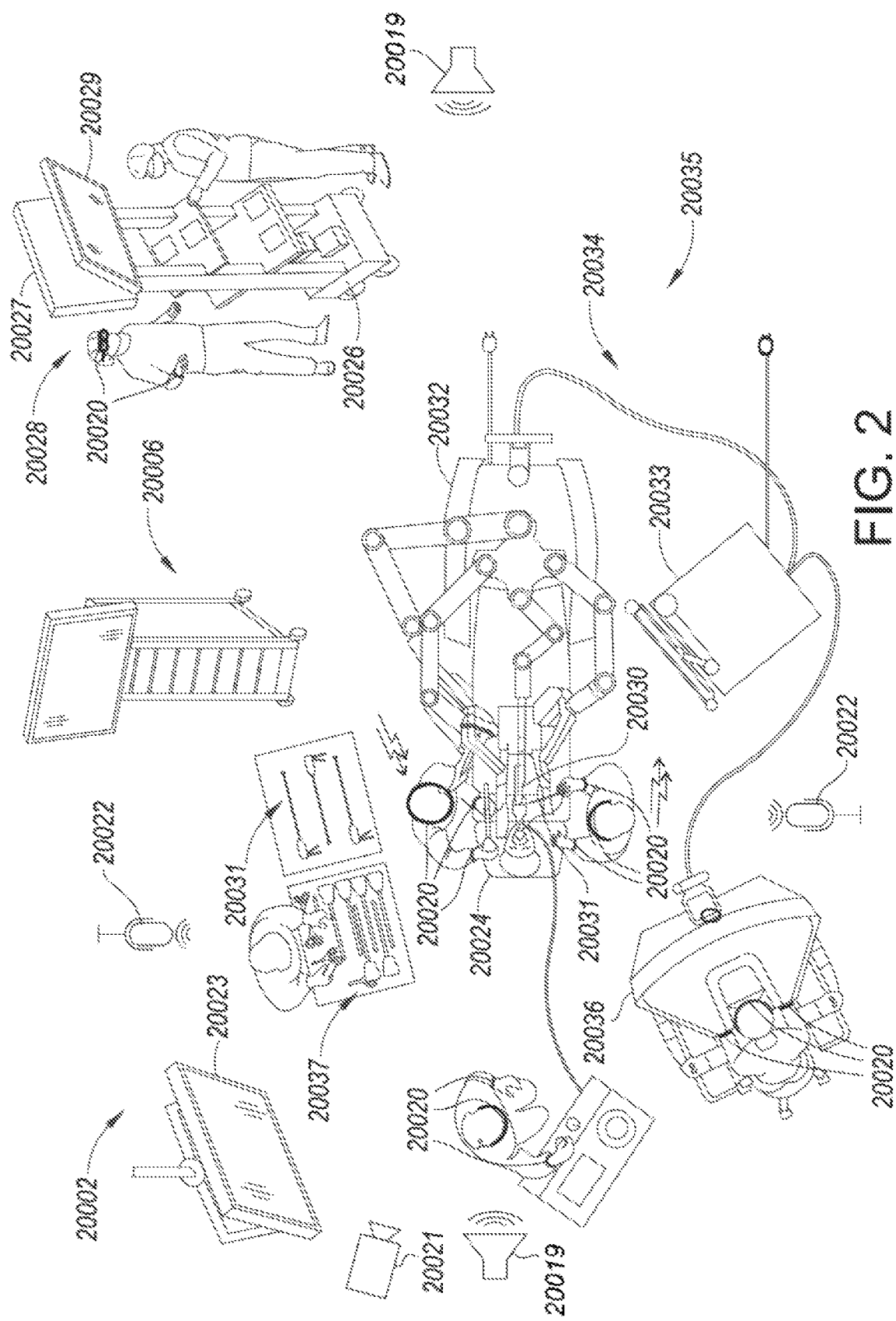
FIG. 2 shows an example surgical system in a surgical operating room.

FIG. 2 shows an example of a surgical system 20002 in a surgical operating room. As illustrated in FIG. 2, a patient is being operated on by one or more health care professionals (HCPs). The HCPs are being monitored by one or more HCP sensing systems 20020 worn by the HCPs. The HCPs and the environment surrounding the HCPs may also be monitored by one or more environmental sensing systems including, for example, a set of cameras 20021, a set of microphones 20022, and other sensors that may be deployed in the operating room. The HCP sensing systems 20020 and the environmental sensing systems may be in communication with a surgical hub 20006, which in turn may be in communication with one or more cloud servers 20009 of the cloud computing system 20008, as shown in FIG. 1A. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 20023 and one or more audio output devices (e.g., speakers 20019) are positioned in the sterile field to be visible to an operator at the operating table 20024. In addition, a visualization/notification tower 20026 is positioned outside the sterile field. The visualization/notification tower 20026 may include a first non-sterile human interactive device (HID) 20027 and a second non-sterile HID 20029, which may face away from each other. The HID may be a display or a display with a touchscreen allowing a human to interface directly with the HID. A human interface system, guided by the surgical hub 20006, may be configured to utilize the HIDs 20027, 20029, and 20023 to coordinate information flow to operators inside and outside the sterile field. In an example, the surgical hub 20006 may cause an HID (e.g., the primary HID 20023) to display a notification and/or information about the patient and/or a surgical procedure step. In an example, the surgical hub 20006 may prompt for and/or receive input from personnel in the sterile field or in the non-sterile area. In an example, the surgical hub 20006 may cause an HID to display a snapshot of a surgical site, as recorded by an imaging device 20030, on a non-sterile HID 20027 or 20029, while maintaining a live feed of the surgical site on the primary HID 20023. The snapshot on the non-sterile display 20027 or 20029 can permit a non-sterile operator to perform a diagnostic step relevant to the surgical procedure, for example.

In one aspect, the surgical hub 20006 may be configured to route a diagnostic input or feedback entered by a non-sterile operator at the visualization tower 20026 to the primary display 20023 within the sterile field, where it can be viewed by a sterile operator at the operating table. In one example, the input can be in the form of a modification to the snapshot displayed on the non-sterile display 20027 or 20029, which can be routed to the primary display 20023 by the surgical hub 20006.

Referring to FIG. 2, a surgical instrument 20031 is being used in the surgical procedure as part of the surgical system 20002. The hub 20006 may be configured to coordinate information flow to a display of the surgical instrument 20031. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 20026 can be routed by the hub 20006 to the surgical instrument display within the sterile field, where it can be viewed by the operator of the surgical instrument 20031. Example surgical instruments that are suitable for use with the surgical system 20002 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 20002 being used to perform a surgical procedure on a patient who is lying down on an operating table 20024 in a surgical operating room 20035. A robotic system 20034 may be used in the surgical procedure as a part of the surgical system 20002. The robotic system 20034 may include a surgeon's console 20036, a patient side cart 20032 (surgical robot), and a surgical robotic hub 20033. The patient side cart 20032 can manipulate at least one removably coupled surgical tool 20037 through a minimally invasive incision in the body of the patient while the surgeon views the surgical site through the surgeon's console 20036. An image of the surgical site can be obtained by a medical imaging device 20030, which can be manipulated by the patient side cart 20032 to orient the imaging device 20030. The robotic hub 20033 can be used to process the images of the surgical site for subsequent display to the surgeon through the surgeon's console 20036.

Other types of robotic systems can be readily adapted for use with the surgical system 20002. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 20008, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 20030 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 20030 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 20030 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 20030 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 20011 illustrated in FIG. 1A may include one or more sensing systems, for example, HCP sensing systems 20020 as shown in FIG. 2. The HCP sensing systems 20020 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 20020 may measure a set of biomarkers to monitor the heart rate of an HCP. In an example, a sensing system 20020 worn on a surgeon's wrist (e.g., a watch or a wristband) may use an accelerometer to detect hand motion and/or shakes and determine the magnitude and frequency of tremors. The sensing system 20020 may send the measurement data associated with the set of biomarkers and the data associated with a physical state of the surgeon to the surgical hub 20006 for further processing. One or more environmental sensing devices may send environmental information to the surgical hub 20006. For example, the environmental sensing devices may include a camera 20021 for detecting hand/body position of an HCP. The environmental sensing devices may include microphones 20022 for measuring the ambient noise in the surgical theater. Other environmental sensing devices may include devices, for example, a thermometer to measure temperature and a hygrometer to measure humidity of the surroundings in the surgical theater, etc. The surgical hub 20006, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 20020 may measure one or more surgeon biomarkers associated with an HCP and send the measurement data associated with the surgeon biomarkers to the surgical hub 20006. The HCP sensing systems 20020 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 20006 may use the surgeon biomarker measurement data associated with an HCP to adaptively control one or more surgical instruments 20031. For example, the surgical hub 20006 may send a control program to a surgical instrument 20031 to control its actuators to limit or compensate for fatigue and use of fine motor skills. The surgical hub 20006 may send the control program based on situational awareness and/or the context on importance or criticality of a task. The control program may instruct the instrument to alter operation to provide more control when control is needed.

Figure 3:
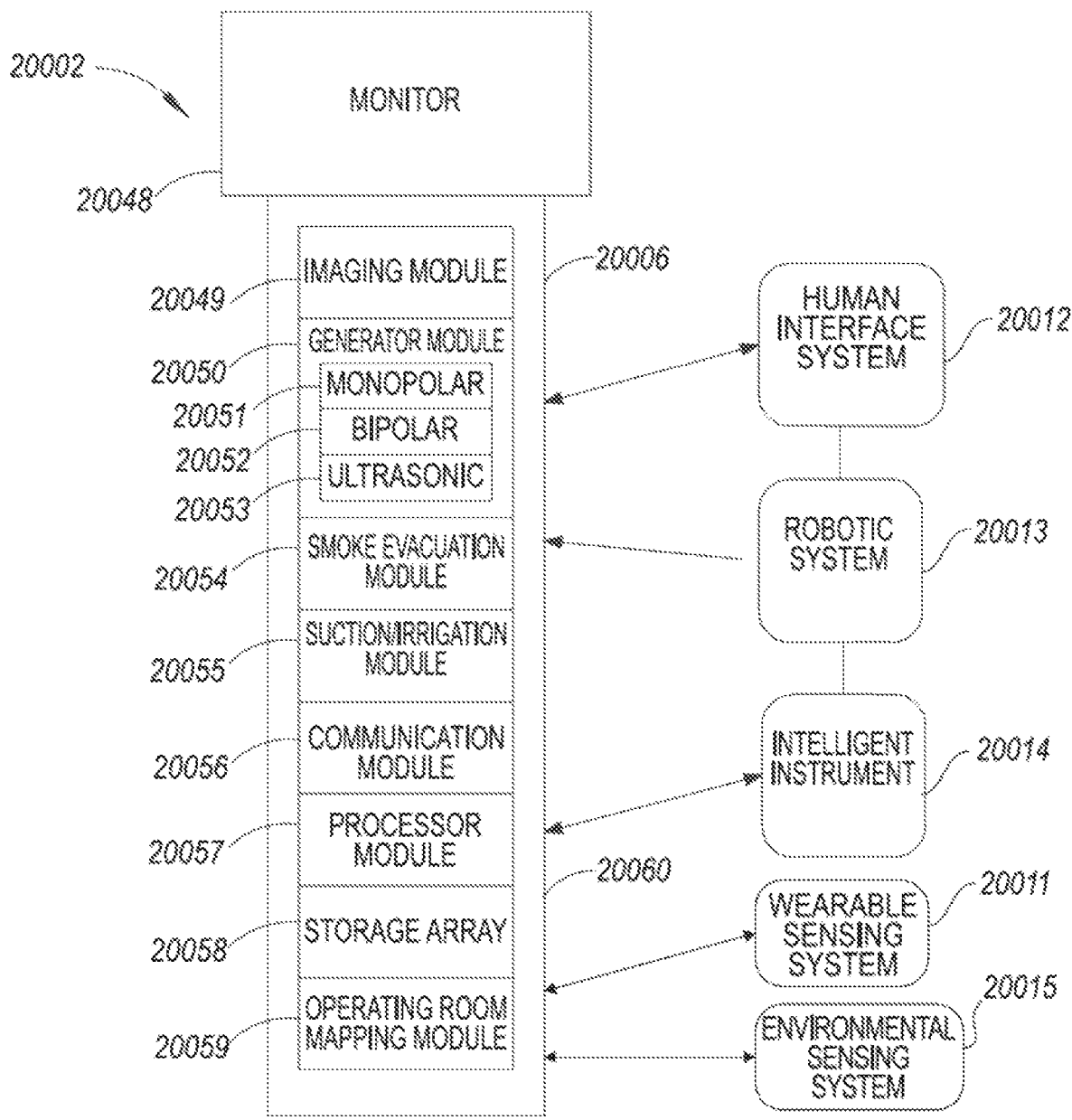
FIG. 3 illustrates an example surgical hub paired with various systems.

FIG. 3 shows an example surgical system 20002 with a surgical hub 20006 paired with a wearable sensing system 20011, an environmental sensing system 20015, a human interface system 20012, a robotic system 20013, and an intelligent instrument 20014. The hub 20006 includes a display 20048, an imaging module 20049, a generator module 20050, a communication module 20056, a processor module 20057, a storage array 20058, and an operating-room mapping module 20059. In certain aspects, as illustrated in FIG. 3, the hub 20006 further includes a smoke evacuation module 20054 and/or a suction/irrigation module 20055. During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 20060 offers a unified environment for managing the power, data, and fluid lines, which reduces the frequency of entanglement between such lines. Aspects of the present disclosure present a surgical hub 20006 for use in a surgical procedure that involves energy application to tissue at a surgical site. The surgical hub 20006 includes a hub enclosure 20060 and a combo generator module slidably receivable in a docking station of the hub enclosure 20060. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 20055 slidably received in the hub enclosure 20060. In one aspect, the hub enclosure 20060 may include a fluid interface. Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 20060 is configured to accommodate different generators and facilitate an interactive communication therebetween. One of the advantages of the hub modular enclosure 20060 is enabling the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 20060 that allows the modular integration of a generator module 20050, a smoke evacuation module 20054, and a suction/irrigation module 20055. The hub modular enclosure 20060 further facilitates interactive communication between the modules 20059, 20054, and 20055. The generator module 20050 can be with integrated monopolar, bipolar, and ultrasonic components supported in a single housing unit slidably insertable into the hub modular enclosure 20060. The generator module 20050 can be configured to connect to a monopolar device 20051, a bipolar device 20052, and an ultrasonic device 20053. Alternatively, the generator module 20050 may comprise a series of monopolar, bipolar, and/or ultrasonic generator modules that interact through the hub modular enclosure 20060. The hub modular enclosure 20060 can be configured to facilitate the insertion of multiple generators and interactive communication between the generators docked into the hub modular enclosure 20060 so that the generators would act as a single generator.

Figure 4:
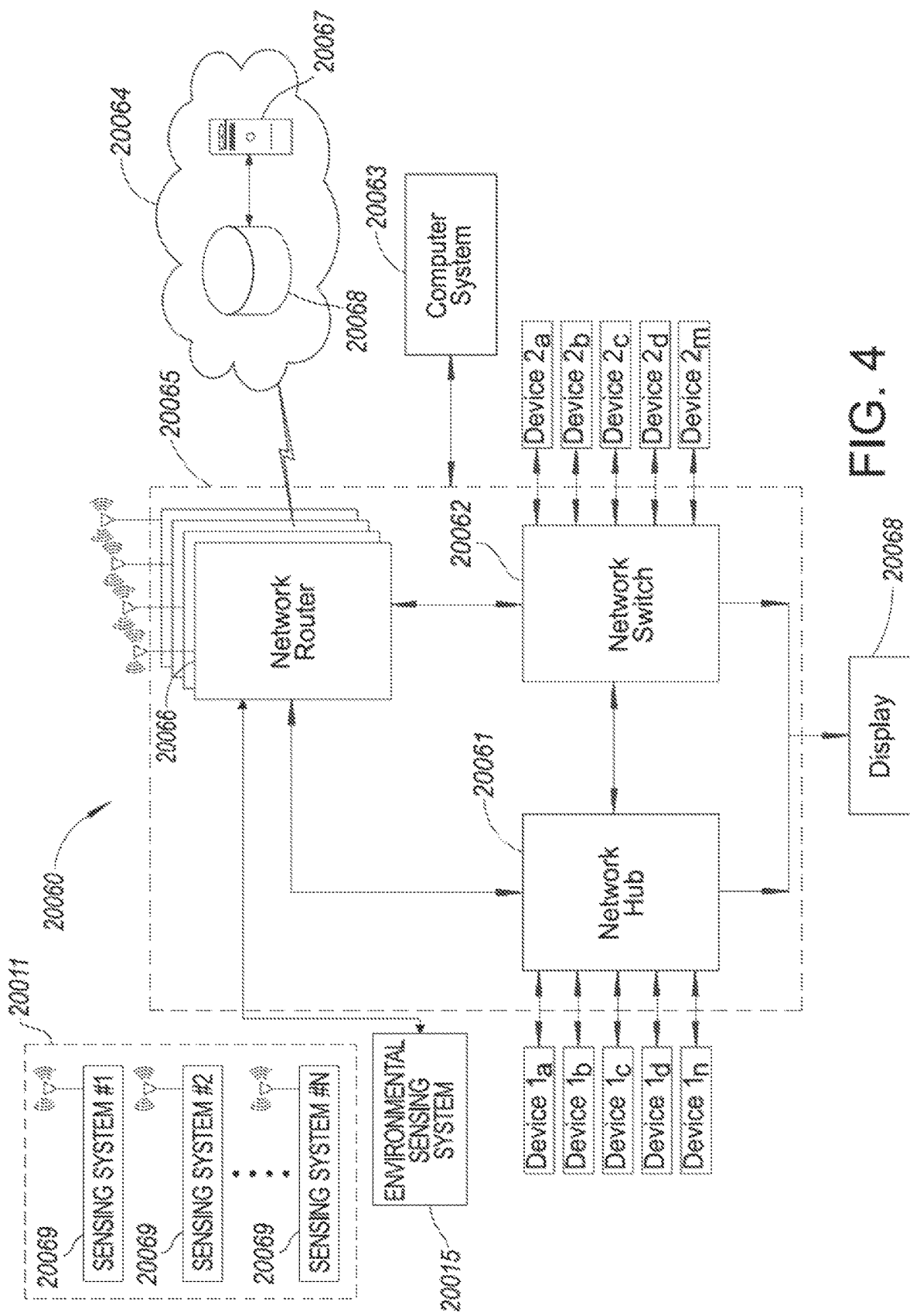
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 20060 may include a modular communication hub 20065 that is configured to connect modular devices located in a healthcare facility to a cloud-based system (e.g., a cloud computing system 20064 that may include a remote server 20067 coupled to a remote storage 20068). The modular communication hub 20065 and the devices may be connected in a room in a healthcare facility specially equipped for surgical operations. In one aspect, the modular communication hub 20065 may include a network hub 20061 and/or a network switch 20062 in communication with a network router 20066. The modular communication hub 20065 may be coupled to a local computer system 20063 to provide local computer processing and data manipulation.

The computer system 20063 may comprise a processor and a network interface 20100. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 20063 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 20063 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor 20102 through the system bus via interface port(s). The interface port(s) include, for example, a serial port, a parallel port, a game port, and a USB. The output device(s) use some of the same types of ports as input device(s). Thus, for example, a USB port may be used to provide input to the computer system 20063 and to output information from the computer system 20063 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 20063 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 20063 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 20063, it can also be external to the computer system 20063. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 20060 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 20061 or network switch 20062. An intelligent surgical data network may be referred to as a manageable hub or switch. A switching hub reads the destination address of each packet and then forwards the packet to the correct port.

Modular devices 1a-1n located in the operating theater may be coupled to the modular communication hub 20065. The network hub 20061 and/or the network switch 20062 may be coupled to a network router 20066 to connect the devices 1a-1n to the cloud computing system 20064 or the local computer system 20063. Data associated with the devices 1a-1n may be transferred to cloud-based computers via the router for remote data processing and manipulation. Data associated with the devices 1a-1n may also be transferred to the local computer system 20063 for local data processing and manipulation. Modular devices 2a-2m located in the same operating theater also may be coupled to a network switch 20062. The network switch 20062 may be coupled to the network hub 20061 and/or the network router 20066 to connect the devices 2a-2m to the cloud 20064. Data associated with the devices 2a-2m may be transferred to the cloud computing system 20064 via the network router 20066 for data processing and manipulation. Data associated with the devices 2a-2m may also be transferred to the local computer system 20063 for local data processing and manipulation.

The wearable sensing system 20011 may include one or more sensing systems 20069. The sensing systems 20069 may include an HCP sensing system and/or a patient sensing system. The one or more sensing systems 20069 may be in communication with the computer system 20063 of a surgical hub system 20060 or the cloud server 20067 directly via one of the network routers 20066 or via a network hub 20061 or network switching 20062 that is in communication with the network routers 20066.

The sensing systems 20069 may be coupled to the network router 20066 to connect to the sensing systems 20069 to the local computer system 20063 and/or the cloud computing system 20064. Data associated with the sensing systems 20069 may be transferred to the cloud computing system 20064 via the network router 20066 for data processing and manipulation. Data associated with the sensing systems 20069 may also be transferred to the local computer system 20063 for local data processing and manipulation.

As illustrated in FIG. 4, the surgical hub system 20060 may be expanded by interconnecting multiple network hubs 20061 and/or multiple network switches 20062 with multiple network routers 20066. The modular communication hub 20065 may be contained in a modular control tower configured to receive multiple devices 1a-1n/2a-2m. The local computer system 20063 also may be contained in a modular control tower. The modular communication hub 20065 may be connected to a display 20068 to display images obtained by some of the devices 1a-1n/2a-2m, for example during surgical procedures. In various aspects, the devices 1a-1n/2a-2m may include, for example, various modules such as an imaging module coupled to an endoscope, a generator module coupled to an energy-based surgical device, a smoke evacuation module, a suction/irrigation module, a communication module, a processor module, a storage array, a surgical device coupled to a display, and/or a non-contact sensor module, among other modular devices that may be connected to the modular communication hub 20065 of the surgical data network.

In one aspect, the surgical hub system 20060 illustrated in FIG. 4 may comprise a combination of network hub(s), network switch(es), and network router(s) connecting the devices 1a-1n/2a-2m or the sensing systems 20069 to the cloud-base system 20064. One or more of the devices 1a-1n/2a-2m or the sensing systems 20069 coupled to the network hub 20061 or network switch 20062 may collect data in real-time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 20065 and/or computer system 20063 located in the surgical theater (e.g., a fixed, mobile, temporary, or field operating room or space) and to devices connected to the modular communication hub 20065 and/or computer system 20063 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, sensing systems, and other computerized devices located in the operating theater. The hub hardware enables multiple devices, sensing systems, and/or connections to be connected to a computer that communicates with the cloud computing resources and storage.

Applying cloud computer data processing techniques on the data collected by the devices 1a-1n/2a-2m, the surgical data network can provide improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This may include localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud computing system 20064 or the local computer system 20063 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing and using standardized approaches may provide beneficial feedback to either confirm surgical treatments and the behavior of the surgeon or suggest modifications to surgical treatments and the behavior of the surgeon.

Applying cloud computer data processing techniques on the measurement data collected by the sensing systems 20069, the surgical data network can provide improved surgical outcomes, improved recovery outcomes, reduced costs, and improved patient satisfaction. At least some of the sensing systems 20069 may be employed to assess physiological conditions of a surgeon operating on a patient or a patient being prepared for a surgical procedure or a patient recovering after a surgical procedure. The cloud-based computing system 20064 may be used to monitor biomarkers associated with a surgeon or a patient in real-time and to generate surgical plans based at least on measurement data gathered prior to a surgical procedure, provide control signals to the surgical instruments during a surgical procedure, and notify a patient of a complication during post-surgical period.

The operating theater devices 1a-1n may be connected to the modular communication hub 20065 over a wired channel or a wireless channel depending on the configuration of the devices 1a-1n to a network hub 20061. The network hub 20061 may be implemented, in one aspect, as a local network broadcast device that works on the physical layer of the Open System Interconnection (OSI) model. The network hub may provide connectivity to the devices 1a-1n located in the same operating theater network. The network hub 20061 may collect data in the form of packets and sends them to the router in half duplex mode. The network hub 20061 may not store any media access control/Internet Protocol (MAC/IP) to transfer the device data. Only one of the devices 1a-1n can send data at a time through the network hub 20061. The network hub 20061 may not have routing tables or intelligence regarding where to send information and broadcasts all network data across each connection and to a remote server 20067 of the cloud computing system 20064. The network hub 20061 can detect basic network errors such as collisions but having all information broadcast to multiple ports can be a security risk and cause bottlenecks.

The operating theater devices 2a-2m may be connected to a network switch 20062 over a wired channel or a wireless channel. The network switch 20062 works in the data link layer of the OSI model. The network switch 20062 may be a multicast device for connecting the devices 2a-2m located in the same operating theater to the network. The network switch 20062 may send data in the form of frames to the network router 20066 and may work in full duplex mode. Multiple devices 2a-2m can send data at the same time through the network switch 20062. The network switch 20062 stores and uses MAC addresses of the devices 2a-2m to transfer data.

The network hub 20061 and/or the network switch 20062 may be coupled to the network router 20066 for connection to the cloud computing system 20064. The network router 20066 works in the network layer of the OSI model. The network router 20066 creates a route for transmitting data packets received from the network hub 20061 and/or network switch 20062 to cloud-based computer resources for further processing and manipulation of the data collected by any one of or all the devices 1a-1n/2a-2m and wearable sensing system 20011. The network router 20066 may be employed to connect two or more different networks located in different locations, such as, for example, different operating theaters of the same healthcare facility or different networks located in different operating theaters of different healthcare facilities. The network router 20066 may send data in the form of packets to the cloud computing system 20064 and works in full duplex mode. Multiple devices can send data at the same time. The network router 20066 may use IP addresses to transfer data.

In an example, the network hub 20061 may be implemented as a USB hub, which allows multiple USB devices to be connected to a host computer. The USB hub may expand a single USB port into several tiers so that there are more ports available to connect devices to the host system computer. The network hub 20061 may include wired or wireless capabilities to receive information over a wired channel or a wireless channel. In one aspect, a wireless USB short-range, high-bandwidth wireless radio communication protocol may be employed for communication between the devices 1a-1n and devices 2a-2m located in the operating theater.

In examples, the operating theater devices 1a-1n/2a-2m and/or the sensing systems 20069 may communicate to the modular communication hub 20065 via Bluetooth wireless technology standard for exchanging data over short distances (using short-wavelength UHF radio waves in the ISM band from 2.4 to 2.485 GHz) from fixed and mobile devices and building personal area networks (PANs). The operating theater devices 1a-1n/2a-2m and/or the sensing systems 20069 may communicate to the modular communication hub 20065 via a number of wireless or wired communication standards or protocols, including but not limited to Bluetooth, Low-Energy Bluetooth, near-field communication (NFC), Wi-Fi (IEEE 802.11 family), WiMAX (IEEE 802.16 family), IEEE 802.20, new radio (NR), long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth Low-Energy Bluetooth, Bluetooth Smart, and a second communication module may be dedicated to longer-range wireless communications such as GPS, EDGE, GPRS, CDMA, WiMAX, LTE, Ev-DO, HSPA+, HSDPA+, HSUPA+, EDGE, GSM, GPRS, CDMA, TDMA, and others.

The modular communication hub 20065 may serve as a central connection for one or more of the operating theater devices 1a-1n/2a-2m and/or the sensing systems 20069 and may handle a data type known as frames. Frames may carry the data generated by the devices 1a-1n/2a-2m and/or the sensing systems 20069. When a frame is received by the modular communication hub 20065, it may be amplified and/or sent to the network router 20066, which may transfer the data to the cloud computing system 20064 or the local computer system 20063 by using a number of wireless or wired communication standards or protocols, as described herein.

The modular communication hub 20065 can be used as a standalone device or be connected to compatible network hubs 20061 and network switches 20062 to form a larger network. The modular communication hub 20065 can be generally easy to install, configure, and maintain, making it a good option for networking the operating theater devices 1a-1n/2a-2m.

Figure 5:
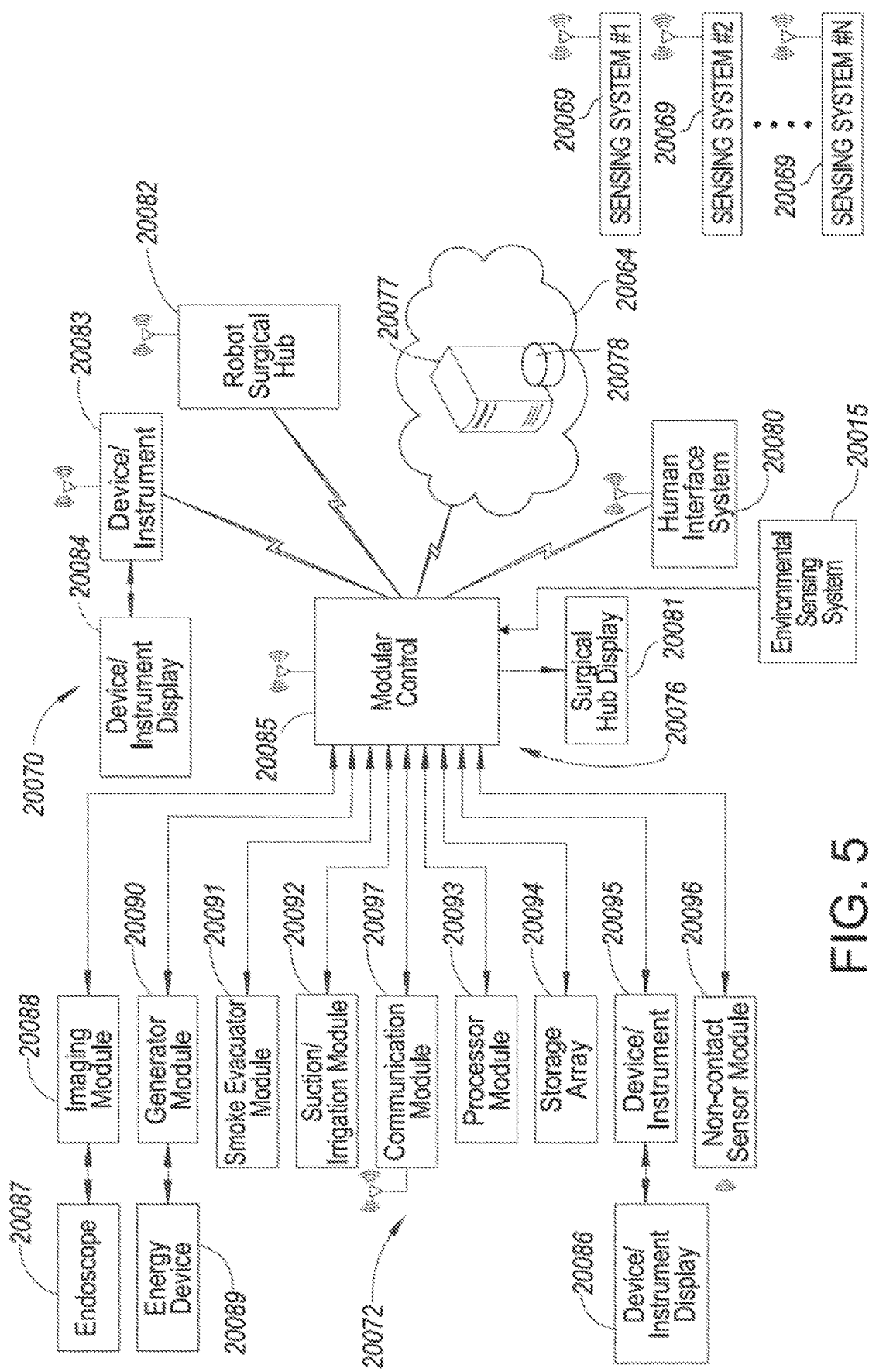
FIG. 5 illustrates an example computer-implemented interactive surgical system that may be part of a surgical system.

FIG. 5 illustrates a computer-implemented interactive surgical system 20070 that may be a part of the Surgical system 20002. The computer-implemented interactive surgical system 20070 is similar in many respects to the HCP sensing system 20002. For example, the computer-implemented interactive surgical system 20070 may include one or more surgical sub-systems 20072, which are similar in many respects to the Surgical systems 20002. Each sub-surgical system 20072 may include at least one surgical hub 20076 in communication with a cloud computing system 20064 that may include a remote server 20077 and a remote storage 20078. In one aspect, the computer-implemented interactive surgical system 20070 may include a modular control 20085 connected to multiple operating theater devices such as sensing systems 20001, intelligent surgical instruments, robots, and other computerized devices located in the operating theater.

As illustrated in the example of FIG. 5, the modular control 20085 may be coupled to an imaging module 20088 that may be coupled to an endoscope 20087, a generator module 20090 that may be coupled to an energy device 20089, a smoke evacuator module 20091, a suction/irrigation module 20092, a communication module 20097, a processor module 20093, a storage array 20094, a smart device/instrument 20095 optionally coupled to a display 20086 and 20084 respectively, and a non-contact sensor module 20096. The non-contact sensor module 20096 may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The modular control 20085 may also be in communication with one or more sensing systems 20069 and an environmental sensing system 20015. The sensing systems 20069 may be connected to the modular control 20085 either directly via a router or via the communication module 20097. The operating theater devices may be coupled to cloud computing resources and data storage via the modular control 20085. A robot surgical hub 20082 also may be connected to the modular control 20085 and to the cloud computing resources. The devices/instruments 20095 or 20084, human interface system 20080, among others, may be coupled to the modular control 20085 via wired or wireless communication standards or protocols, as described herein. The human interface system 20080 may include a display sub-system and a notification sub-system. The modular control 20085 may be coupled to a hub display 20081 (e.g., monitor, screen) to display and overlay images received from the imaging module 20088, device/instrument display 20086, and/or other human interface systems 20080. The hub display 20081 also may display data received from devices connected to the modular control 20085 in conjunction with images and overlaid images.

Figure 6:
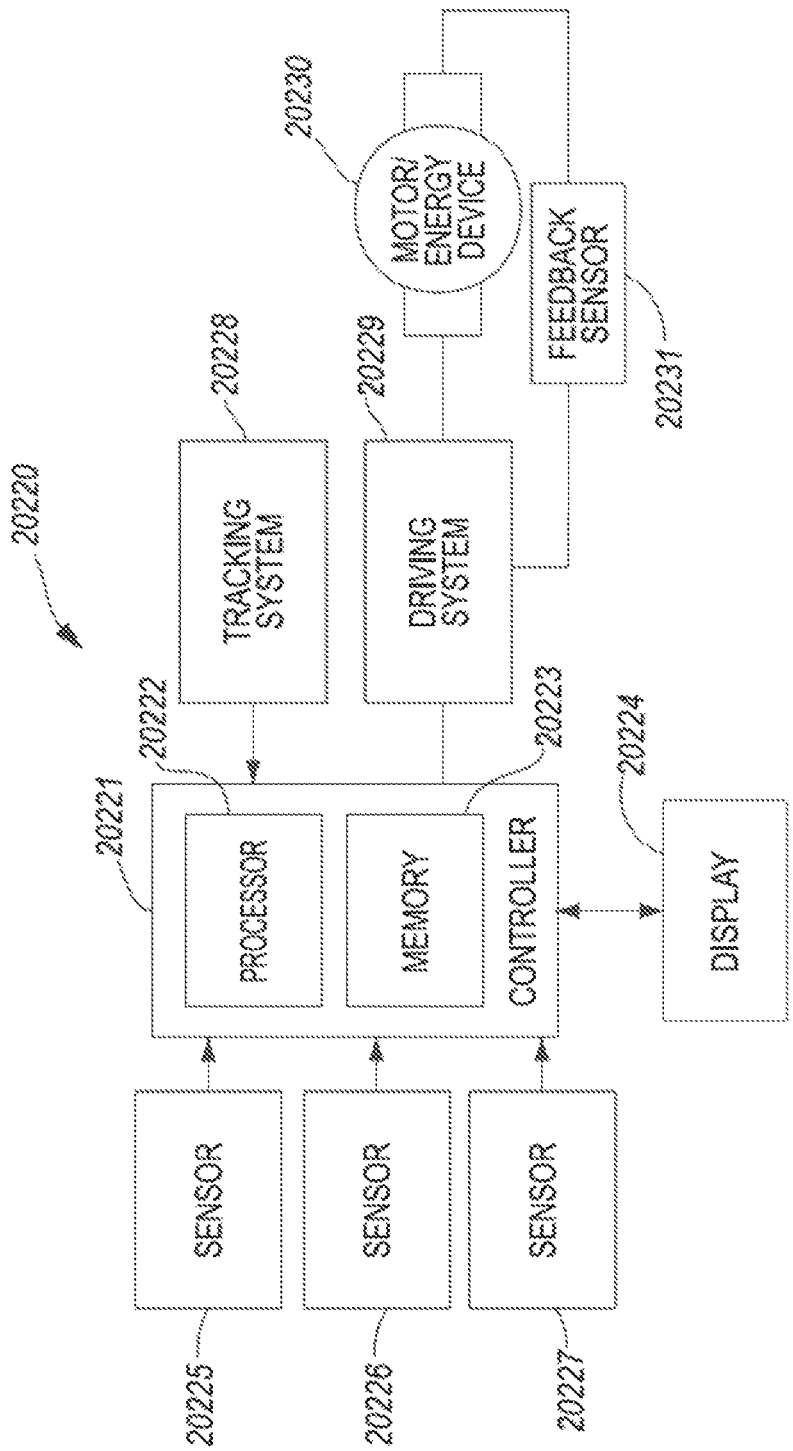
FIG. 6 illustrates a logic diagram of a control system of a surgical instrument.

FIG. 6 illustrates a logical diagram of a control system 20220 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 20220 may comprise a control circuit. The control circuit may include a microcontroller 20221 comprising a processor 20222 and a memory 20223. One or more of sensors 20225, 20226, 20227, for example, provide real-time feedback to the processor 20222. A motor 20230, driven by a motor driver 20229, operably couples a longitudinally movable displacement member to drive the I-beam knife element. A tracking system 20228 may be configured to determine the position of the longitudinally movable displacement member. The position information may be provided to the processor 20222, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 20224 may display a variety of operating conditions of the instruments and may include touch screen functionality for data input. Information displayed on the display 20224 may be overlaid with images acquired via endoscopic imaging modules.

The microcontroller 20221 may be any single-core or multicore processor such as those known under the trade name ARM Cortex by Texas Instruments. In one aspect, the main microcontroller 20221 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 20221 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 20221 may be programmed to perform various functions such as precise control over the speed and position of the knife and articulation systems. In one aspect, the microcontroller 20221 may include a processor 20222 and a memory 20223. The electric motor 20230 may be a brushed direct current (DC) motor with a gearbox and mechanical links to an articulation or knife system. In one aspect, a motor driver 20229 may be an A3941 available from Allegro Microsystems, Inc. Other motor drivers may be readily substituted for use in the tracking system 20228 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 20221 may be programmed to provide precise control over the speed and position of displacement members and articulation systems. The microcontroller 20221 may be configured to compute a response in the software of the microcontroller 20221. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 20230 may be controlled by the motor driver 20229 and can be employed by the firing system of the surgical instrument or tool. In various forms, the motor 20230 may be a brushed DC driving motor having a maximum rotational speed of approximately 25,000 RPM. In some examples, the motor 20230 may include a brushless motor, a cordless motor, a synchronous motor, a stepper motor, or any other suitable electric motor. The motor driver 20229 may comprise an H-bridge driver comprising field-effect transistors (FETs), for example. The motor 20230 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 20229 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 20229 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 20228 comprising an absolute positioning system.

The tracking system 20228 may comprise a controlled motor drive circuit arrangement comprising a position sensor 20225 according to one aspect of this disclosure. The position sensor 20225 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 20225 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 20230 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 20225 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 20225 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 20225 completing one or more revolutions for the full stroke of the displacement member. The position sensor 20225 may complete multiple revolutions for the full stroke of the displacement member.

A series of switches, where n is an integer greater than one, may be employed alone or in combination with a gear reduction to provide a unique position signal for more than one revolution of the position sensor 20225. The state of the switches may be fed back to the microcontroller 20221 that applies logic to determine a unique position signal corresponding to the longitudinal linear displacement d1+ d2+ . . . dn of the displacement member. The output of the position sensor 20225 is provided to the microcontroller 20221. The position sensor 20225 of the sensor arrangement may comprise a magnetic sensor, an analog rotary sensor like a potentiometer, or an array of analog Hall-effect elements, which output a unique combination of position signals or values.

The position sensor 20225 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiberoptic, magneto-optic, and microelectromechanical systems-based magnetic sensors, among others.

The position sensor 20225 for the tracking system 20228 comprising an absolute positioning system may comprise a magnetic rotary absolute positioning system. The position sensor 20225 may be implemented as an AS5055EQFT single-chip magnetic rotary position sensor available from Austria Microsystems, AG. The position sensor 20225 is interfaced with the microcontroller 20221 to provide an absolute positioning system. The position sensor 20225 may be a low-voltage and low-power component and may include four Hall-effect elements in an area of the position sensor 20225 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 20221. The position sensor 20225 may provide 12 or 14 bits of resolution. The position sensor 20225 may be an AS5055 chip provided in a small QFN 16-pin 4×4×0.85 mm package.

The tracking system 20228 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 20225. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 20230 has taken to infer the position of a device actuator, drive bar, knife, or the like.

A sensor 20226, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 20222. Alternatively, or in addition to the sensor 20226, a sensor 20227, such as, for example, a load sensor, can measure the closure force applied by the closure drive system to the anvil. The sensor 20227, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 20231 can be employed to measure the current drawn by the motor 20230. The force required to advance the firing member can correspond to the current drawn by the motor 20230, for example. The measured force may be converted to a digital signal and provided to the processor 20222.

For example, the strain gauge sensor 20226 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 20226, such as, for example, a micro-strain gauge, that can be configured to measure one or more parameters of the end effector, for example. In one aspect, the strain gauge sensor 20226 can measure the amplitude or magnitude of the strain exerted on a jaw member of an end effector during a clamping operation, which can be indicative of the tissue compression. The measured strain can be converted to a digital signal and provided to a processor 20222 of the microcontroller 20221. A load sensor 20227 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 20222.

The measurements of the tissue compression, the tissue thickness, and/or the force required to close the end effector on the tissue, as respectively measured by the sensors 20226, 20227, can be used by the microcontroller 20221 to characterize the selected position of the firing member and/or the corresponding value of the speed of the firing member. In one instance, a memory 20223 may store a technique, an equation, and/or a lookup table which can be employed by the microcontroller 20221 in the assessment.

The control system 20220 of the surgical instrument or tool also may comprise wired or wireless communication circuits to communicate with the modular communication hub 20065 as shown in FIG. 5.

Figure 7:
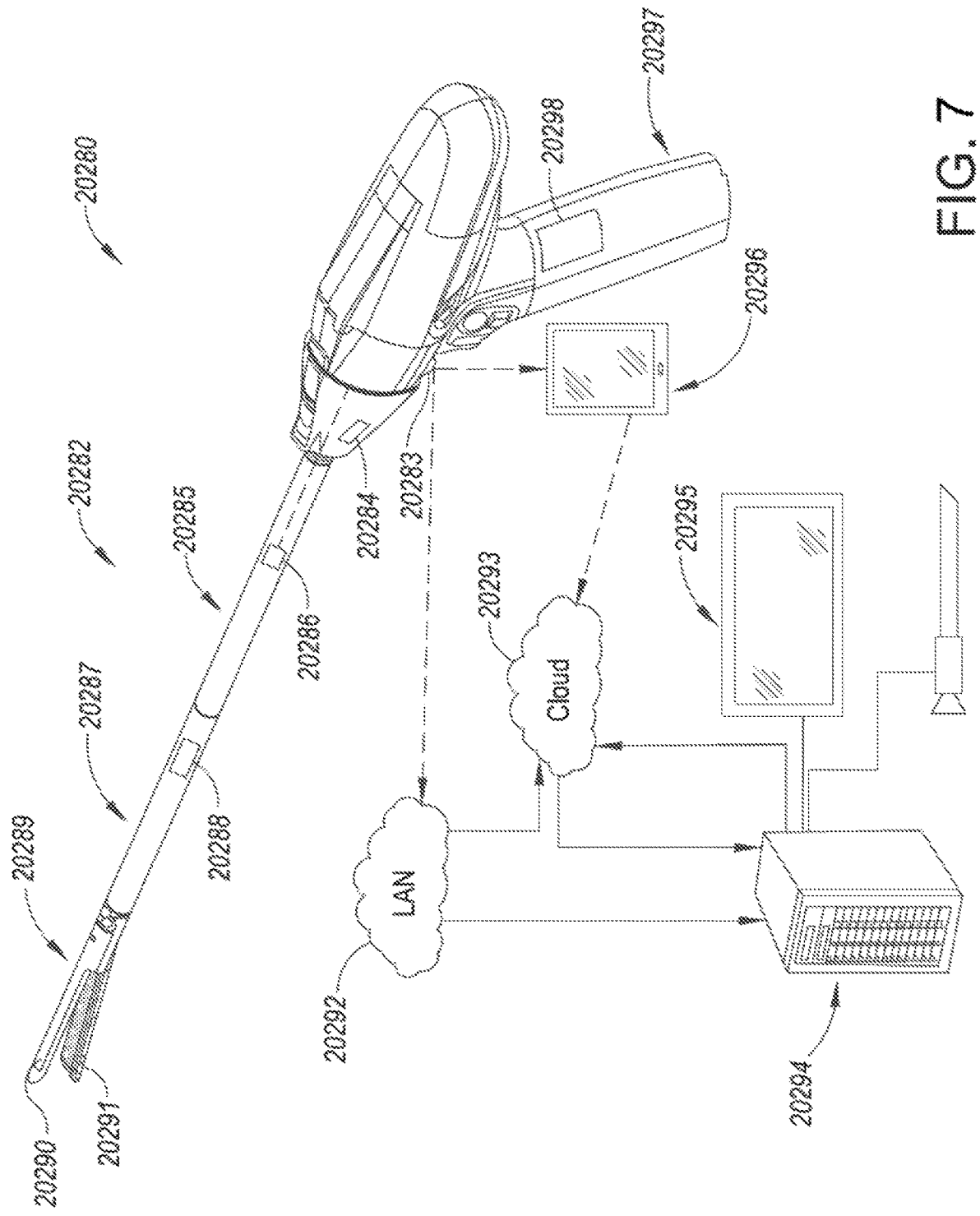
FIG. 7 shows an example surgical system that includes a handle having a controller and a motor, an adapter releasably coupled to the handle, and a loading unit releasably coupled to the adapter.

FIG. 7 illustrates an example surgical system 20280 in accordance with the present disclosure and may include a surgical instrument 20282 that can be in communication with a console 20294 or a portable device 20296 through a local area network 20292 and/or a cloud network 20293 via a wired and/or wireless connection. The console 20294 and the portable device 20296 may be any suitable computing device. The surgical instrument 20282 may include a handle 20297, an adapter 20285, and a loading unit 20287. The adapter 20285 releasably couples to the handle 20297 and the loading unit 20287 releasably couples to the adapter 20285 such that the adapter 20285 transmits a force from a drive shaft to the loading unit 20287. The adapter 20285 or the loading unit 20287 may include a force gauge (not explicitly shown) disposed therein to measure a force exerted on the loading unit 20287. The loading unit 20287 may include an end effector 20289 having a first jaw 20291 and a second jaw 20290. The loading unit 20287 may be an in-situ loaded or multi-firing loading unit (MFLU) that allows a clinician to fire a plurality of fasteners multiple times without requiring the loading unit 20287 to be removed from a surgical site to reload the loading unit 20287.

The first and second jaws 20291, 20290 may be configured to clamp tissue therebetween, fire fasteners through the clamped tissue, and sever the clamped tissue. The first jaw 20291 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 20290 may include an anvil that deforms or otherwise secures the fasteners, as the fasteners are ejected from the multi-fire fastener cartridge.

The handle 20297 may include a motor that is coupled to the drive shaft to affect rotation of the drive shaft. The handle 20297 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 20297 may be in communication with a controller 20298 of the handle 20297 to selectively activate the motor to affect rotation of the drive shafts. The controller 20298 may be disposed within the handle 20297 and may be configured to receive input from the control interface and adapter data from the adapter 20285 or loading unit data from the loading unit 20287. The controller 20298 may analyze the input from the control interface and the data received from the adapter 20285 and/or loading unit 20287 to selectively activate the motor. The handle 20297 may also include a display that is viewable by a clinician during use of the handle 20297. The display may be configured to display portions of the adapter or loading unit data before, during, or after firing of the instrument 20282.

The adapter 20285 may include an adapter identification device 20284 disposed therein and the loading unit 20287 may include a loading unit identification device 20288 disposed therein. The adapter identification device 20284 may be in communication with the controller 20298, and the loading unit identification device 20288 may be in communication with the controller 20298. It will be appreciated that the loading unit identification device 20288 may be in communication with the adapter identification device 20284, which relays or passes communication from the loading unit identification device 20288 to the controller 20298.

The adapter 20285 may also include a plurality of sensors 20286 (one shown) disposed thereabout to detect various conditions of the adapter 20285 or of the environment (e.g., if the adapter 20285 is connected to a loading unit, if the adapter 20285 is connected to a handle, if the drive shafts are rotating, the torque of the drive shafts, the strain of the drive shafts, the temperature within the adapter 20285, a number of firings of the adapter 20285, a peak force of the adapter 20285 during firing, a total amount of force applied to the adapter 20285, a peak retraction force of the adapter 20285, a number of pauses of the adapter 20285 during firing, etc.). The plurality of sensors 20286 may provide an input to the adapter identification device 20284 in the form of data signals. The data signals of the plurality of sensors 20286 may be stored within or be used to update the adapter data stored within the adapter identification device 20284. The data signals of the plurality of sensors 20286 may be analog or digital. The plurality of sensors 20286 may include a force gauge to measure a force exerted on the loading unit 20287 during firing.

The handle 20297 and the adapter 20285 can be configured to interconnect the adapter identification device 20284 and the loading unit identification device 20288 with the controller 20298 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 20284 and the controller 20298 may be in wireless communication with one another via a wireless connection separate from the electrical interface.

The handle 20297 may include a transceiver 20283 that is configured to transmit instrument data from the controller 20298 to other components of the system 20280 (e.g., the LAN 20292, the cloud 20293, the console 20294, or the portable device 20296). The controller 20298 may also transmit instrument data and/or measurement data associated with one or more sensors 20286 to a surgical hub. The transceiver 20283 may receive data (e.g., cartridge data, loading unit data, adapter data, or other notifications) from the surgical hub 20270. The transceiver 20283 may receive data (e.g., cartridge data, loading unit data, or adapter data) from the other components of the system 20280. For example, the controller 20298 may transmit instrument data including a serial number of an attached adapter (e.g., adapter 20285) attached to the handle 20297, a serial number of a loading unit (e.g., loading unit 20287) attached to the adapter 20285, and a serial number of a multi-fire fastener cartridge loaded into the loading unit to the console 20294. Thereafter, the console 20294 may transmit data (e.g., cartridge data, loading unit data, or adapter data) associated with the attached cartridge, loading unit, and adapter, respectively, back to the controller 20298. The controller 20298 can display messages on the local instrument display or transmit the message, via transceiver 20283, to the console 20294 or the portable device 20296 to display the message on the display 20295 or portable device screen, respectively.

Figure 8:
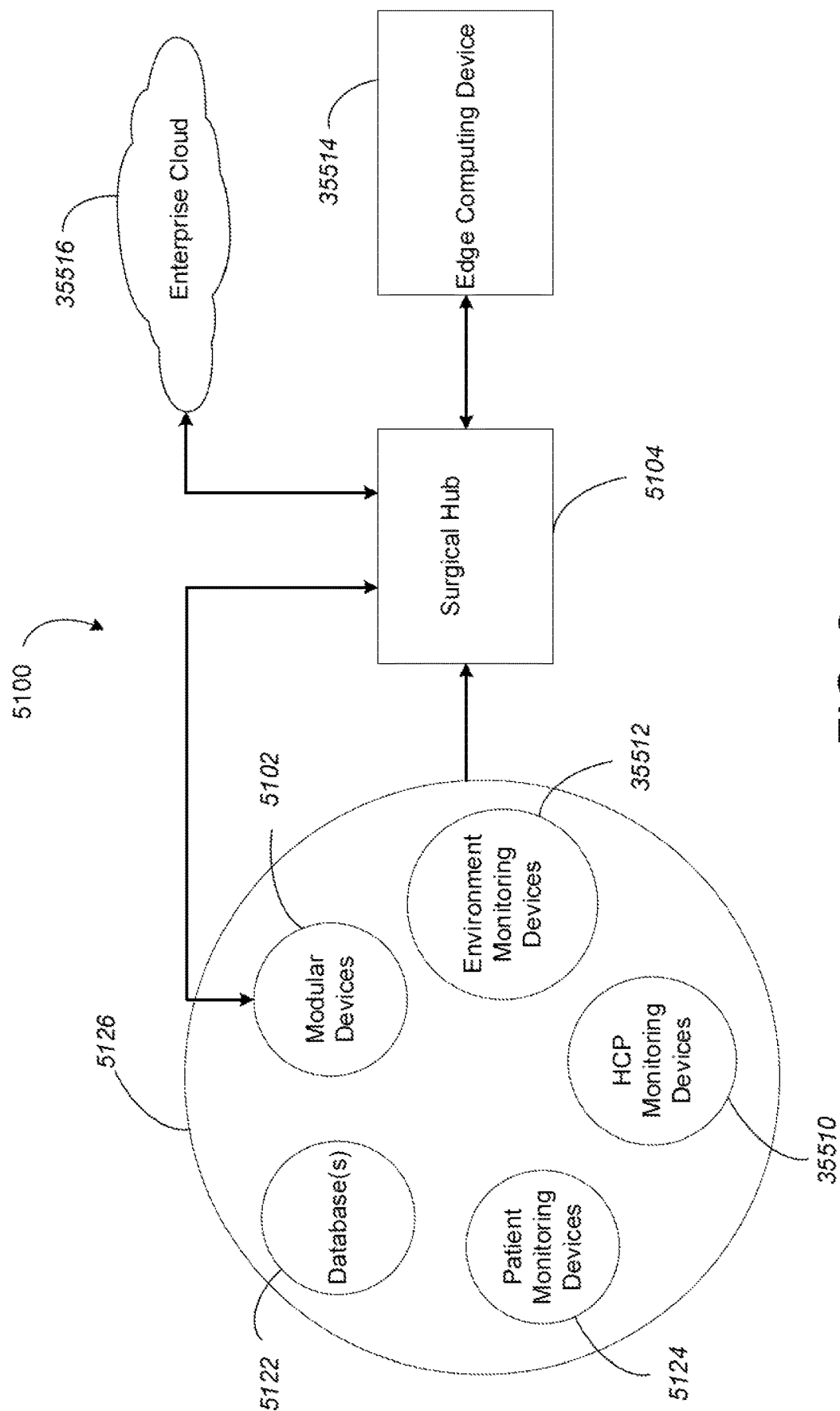
FIG. 8 shows an example situationally aware surgical system.

FIG. 8 illustrates a diagram of a situationally aware surgical system 5100, in accordance with at least one aspect of the present disclosure. The data sources 5126 may include, for example, the modular devices 5102 (which can include sensors configured to detect parameters associated with the patient, HCPs and environment and/or the modular device itself), databases 5122 (e.g., an EMR database containing patient records), patient monitoring devices 5124 (e.g., a blood pressure (BP) monitor and an electrocardiography (EKG) monitor), HCP monitoring devices 35510, and/or environment monitoring devices 35512. The surgical hub 5104 can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." For example, the surgical hub 5104 can incorporate a situational awareness system, which is the hardware and/or programming associated with the surgical hub 5104 that derives contextual information pertaining to the surgical procedure from the received data and/or a surgical plan information received from the edge computing system 35514 or an enterprise cloud server 35516.

The situational awareness system of the surgical hub 5104 can be configured to derive the contextual information from the data received from the data sources 5126 in a variety of different ways. For example, the situational awareness system can include a pattern recognition system, or machine learning system (e.g., an artificial neural network), that has been trained on training data to correlate various inputs (e.g., data from database(s) 5122, patient monitoring devices 5124, modular devices 5102, HCP monitoring devices 35510, and/or environment monitoring devices 35512) to corresponding contextual information regarding a surgical procedure. A machine learning system can be trained to accurately derive contextual information regarding a surgical procedure from the provided inputs. In examples, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In examples, the contextual information received by the situational awareness system of the surgical hub 5104 can be associated with a particular control adjustment or set of control adjustments for one or more modular devices 5102. In examples, the situational awareness system can include a further machine learning system, lookup table, or other such system, which generates or retrieves one or more control adjustments for one or more modular devices 5102 when provided the contextual information as input.

A surgical hub 5104 incorporating a situational awareness system can provide a number of benefits for the surgical system 5100. One benefit may include improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

The type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

The type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type can be generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

The type of procedure being performed can affect the optimal energy level for an ultrasonic surgical instrument or radio frequency (RF) electrosurgical instrument to operate at. Arthroscopic procedures, for example, may require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (e.g., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

In examples, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (e.g., whether bleeding at a surgical site has stopped) according to video or image data received from a medical imaging device. The surgical hub 5104 can be further configured to compare a physiologic measurement (e.g., blood pressure sensed by a BP monitor communicably connected to the surgical hub 5104) with the visual or image data of hemostasis (e.g., from a medical imaging device communicably coupled to the surgical hub 5104) to make a determination on the integrity of the staple line or tissue weld. The situational awareness system of the surgical hub 5104 can consider the physiological measurement data to provide additional context in analyzing the visualization data. The additional context can be useful when the visualization data may be inconclusive or incomplete on its own.

For example, a situationally aware surgical hub 5104 could proactively activate the generator to which an RF electrosurgical instrument is connected if it determines that a subsequent step of the procedure requires the use of the instrument. Proactively activating the energy source can allow the instrument to be ready for use as soon as the preceding step of the procedure is completed.

The situationally aware surgical hub 5104 could determine whether the current or subsequent step of the surgical procedure requires a different view or degree of magnification on the display according to the feature(s) at the surgical site that the surgeon is expected to need to view. The surgical hub 5104 could proactively change the displayed view (supplied by, e.g., a medical imaging device for the visualization system) accordingly so that the display automatically adjusts throughout the surgical procedure.

The situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Errors may be checked during the setup of the surgical procedure or during the course of the surgical procedure. For example, the situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In some exemplifications, the surgical hub 5104 can compare the list of items for the procedure and/or a list of devices paired with the surgical hub 5104 to a recommended or anticipated manifest of items and/or devices for the given surgical procedure. If there are any discontinuities between the lists, the surgical hub 5104 can provide an alert indicating that a particular modular device 5102, patient monitoring device 5124, HCP monitoring devices 35510, environment monitoring devices 35512, and/or other surgical item is missing. In some examples, the surgical hub 5104 can determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

The situationally aware surgical hub 5104 could determine whether the surgeon (or other HCP(s)) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. The surgical hub 5104 can provide an alert indicating that an unexpected action is being performed or an unexpected device is being utilized at the particular step in the surgical procedure.

The surgical instruments (and other modular devices 5102) may be adjusted for the particular context of each surgical procedure (such as adjusting to different tissue types) and validating actions during a surgical procedure. Next steps, data, and display adjustments may be provided to surgical instruments (and other modular devices 5102) in the surgical theater according to the specific context of the procedure.

Machine learning is a branch of artificial intelligence that seeks to build computer systems that may learn from data without human intervention. These techniques may rely on the creation of analytical models that may be trained to recognize patterns within a dataset, such as a data collection. These models may be deployed to apply these patterns to data, such as biomarkers, to improve performance without further guidance.

Machine learning may be supervised (e.g., supervised learning). A supervised learning algorithm may create a mathematical model from training a dataset (e.g., training data). The training data may comprise a set of training examples. A training example may include one or more inputs and one or more labeled outputs. The labeled output(s) may serve as supervisory feedback. In a mathematical model, a training example may be represented by an array or a vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function may determine the output for one or more inputs that may not have been part of the training data. Example algorithms may include linear regression, logistic regression, and neutral network. Example problems solvable by supervised learning algorithms may include classification, regression problems, and the like.

Machine learning may be unsupervised (e.g., unsupervised learning). An unsupervised learning algorithm may train on a dataset that may include inputs and the unsupervised learning algorithm may find a structure in the data. The structure in the data may be similar to a grouping or clustering of data points. As such, the algorithm may learn from training data that may not have been labeled. Instead of responding to supervisory feedback, an unsupervised learning algorithm may identify commonalities in training data and may react based on the presence or absence of such commonalities in each training example. Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like.

Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of a machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal is reached, the linear prediction function with adjusted coefficients may be deemed trained and may constitute the model the training process has produced. For example, a neural network (NN) algorithm (e.g., multilayer perceptions (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum is reached, the optimized hypothesis function with its layers of adjusted biases and weights may be deemed trained and may constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources comprising pre-surgical data, such as a patient's medical conditions and biomarker measurement data, may be identified. Such data sources may be a patient's electronic medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g., logically linked) and may be accessed as if they were centrally stored. Surgical data and/or post-surgical data may be similarly identified and/or collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. In an example, a patient's integrated data record of pre-surgical EMR record data and biomarker measurement data, surgical data, and post-surgical data may be in a rational database. Such data record may be converted to a flat file format for model training. In an example, the patient's pre-surgical EMR data may include medical data in text format, such as the patient's diagnoses of emphysema, pre-operative treatment (e.g., chemotherapy, radiation, blood thinner). Such data may be mapped to numeric values for model training. For example, the patient's integrated data record may include personal identifier information or other information that may identifier a patient such as an age, an employer, a body mass index (BMI), demographic information, and the like. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or scaled down, for example, to be between 0 and 1 for model training. For example, the preprocessed data may include data values that carry more meaning when aggregated. In an example, there may be multiple prior colorectal procedures a patient has had. The total count of prior colorectal procedures may be more meaningful for training a model to predict surgical complications due to adhesions. In such case, the records of prior colorectal procedures may be aggregated into a total count for model training purposes.

Model training may be another aspect of the machine learning lifecycle. The model training process as described herein may be dependent on the machine learning algorithm used. A model may be deemed suitably trained after it has been trained, cross-validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. Overfitting may be detected, for example, when the accuracy of the model may decrease when run against the validation dataset after the accuracy of the model has been increasing. The test dataset may be used to test the accuracy of the final model to determine whether the test dataset is ready for deployment or more training may be required.

Model deployment may be another aspect of the machine learning lifecycle. The model may be deployed as part of a standalone computer program. The model may be deployed as part of a larger computing system. A model may be deployed with model performance parameters(s). Such performance parameters may monitor the model accuracy as it is used for predicting on a dataset in production. For example, such parameters may keep track of false positives and false negative for a classification model. Such parameters may further store the false positives and false negatives for further processing to improve the model's accuracy.

Post-deployment model updates may be another aspect of the machine learning cycle. For example, a deployed model may be updated as false positives and/or false negatives are predicted on production data. In an example, for a deployed MLP model for classification, as false positives occur, the deployed MLP model may be updated to increase the probably cutoff for predicting a positive in order to reduce false positives. In an example, for a deployed MLP model for classification, as false negatives occur, the deployed MLP model may be updated to decrease the probably cutoff for predicting a negative to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

Figure 9:
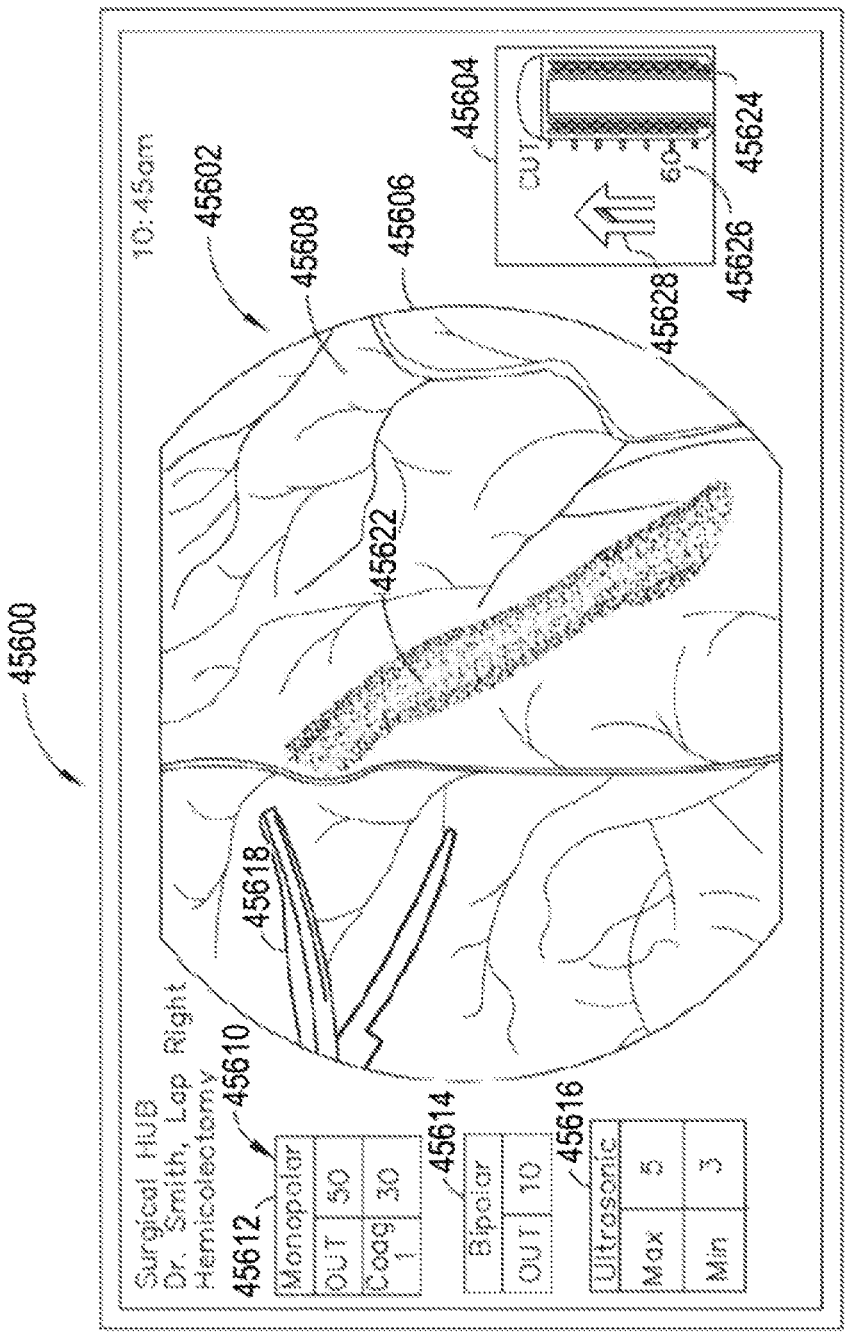
FIG. 9 illustrates a display of the surgical hub.

FIG. 9 illustrates a display of the surgical hub. For example, FIG. 9 illustrates an example primary display 45600 associated with the surgical hub 20006 comprising a global display window 45602 and a local instrument display window 45604, according to one aspect of the present disclosure. The global display window 45602 may show a field of view 45606 of a surgical site 45608, as viewed through a medical imaging device such as, for example, a laparoscope/endoscope coupled to an imaging module, at the center of a display, referred to herein also as a display and/or a monitor, for example. The end effector 45618 portion of the connected instrument may be shown in the field of view 45606 of the surgical site 45608 in the global display window 45602. The images shown on the display located on an instrument coupled to the surgical hub 20006 may be shown, or mirrored, on the local instrument display window 45604 located in the lower right corner of the monitor (e.g., primary display) 45600 as shown in FIG. 9, for example.

During operation, relevant instrument information and menus may be displayed on the display located on the instrument until the instrument senses a connection of the instrument to the surgical hub 20006 at which point all or some sub-set of the information presented on the instrument display may be displayed (e.g., only) on the local instrument display window 45604 portion of the surgical hub display (e.g., primary display) 45600 through the surgical hub 20006. The information displayed on the local instrument display window may be mirrored on the display located on the instrument or may be no longer accessible on the instrument display detonated screen. This technique frees up the instrument to show different information or to show larger font information on the surgical hub display 45600.

The primary display 45600 may provide perioperative visualization of the surgical site. Advanced imaging may identify and visually highlight 45622 critical structures such as the ureter 45620 (or nerves, etc.) and may track instrument proximity displays 45610 shown on the left side of the display 45600. In the illustrated example, the instrument proximity displays 45610 may show instrument specific settings. For example, the top instrument proximity display 45612 may show settings for a monopolar instrument, the middle instrument proximity display 45614 may show settings for a bipolar instrument, and the bottom instrument proximity display 45616 may show settings for an ultrasonic instrument.

One or more secondary displays, which may be dedicated local displays, may be linked to the surgical hub 20006 to provide both an interaction portal via a touchscreen display and/or a secondary screen that may display any number of surgical hub 20006 tracked data feeds to provide a status. The secondary screen may display force to fire (FTF), tissue gap, power level, impedance, tissue compression stability (creep), etc., while the primary screen may display key variables (e.g., only key variables) to keep the feed free of clutter. The interactive display may be used to move information that may be on the display a desired location. The interactive display may allow a user to change a character of the information, such as a size associated with the information, a color associated with the information, and/or the like. For example, a user may use the interactive display to move information to a primary display where the information may be highlighted and/or shown more prominently than other data.

As shown in FIG. 9, the secondary screen displays the instrument proximity displays 45610 on the left side of the display 45600 and the local instrument display window 45604 on the bottom right side of the display 45600. The local instrument display 45604 presented on the surgical hub display 45600 displays an icon of the end effector 45618, such as the icon of a staple cartridge 45624 currently in use, the size 45626 of the staple cartridge 45624 (e.g., 60 mm), and an icon of the current position of the knife 45628 of the end effector.

The display located on the instrument may display the wireless or wired attachment of the instrument to the surgical hub 20006 and the instrument's communication/recording on the surgical hub 20006. A setting may be provided on the instrument to enable the user to select mirroring or extending the display to both monitoring devices. The instrument controls may be used to interact with the display of information being shown on the instrument. As disclosed herein, the instrument may comprise wireless communication circuits to communicate wirelessly with the surgical hub 20006.

A first instrument coupled to the surgical hub 20006 may pair to a screen of a second instrument coupled to the surgical hub 20006. This may allow both instruments to display some hybrid combination of information from the two devices of both becoming mirrors of portions of the primary display.

The primary display 45600 of the surgical hub 20006 may provide a 360° composite top visual view of the surgical site 45608 to avoid collateral structures. For example, a secondary display of the end-effector surgical stapler may be provided within the primary display 45600 of the surgical hub 20006 or on another display in order to provide better perspective around the areas within a current field of view 45606.

Figure 10:
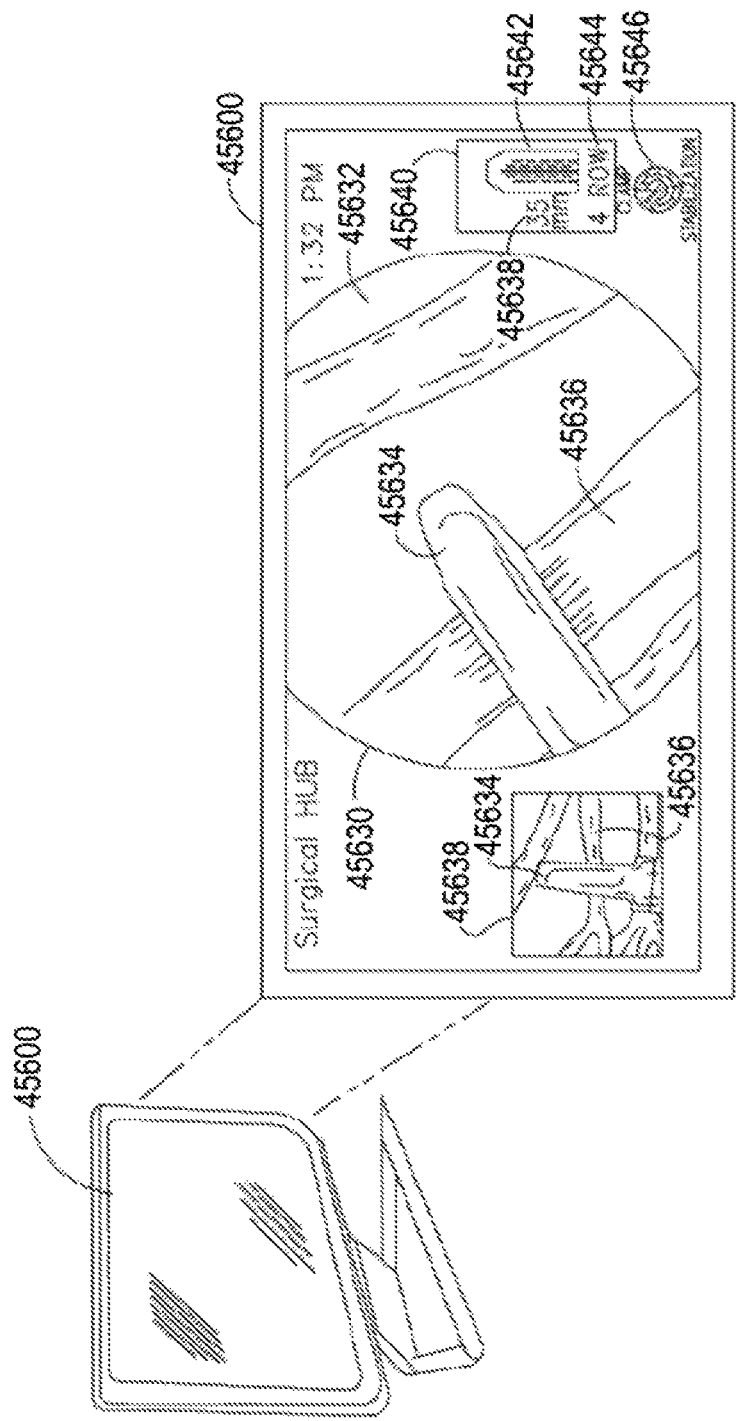
FIG. 10 illustrates an example primary display of the surgical hub.

FIG. 10 illustrates an example primary display of the surgical hub. For example, FIG. 10 may illustrate an example primary display comprising composite overhead views of an end-effector 45634 portion of a surgical stapler. The views may be mapped using two or more imaging arrays, and array and time, and/or the like to provide multiple perspective views of the end-effector 45634 to enable the composite imaging of an overhead field of view.

The techniques described herein may be applied to ultrasonic instruments, electrosurgical instruments, combination ultrasonic/electrosurgical instruments, and/or combination surgical stapler/electrosurgical instruments. Several techniques may be performed for overlaying or augmenting images and/or text from multiple image/text sources to present composite images on a display (e.g., a single display). Further examples are disclosed in U.S. Patent. Application Publication No. 2019-0201104 A1 (U.S. patent application Ser. No. 15/940,671), titled SURGICAL HUB SPATIAL AWARENESS TO DETERMINE DEVICES IN OPERATING THEATER, filed Mar. 29, 2018, which is herein incorporated by reference in its entirety.

As shown in FIG. 10, a primary display 45600 of the surgical hub 20006 may display a primary window 45630. The primary window 45630 may be located at the center of the screen and may show a magnified or exploded narrow angle view of a surgical field of view 45632. The primary window 45630 located in the center of the screen may show a magnified or narrow angle view of an end-effector 45634 of the surgical stapler grasping a vessel 45636. The primary window 45630 may display knitted images to produce a composite image that enables visualization of structures adjacent to the surgical field of view 45632. A second window 45638 may be shown in the lower left corner of the primary display 45600. The second window 45638 may display a knitted image in a wide-angle view at standard focus of the image shown in the primary window 45630 in an overhead view. The overhead view provided in the second window 45638 may enable the viewer to easily see items that are out of the narrow field surgical field of view 45632 without moving the laparoscope, or other imaging devices coupled to the imaging module of the surgical hub 20006. A third window 45640 shown in the lower right corner of the primary display 45600 may show an icon 45642 representative of the staple cartridge of the end-effector 45634 (e.g., a staple cartridge in this instance) and additional information such as "4 Row" indicating the number of staple rows 45644 and "35 mm" indicating the distance 6248 traversed by the knife along the length of the staple cartridge. Below the third window 45640 is displayed an icon 45646 of a frame of the current state of a clamp stabilization sequence 6250 that indicates clamp stabilization.

In an example visualization control mode, display may be controlled by the user, for example, via motion tracking (e.g., head orientation relative to a monitor), hand gestures, voice activation, and other means within the sterile field. A user may use gestures, motion tracking commands, voice activation, and the like to move data from one display to another display. For example, a user may use a gesture to move data from a first display to a second display. The gesture may be detected by the hub and the hub may instruct the first display to remove the data or stop displaying the data and may instruct the second display to display the data.

Figure 11:
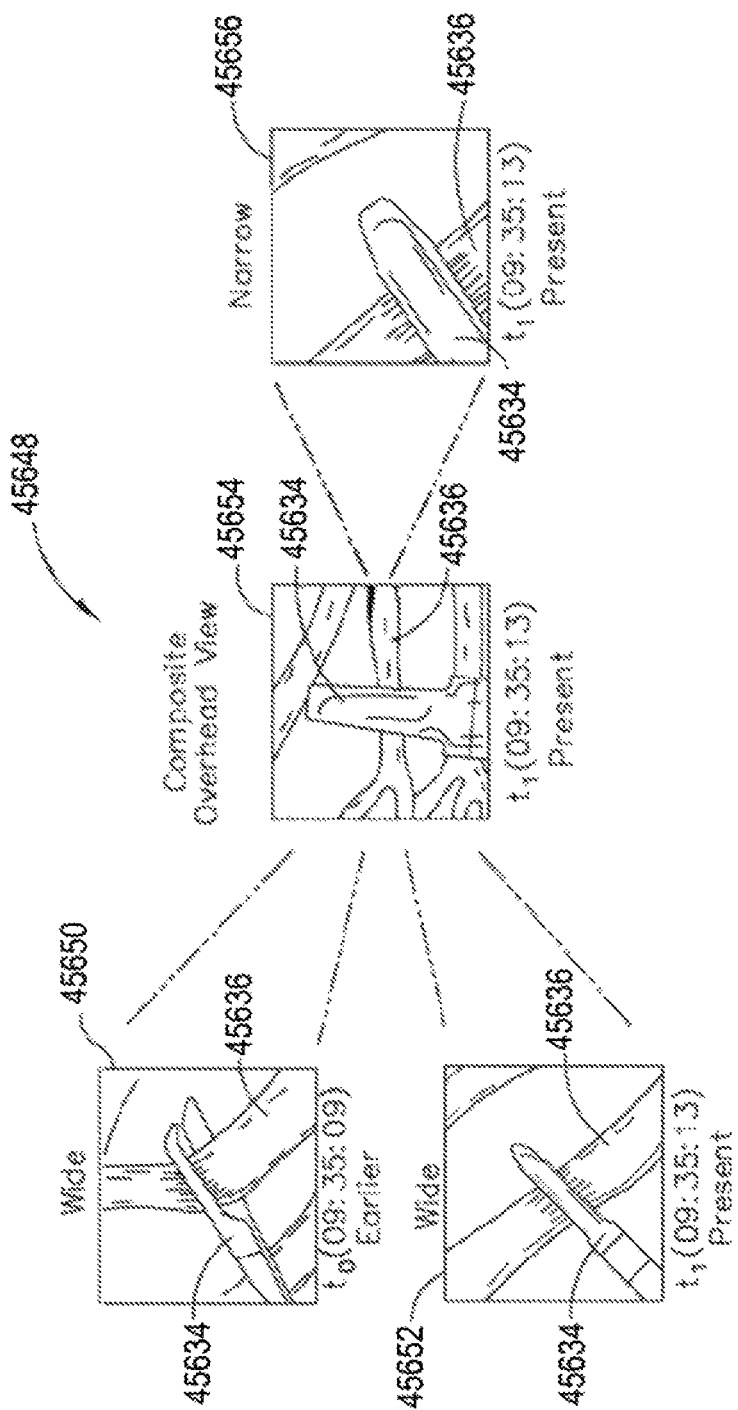
FIG. 11 illustrates a diagram of four wide angle view images of a surgical site at four separate times during the procedure.

FIG. 11 illustrates a diagram of four wide angle view images of a surgical site at four separate times during the procedure. For example, FIG. 11 illustrates a diagram 45648 of four separate wide-angle view images 45650, 45652, 45654, 45656 of a surgical site at four separate times during the procedure, according to an aspect of the present disclosure.

The sequence of images may show the creation of an overhead composite image in wide and narrow focus over time. A first image 45650 may be a wide-angle view of the end-effector 45634 clamping the vessel 45636 taken at an earlier time to (e.g., 09:35:09). A second image 45652 may be another wide-angle view of the end-effector 45634 clamping the vessel 45636 taken at the present time t1 (e.g., 09:35:13). A third image 45654 may be a composite image of an overhead view of the end-effector 45634 clamping the vessel 45636 taken at present time t1. The third image 45654 may be displayed in the second window 45638 of the primary display 45600 of the surgical hub 20006 as shown in FIG. 10. A fourth image 45656 may be a narrow angle view of the end-effector 45634 clamping the vessel 45636 at present time t1 (e.g., 09:35:13). The fourth image 45656 may be the narrow angle view of the surgical site shown in the primary window 45630 of the primary display 45600 of the surgical hub 20006 as shown in FIG. 10.

In an aspect of the present disclosure, the primary display and/or the secondary display may display one or more of the first image, the second image, the third image, and/or the fourth image. For example, the primary display may display the third image and the secondary display may display the fourth image. As another example, the primary display may display the fourth image and the second display may display the third image.

Figure 12:
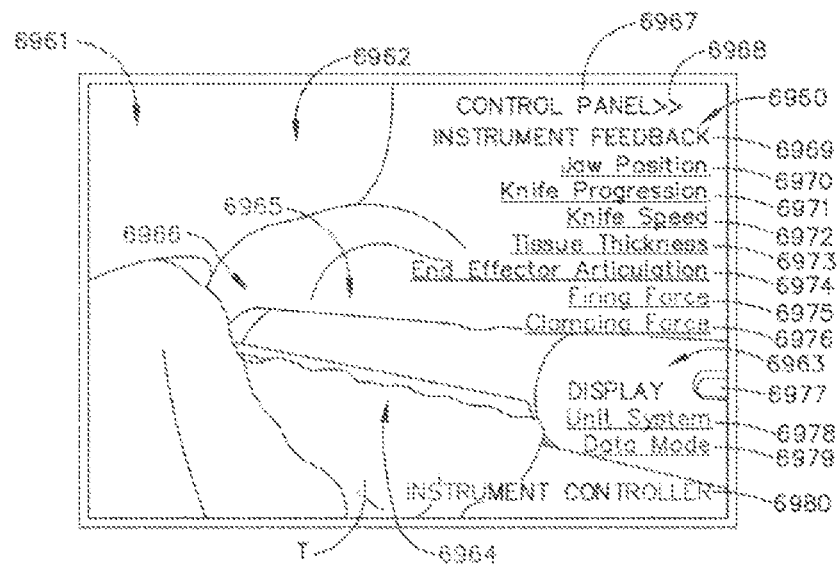
FIG. 12 illustrates a second layer of information overlaying a first layer of information, in accordance with at least one aspect of the present disclosure.

FIG. 12 illustrates a second layer of information overlaying a first layer of information, in accordance with at least one aspect of the present disclosure. For example, FIG. 12 illustrates a second layer of information overlaying a first layer of information. The second layer of information may include a symbolic representation of the knife overlapping the detected position of the knife in the disposable loading unit (DLU) depicted in the first layer of information. Further examples are disclosed in U.S. Pat. No. 9,283,054, titled SURGICAL APPARATUS WITH INDICATOR, which issued on Mar. 15, 2016, which is herein incorporated by reference in its entirety.

As described herein, a display may be referred to as a primary display, a secondary display, a monitor, a surgical hub display, an OR display, a room display, a surgical instrument display, a wearable display, and/or the like.

Referring to FIG. 12, the second layer of information 6963 may overlay at least a portion of the first layer of information 6962 on the display 6960. Furthermore, the touch screen 6961, which may be a primary display and/or a secondary display, may allow a user to manipulate the second layer of information 6963 relative to the video feedback in the underlying first layer of information 6962 on the display 6960. For example, a user may operate the touch screen 6961 to select, manipulate, reformat, resize, and/or otherwise modify the information displayed in the second layer of information 6963. In an aspect, the user may move the first layer of information and/or the second layer of information to one or more displays that may include a primary display and/or a secondary display. In an aspect, the user may use the touch screen 6961 to manipulate the second layer of information 6963 relative to the surgical instrument 6964 depicted in the first layer of information 6962 on the display 6960. A user may select a menu, category and/or classification of the control panel 6967 thereof, for example, and the second layer of information 6963 and/or the control panel 6967 may be adjusted to reflect the user's selection. In various aspects, a user may select a category from the instrument feedback menu 6969 that corresponds to a specific feature or features of the surgical instrument 6964 depicted in the first layer of information 6962. Feedback corresponding to the user-selected category may move, locate itself, and/or "snap" to a position on the display 6960 relative to the specific feature or features of the surgical instrument 6964. For example, the selected feedback may move to a position near and/or overlapping the specific feature or features of the surgical instrument 6964 depicted in the first layer of information 6962.

The instrument feedback menu 6969 may include a plurality of feedback categories, and may relate to the feedback data measured and/or detected by the surgical instrument 6964 during a surgical procedure. As described herein, the surgical instrument 6964 may detect and/or measure the position 6970 of a moveable jaw between an open orientation and a closed orientation, the thickness 6973 of clamped tissue, the clamping force 6976 on the clamped tissue, the articulation 6974 of the disposable loading unit (DLU) 6965, and/or the position 6971, velocity 6972, and/or force 6975 of the firing element, for example. Furthermore, the feedback controller in signal communication with the surgical instrument 6964 may provide the sensed feedback to the display 6960, which may display the feedback in the second layer of information 6963. As described herein, the selection, placement, and/or form of the feedback data displayed in the second layer of information 6963 may be modified based on the user's input to the touch screen 6961, for example.

When the knife of the DLU 6965 is blocked from view by the end effector jaws 6966 and/or tissue T, for example, the operator may track and/or approximate the position of the knife in the DLU 6965 based on the changing value of the feedback data and/or the shifting position of the feedback data relative to the DLU 6965 depicted in the underlying first layer of information 6962.

In various aspects, the display menu 6977 of the control panel 6967 may relate to a plurality of categories, such as unit systems (e.g., unit systems category) 6978 and/or data modes (e.g., data mode category) 6979, for example. In certain aspects, a user may select the unit systems category 6978 to switch between unit systems, such as between metric and U.S. customary units, for example. Additionally, a user may select the data mode category 6979 to switch between types of numerical representations of the feedback data and/or types of graphical representations of the feedback data, for example. The numerical representations of the feedback data may be displayed as numerical values and/or percentages, for example. Furthermore, the graphical representations of the feedback data may be displayed as a function of time and/or distance, for example. As described herein, a user may select the instrument controller menu 6980 from the control panel 6967 to input directives for the surgical instrument 6964, which may be implemented via the instrument controller and/or the microcontroller, for example. A user may minimize or collapse the control panel 6967 by selecting the minimize/maximize icon 6968, and may maximize or un-collapse the control panel 6967 by re-selecting the minimize/maximize icon 6968.

Figure 13:
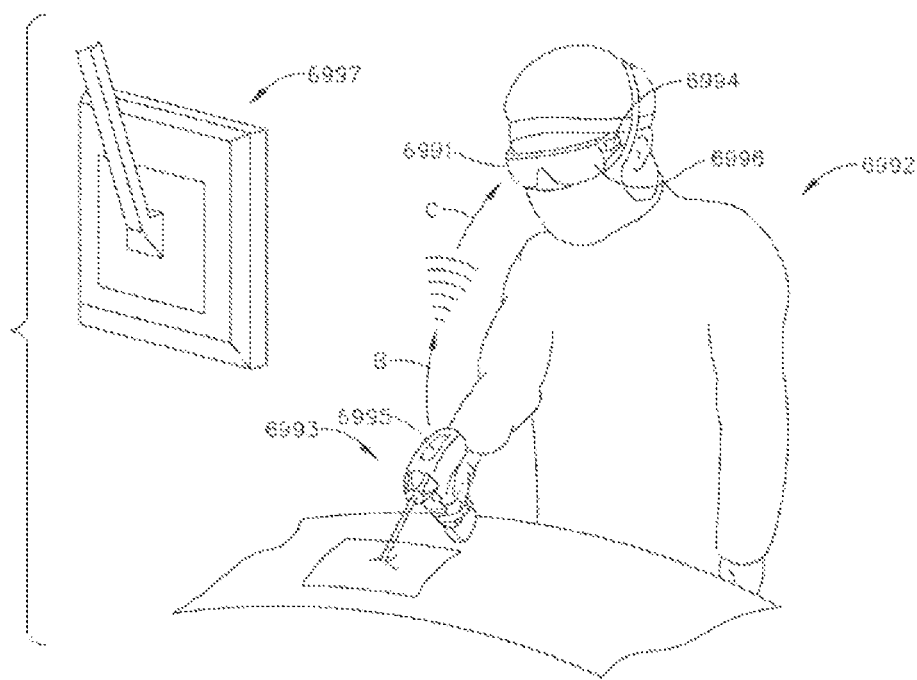
FIG. 13 depicts a perspective view of a surgeon using a surgical instrument that includes a handle assembly housing and a wireless circuit board during a surgical procedure, with the surgeon wearing a set of safety glasses, in accordance with at least one aspect of the present disclosure.

FIG. 13 depicts a perspective view of a surgeon using a surgical instrument that includes a handle assembly housing and a wireless circuit board during a surgical procedure, with the surgeon wearing a set of safety glasses, in accordance with at least one aspect of the present disclosure. The wireless circuit board may transmit a signal to a set of safety glasses worn by a surgeon using the surgical instrument during a procedure. The signal may be received by a wireless port on the safety glasses. One or more lighting devices on a front lens of the safety glasses may change color, fade, or glow in response to the received signal to indicate information to the surgeon about the status of the surgical instrument. The lighting devices are disposable on peripheral edges of the front lens to not distract the direct line of vision of the surgeon. Further examples are disclosed in U.S. Pat. No. 9,011,427, titled SURGICAL INSTRUMENT WITH SAFETY GLASSES, which issued on Apr. 21, 2015, which is herein incorporated by reference in its entirety.

FIG. 13 shows a version of safety glasses 6991 that may be worn by a surgeon 6992 during a surgical procedure while using a medical device. The safety glasses 6991 may include a primary display and/or a secondary display. The safety glasses 6991 may be used to determine a direction in which the surgeon 6992 is looking. For example, the safety glasses 6991 may analyze the pupil movements of the surgeon 6992 (e.g., using an internal or external camera) and may determine that the surgeon is viewing the monitor 6997. As another example, the safety glasses 6991 may use one or more sensors to track the head movement of the surgeon to determine where the surgeon is viewing (e.g., the surgeon is viewing the monitor 6997).

In use, a wireless communications board housed in a surgical instrument 6993 may communicate with a wireless port 6994 on safety glasses 6991. Exemplary surgical instrument 6993 is a battery-operated device, though instrument 6993 may be powered by a cable or otherwise. Instrument 6993 includes an end effector. Particularly, wireless communications board 6995 may transmit one or more wireless signals indicated by arrows (B, C) to wireless port 6994 of safety glasses 6991. Safety glasses 6991 may receive the signal, analyze the received signal, and display indicated status information received by the signal on lenses 6996 to a user, such as surgeon 6992, wearing safety glasses 6991.

Wireless communications board 6995 may transmit a wireless signal to a surgical monitor 6997 such that the surgical monitor 6997 may display received indicated status information to a surgeon 6992, as described herein. Surgical monitor 6997 may be a primary display or a secondary display.

A version of the safety glasses 6991 may include a lighting device on peripheral edges of the safety glasses 6991. A lighting device may provide peripheral-vision sensory feedback of instrument 6993, with which the safety glasses 6991 communicate to a user wearing the safety glasses 6991. The lighting device may be, for example, a light-emitted diode ("LED"), a series of LEDs, or any other suitable lighting device known to those of ordinary skill in the art and apparent in view of the teachings herein.

LEDs may be located at edges or sides of a front lens of the safety glasses 6991 so not to distract from a user's center of vision while still being positioned within the user's field of view such that the user does not need to look away from the surgical site to see the lighting device. Displayed lights may pulse and/or change color to communicate to the wearer of the safety glasses 6991 various aspects of information retrieved from instrument 6993, such as system status information or tissue sensing information (i.e., whether the end effector has sufficiently severed and sealed tissue). Feedback from housed wireless communications board 6995 may cause a lighting device to activate, blink, or change color to indicate information about the use of instrument 6993 to a user. For example, a device may incorporate a feedback mechanism based on one or more sensed tissue parameters. In this case, a change in the device output(s) based on this feedback in sync with a tone change may submit a signal through wireless communications board 6995 to the safety glasses 6991 to trigger activation of the lighting device. Such described means of activation of the lighting device should not be considered limiting as other means of indicating status information of instrument 6993 to the user via the safety glasses 6991 are contemplated. Further, the safety glasses 6991 may be single-use or reusable eyewear. Button-cell power supplies such as button-cell batteries may be used to power wireless receivers and LEDs of versions of safety glasses 6991, which may also include a housed wireless board and tri-color LEDs. Such button-cell power supplies may provide a low-cost means of providing sensory feedback of information about instrument 6993 when in use to surgeon 6992 wearing safety glasses 6991.

A surgical hub that may provide coordination of device pairing in an operating room may be provided. One of the functions of the surgical hub 20006 is to pair (also referred to herein as "connect" or "couple") with other components of the surgical system 20002 to control, gather information from, or coordinate interactions between the components of the surgical system 20002. Since the operating rooms of a hospital are likely in close physical proximity to one another, a surgical hub 20006 of a surgical system 20002 may unknowingly pair with components of a surgical system 20002 in a neighboring operating room, which would significantly interfere with the functions of the surgical hub 20006. For example, the surgical hub 20006 may unintentionally activate a surgical instrument in a different operating room or retrieve record information from a different ongoing surgical procedure in a neighboring operating room.

Aspects of the present disclosure present a surgical hub 20006 that may pair with detected devices of the surgical system 20002 that are located within the bounds of its operating room. The surgical hub 20006 may avoid incorrectly pairing with devices in another operating room.

Furthermore, the surgical hub 20006 may rely on its knowledge of the location of other components of the surgical system 20002 within its operating room in making decisions about, for example, which surgical instruments should be paired with one another or activated. A change in the position of the surgical hub 20006 or another component of the surgical system 20002 may be problematic.

Aspects of the present disclosure further present a surgical hub 20006 that may be configured to reevaluate or redetermine the bounds of its operating room upon detecting that the surgical hub 20006 has been moved.

Aspects of the present disclosure further present a surgical hub 20006 that may be configured to redetermine the bounds of its operating room upon detection of a potential device of the surgical system 20002, which may be an indication that the surgical hub 20006 has been moved.

In various aspects, a surgical hub 20006 may be used with a surgical system 20002 in a surgical procedure performed in an operating room. The surgical hub 20006 may comprise a control circuit configured to determine the bounds of the operating room, determine devices of the surgical system 20002 located within the bounds of the operating room, and pair the surgical hub 20006 with the devices of the surgical system 20002 located within the bounds of the operating room.

In an aspect, the control circuit may be configured to determine the bounds of the operating room after activation of the surgical hub 20006. In one aspect, the surgical hub 20006 may include a communication circuit configured to detect and pair with the devices of the surgical system located within the bounds of the operating room. In an aspect, the control circuit may be configured to redetermine the bounds of the operating room after a potential device of the surgical system 20002 is detected. In one aspect, the control circuit may be configured to periodically determine the bounds of the operating room.

In an aspect, the surgical hub 20006 may comprise an operating room mapping circuit that includes a plurality of non-contact sensors configured to measure the bounds of the operating room.

In various aspects, the surgical hub 20006 may include a processor and a memory coupled to the processor. The memory may store instructions executable by the processor to pair the surgical hub with devices of the surgical system 20002 located within the bounds of the operating room, as described above. In various aspects, the present disclosure may provide a non-transitory computer-readable medium storing computer-readable instructions which, when executed, cause a machine to pair the surgical hub 20006 with devices of the surgical system 20002 located within the bounds of the operating room, as described herein.

Figure 15:
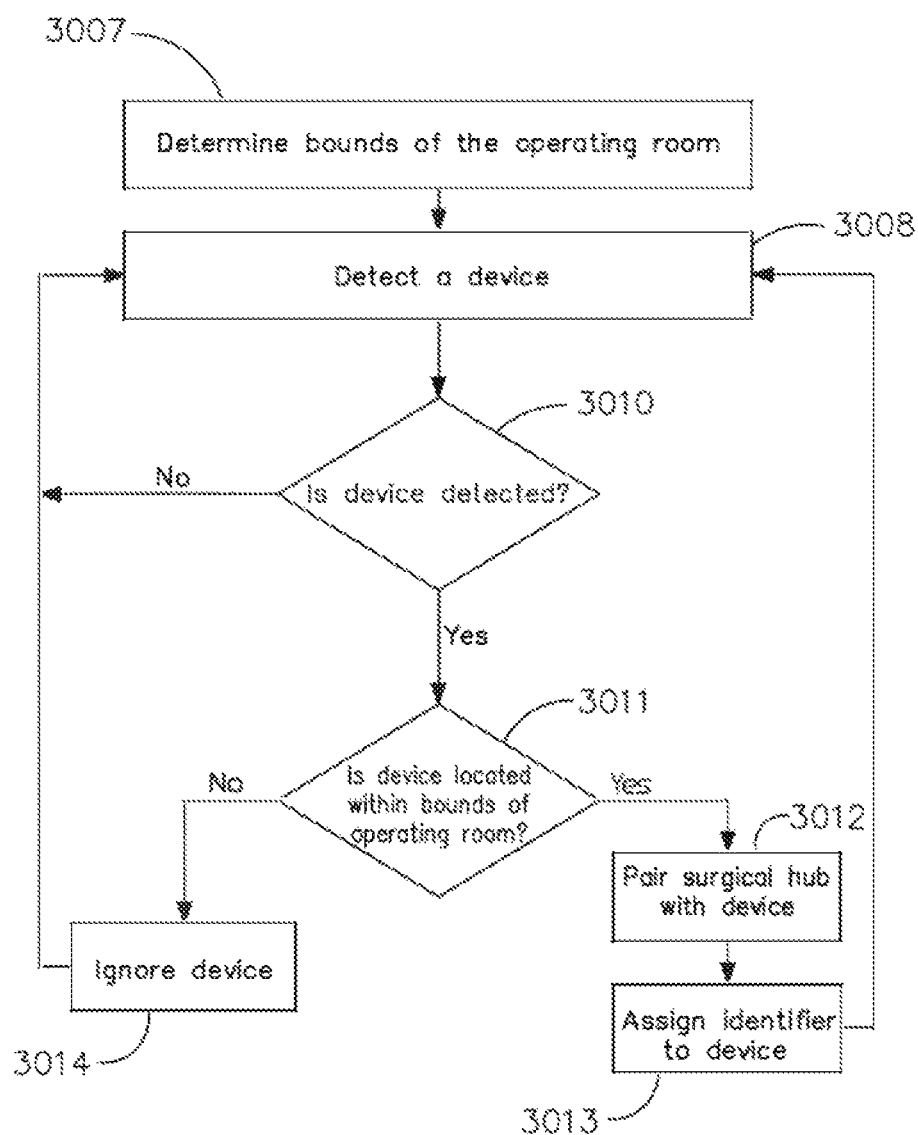
FIG. 15 is a logic flow diagram of a process depicting a control program or a logic configuration for surgical hub pairing with surgical devices of a surgical system that are located within the bounds of an operating room, in accordance with at least one aspect of the present disclosure.
Figure 16:
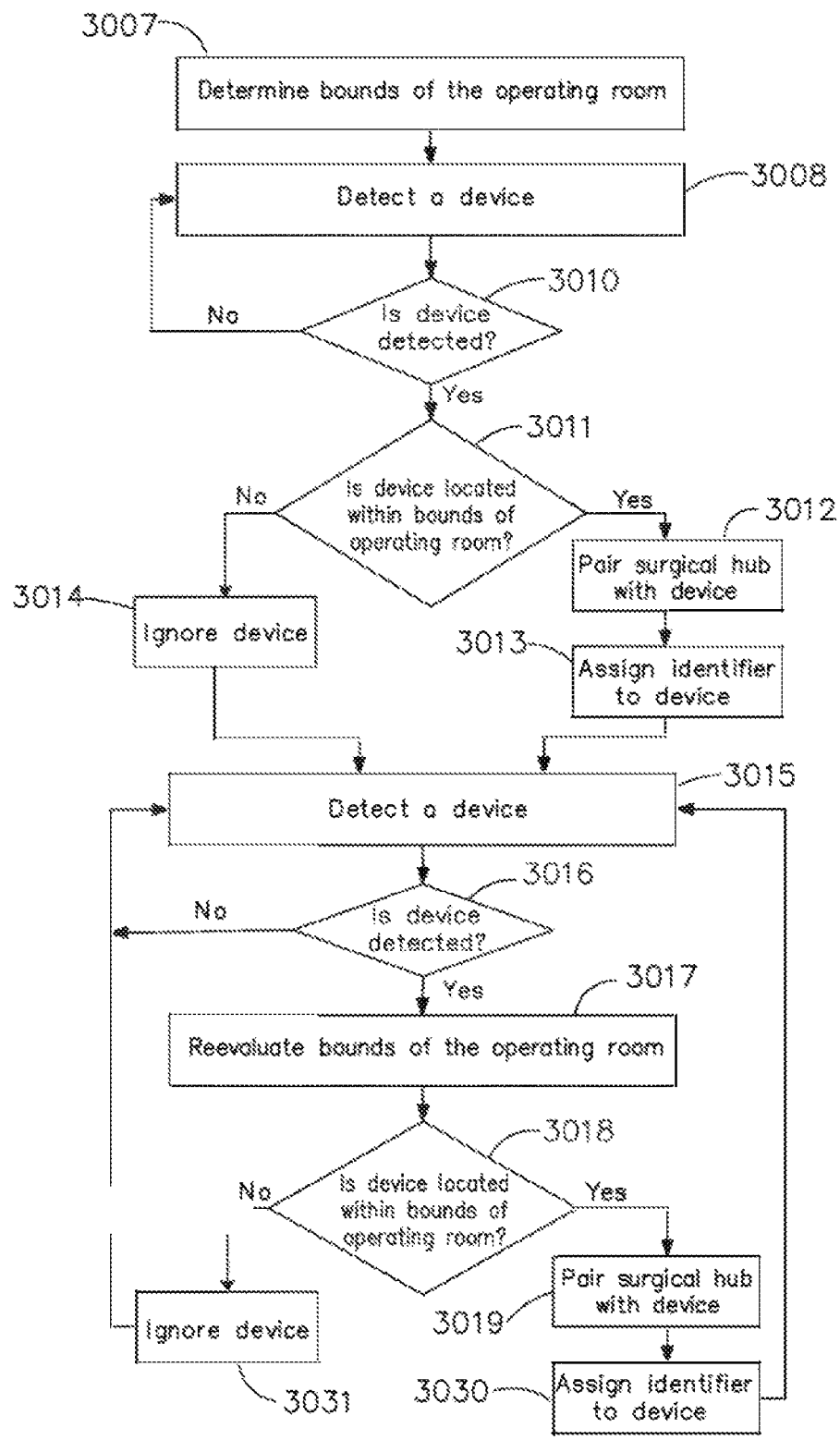
FIG. 16 is a logic flow diagram of a process depicting a control program or a logic configuration for selectively forming and severing connections between devices of a surgical system, in accordance with at least one aspect of the present disclosure.

FIGS. 15 and 16 are logic flow diagrams of processes depicting control programs or logic configurations for pairing the surgical hub 20006 with devices of the surgical system 20002 located within the bounds of the operating room, as described herein. FIG. 15 is a logic flow diagram of a process depicting a control program or a logic configuration for surgical hub pairing with surgical devices of a surgical system that are located within the bounds of an operating room, in accordance with at least one aspect of the present disclosure. FIG. 16 is a logic flow diagram of a process depicting a control program or a logic configuration for selectively forming and severing connections between devices of a surgical system, in accordance with at least one aspect of the present disclosure.

The surgical hub 20006 may perform a wide range of functions that may use short-range and long-range communication, such as assisting in a surgical procedure, coordinating between devices of the surgical system 20002, and gathering and transmitting data to the cloud. To perform its functions, the surgical hub 20006 may be equipped with a communication module capable of short-range communication with other devices of the surgical system 20002. The communication module may also be capable of long-range communication with the cloud.

The surgical hub 20006 may also be equipped with an operating room mapping module which may be capable of identifying the bounds of an operating room, and identifying devices of the surgical system 20002 within the operating room. The surgical hub 20006 may be configured to identify the bounds of an operating room, and may pair (e.g., may only pair) with or connect to potential devices of the surgical system 20002 that are detected within the operating room.

In an aspect, the pairing may comprise establishing a communication link or pathway. In another aspect, the pairing may comprise establishing a control link or pathway.

Figure 17:
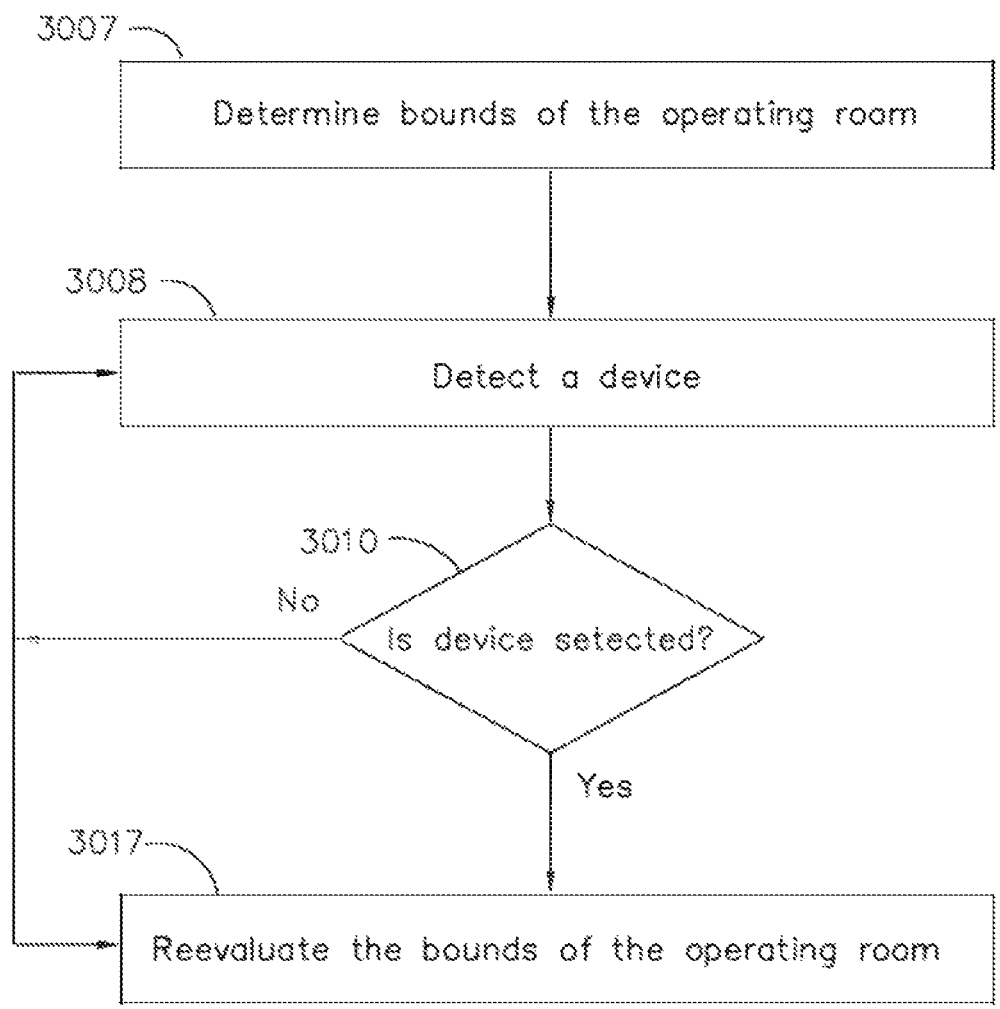
FIG. 17 is a logic flow diagram of a process depicting a control program or a logic configuration for selectively reevaluating the bounds of an operating room after detecting a new device, in accordance with at least one aspect of the present disclosure.
Figure 18:
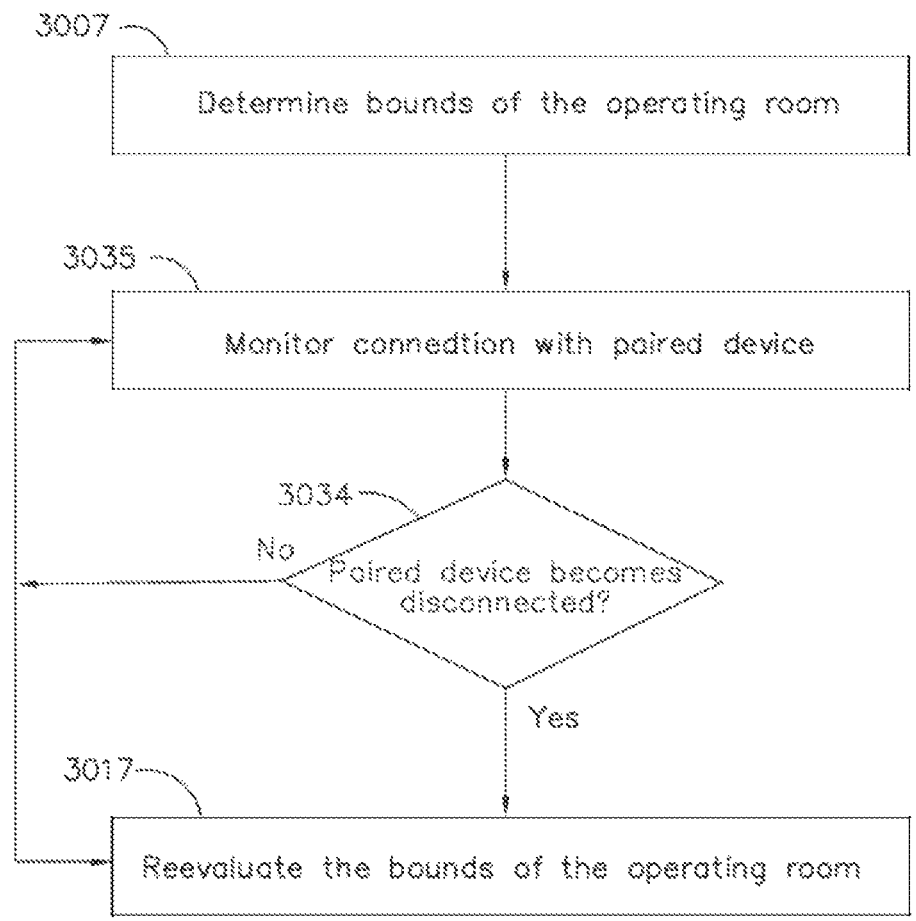
FIG. 18 is a logic flow diagram of a process depicting a control program or a logic configuration for selectively reevaluating the bounds of an operating room after disconnection of a paired device, in accordance with at least one aspect of the present disclosure.
Figure 19:
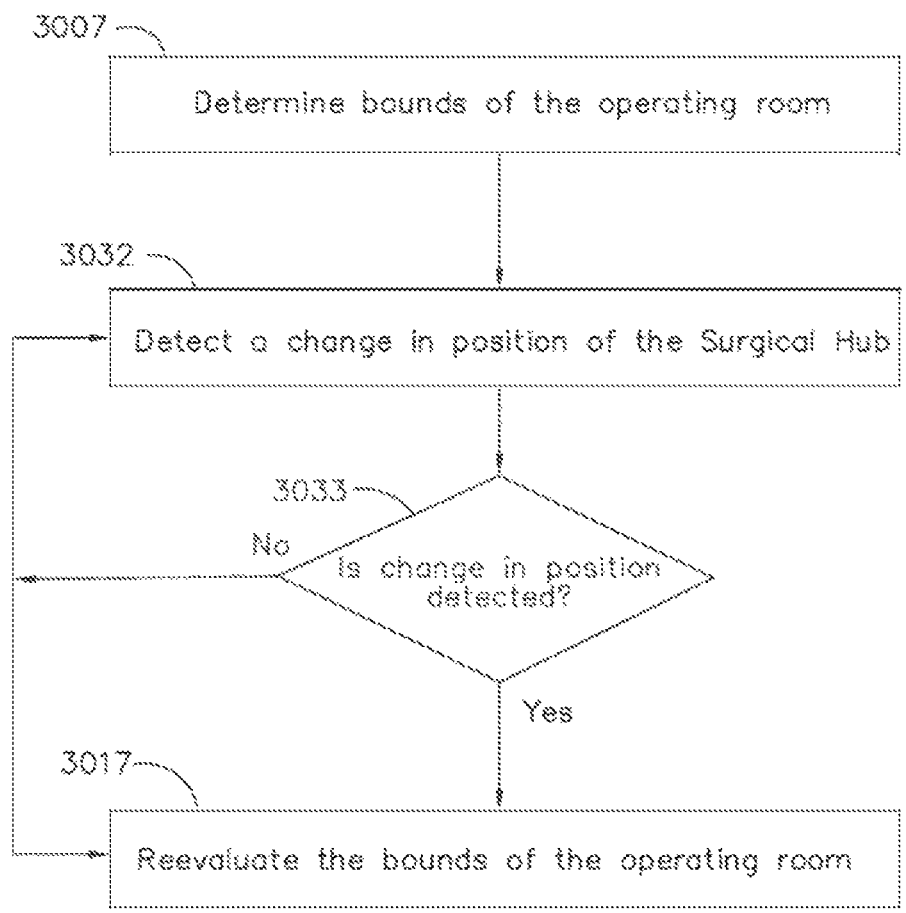
FIG. 19 is a logic flow diagram of a process depicting a control program or a logic configuration for reevaluating the bounds of an operating room by a surgical hub after detecting a change in the position of the surgical hub, in accordance with at least one aspect of the present disclosure.

A mapping or evaluation of the bounds of the operating room may take place during an activation (e.g., initial activation) of the surgical hub 20006. The surgical hub 20006 may be configured to maintain spatial awareness during operation by periodically mapping its operating room, which may be helpful in determining if the surgical hub 20006 has been moved. The reevaluation 3017 may be performed periodically or it may be triggered by an event such as observing a change in the devices of the surgical system 20002 that are deemed within the operating room. In an aspect, the change is detection 3010 of a device (e.g., a new device) that was not previously deemed as within the bounds of the operating room, as illustrated in FIG. 17. FIG. 17 is a logic flow diagram of a process depicting a control program or a logic configuration for selectively reevaluating the bounds of an operating room after detecting a new device, in accordance with at least one aspect of the present disclosure. In another aspect, the change may be a disappearance, disconnection, or un-pairing of a paired device that was previously deemed as residing within the operating room, as illustrated in FIG. 18. FIG. 18 is a logic flow diagram of a process depicting a control program or a logic configuration for selectively reevaluating the bounds of an operating room after disconnection of a paired device, in accordance with at least one aspect of the present disclosure. The surgical system 20006 may continuously monitor 3035 the connection with paired devices to detect 3034 the disappearance, disconnection, or un-pairing of a paired device.

In other aspects, reevaluation triggering events may be, for example, changes in surgeons' positions, instrument exchanges, or sensing of a new set of tasks being performed by the surgical system 20006.

In one aspect, the evaluation of the bounds of the room by the surgical system 20006 is accomplished by activation of a sensor array of the operating-room mapping module within the surgical system 20006 which enables it to detect the walls of the operating room.

Other components of the surgical system 20002 may be made to be spatially aware in the same, or a similar, manner as the surgical hub 20006. For example, a robotic hub may also be equipped with an operating room mapping module. A primary display and/or a secondary display may also be equipped with an operating room mapping module.

The spatial awareness of the surgical hub 20006 and its ability to map an operating room for potential components of the surgical system 20002 may allow the surgical hub 20006 to make autonomous decisions about whether to include or exclude such potential components as part of the surgical system 20002, which may relieve the surgical staff from dealing with such tasks. Furthermore, the surgical hub 20006 may be configured to make inferences about, for example, the type of surgical procedure to be performed in the operating room based on information gathered prior to, during, and/or after the performance of the surgical procedure. Examples of gathered information include the types of devices that are brought into the operating room, time of introduction of such devices into the operating room, and/or the devices sequence of activation. The spatial awareness of the surgical hub 20006 may also be used to update one of more displays within an operating room. For example, the spatial awareness of the surgical hub 20006 may display data on a primary display, may display data on a secondary display, and/or may move data between the primary display and secondary display based on at least one of a detection of an instrument, a mapping of the operating room, a detection of a user, a change in a location of the surgical hub, a disconnection of an instrument, and the like.

In one aspect, the surgical hub 20006 may employ the operating-room mapping module to determine the bounds of the surgical theater (e.g., a fixed, mobile, or temporary operating room or space) using ultrasonic or laser non-contact measurement devices.

Figure 14:
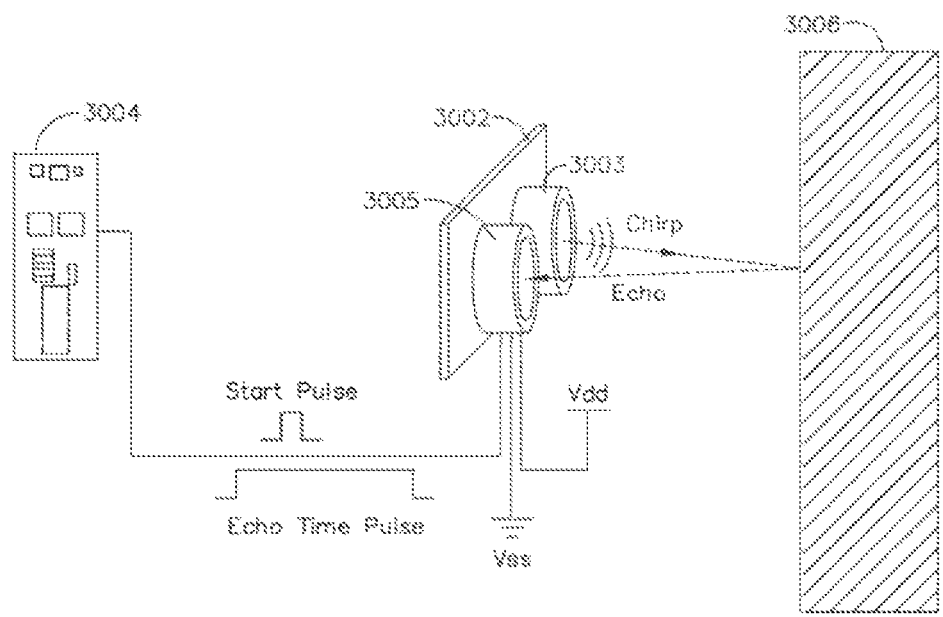
FIG. 14 illustrates ultrasonic pinging of an operating room wall to determine a distance between a surgical hub and the operating room wall, in accordance with at least one aspect of the present disclosure.

Referring to FIG. 14, ultrasound based non-contact sensors 3002 may be employed to scan the operating theater by transmitting a burst of ultrasound and receiving the echo when the ultrasound bounces off a perimeter wall 3006 of an operating theater to determine the size of the operating theater and to adjust Bluetooth pairing distance limits. In one example, the non-contact sensors (e.g., ultrasound based non-contact sensors) 3002 may be ping ultrasonic distance sensors, as illustrated in FIG. 14.

FIG. 14 illustrates ultrasonic pinging of an operating room wall to determine a distance between a surgical hub and the operating room wall, in accordance with at least one aspect of the present disclosure.

FIG. 14 shows how an ultrasonic sensor 3002 sends a brief chirp with its ultrasonic speaker 3003 and makes it possible for a micro-controller 3004 of the operating-room mapping module to measure how long the echo takes to return to the ultrasonic sensor's ultrasonic microphone 3005. The micro-controller 3004 may send the ultrasonic sensor 3002 a pulse to begin the measurement. The ultrasonic sensor 3002 then may wait long enough for the micro-controller program to start a pulse input command. Then, at about the same time the ultrasonic sensor 3002 chirps a 40 kHz tone, the ultrasonic sensor may send a high signal to the micro-controller 3004. When the ultrasonic sensor 3002 detects the echo with its ultrasonic microphone 3005, it may change that high signal back to low. The micro-controller's pulse input command may measure the time between the high and low changes and may store its measurement in a variable. This value may be used along with the speed of sound in air to calculate the distance between the surgical hub 20006 and the operating-room wall (e.g., operating room perimeter wall) 3006.

In an example, as illustrated in FIG. 14, a surgical hub 20006 may be equipped with four ultrasonic sensors 3002, wherein each of the four ultrasonic sensors is configured to assess the distance between the surgical hub 20006 and a wall of the operating room 3000. A surgical hub 20006 may be equipped with more or less than four ultrasonic sensors 3002 to determine the bounds of an operating room.

Other distance sensors may be employed by the operating-room mapping module to determine the bounds of an operating room. In an example, the operating-room mapping module may be equipped with one or more photoelectric sensors that may be employed to assess the bounds of an operating room. In one example, suitable laser distance sensors may also be employed to assess the bounds of an operating room. Laser-based non-contact sensors may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits.

Figure 22:
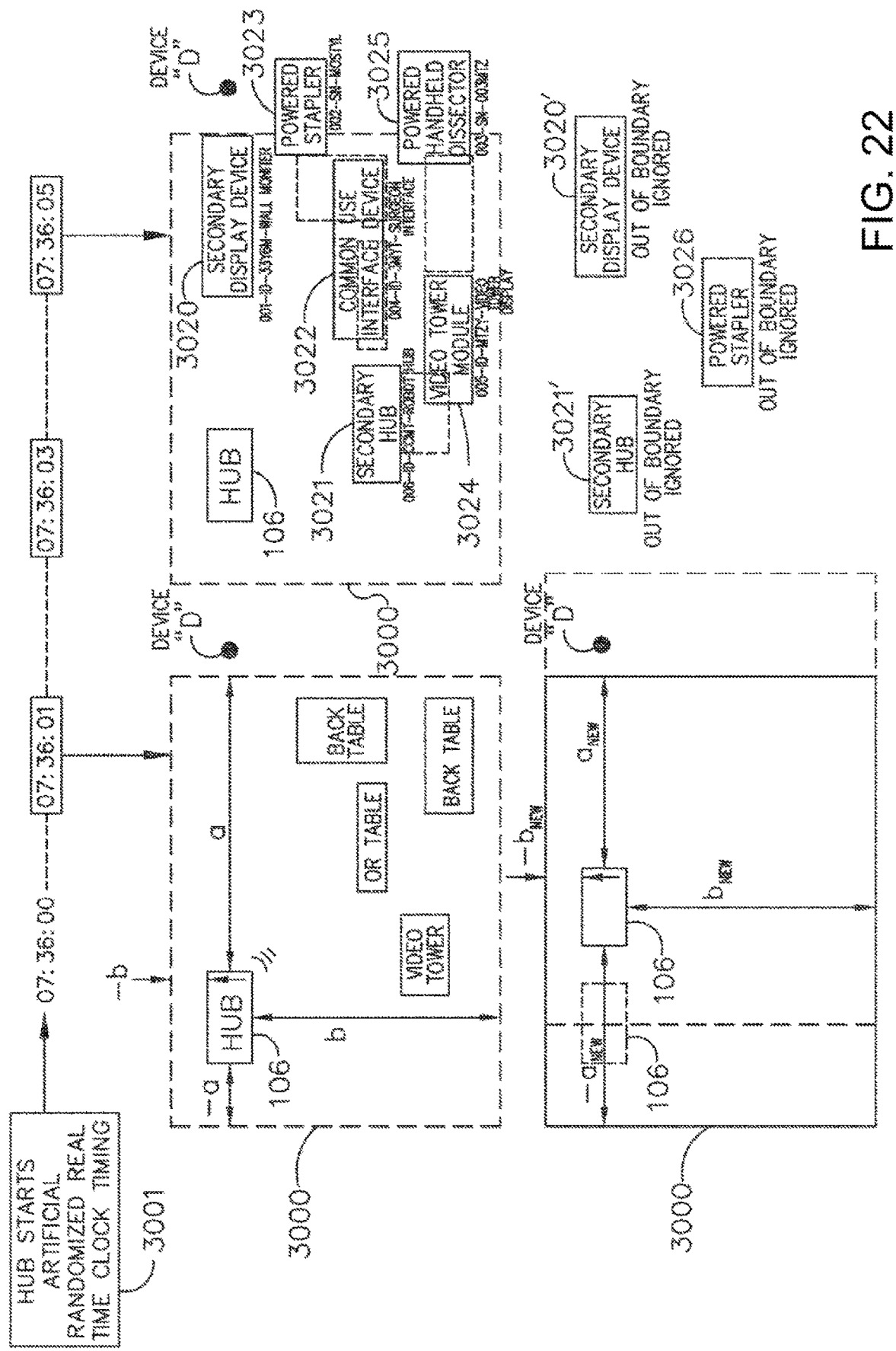
FIG. 22 illustrates a partial artificial timeline of a surgical procedure performed in an operating room via a surgical system, in accordance with at least one aspect of the present disclosure.

FIG. 22 illustrates a partial artificial timeline of a surgical procedure performed in an operating room via a surgical system, in accordance with at least one aspect of the present disclosure.

Referring to the top left corner of FIG. 22, a surgical hub 20006 may be brought into an operating room 3000. The surgical hub 20006 may be activated at the beginning of the set-up that occurs prior to the surgical procedure. In the example of FIG. 22, the set-up may start at an actual time of 11:31:14 (EST) based on a real-time clock. However, at the stated procedure set-up start time, the surgical hub 20006 may start 3001 an artificial randomized real-time clock timing scheme at artificial real time 07:36:00 to protect private patient information.

At artificial real time 07:36:01, the operating-room mapping module may employ the ultrasonic distance sensors to ultrasonically ping the room (e.g., sends out a burst of ultrasound and listens for the echo when it bounces off the perimeter walls of the operating room as described above) to verify the size of the operating room and to adjust pairing distance limits.

At artificial real time 07:36:03, the data may be stripped and time stamped. At artificial real time 07:36:05, the surgical hub 20006 may begin pairing devices located only within the operating room 3000 as verified using ultrasonic distance sensors 3002 of the operating-room mapping module. The top right corner of FIG. 22 illustrates several example devices that are within the bounds of the operating room 3000 and are paired with the surgical hub 20006, including a secondary display device 3020, a secondary hub 3021, a common interface device 3022, a powered stapler 3023, a video tower module 3024, and a powered handheld dissector 3025. On the other hand, secondary hub 3021', secondary display device 3020', and powered stapler 3026 are all outside the bounds of the operating room 3000 and, accordingly, are not paired with the surgical hub 20006.

In addition to establishing a communication link with the devices of the surgical system 20002 that are within the operating room, the surgical hub 20006 also may assign a unique identification and communication sequence or number to each of the devices. The unique sequence may include the device's name and a time stamp of when the communication was first established. Other suitable device information may also be incorporated into the unique sequence of the device.

As illustrated in the top left corner of FIG. 22, the surgical hub 20006 has determined that the operating room 3000 bounds are at distances a, −a, b, and −b from the surgical hub 20006. Since Device "D" is outside the determined bounds of its operating room 3000, the surgical hub 20006 may not pair with the Device "D."

FIG. 15 is an example algorithm illustrating how the surgical hub 20006 may pair (e.g., may only pair) with devices within the bounds of its operating room. After activation, the surgical hub 20006 may determine 3007 bounds of the operating room using the operating-room mapping module, as described herein. After the initial determination, the surgical hub 20006 may continuously search for or detect 3008 devices within a pairing range. If a device is detected 3010, the surgical hub 20006 may then determine 3011 whether the detected device is within the bounds of the operating room. The surgical hub 20006 may pair 3012 with the device if it is determined that the device is within the bounds of the operating room. The surgical hub 20006 may display data associated with the paired device on a primary display and/or a secondary display. In certain instances, the surgical hub 20006 may also assign 3013 an identifier to the device. If, however, the surgical hub 20006 determines that the detected device is outside the bounds of the operating room, the surgical hub 20006 may ignore 3014 the device.

Referring to FIG. 16, after an initial determination of the bounds of the room, and after an initial pairing of devices located within such bounds, the surgical hub 20006 may continue to detect 3015 new devices that become available for pairing. If a new device is detected 3016, the surgical hub 20006 may be configured to reevaluate 3017 the bounds of the operating room prior to pairing with the new device. If the new device is determined 3018 to be within the newly determined bounds of the operating room, then the surgical hub 20006 may pair with the device 3019 and assign 3030 a unique identifier to the new device. If, however, the surgical hub 20006 determines that the new device is outside the newly determined bounds of the operating room, the surgical hub 20006 may ignore 3031 the device.

For pairing, the operating-room mapping module may comprise a compass and integrated Bluetooth transceiver. Other communication mechanisms, which are not significantly affected by the hospital environment or geographical location, may be employed. Bluetooth Low Energy (BLE) beacon technology may currently achieve indoor distance measurements with accuracy of about 1-2 meters, with improved accuracy in closer proximities (within 0-6 meters). To improve the accuracy of the distance measurements, a compass may be used with the BLE. The operating-room mapping module may utilize the BLE and the compass to determine where modules are located in relation to the patient. For example, two modules facing each other (detected by compass) with greater than one meter distance between them may clearly indicate that the modules are on opposite sides of the patient. The more "Hub"-enabled modules that reside in the operating room, the greater the achievable accuracy may become due to triangulation techniques.

In the situations where multiple surgical hubs 20006, modules, and/or other peripherals are present in the same operating room, as illustrated in the top right corner of FIG. 22, the operating-room mapping module may be configured to map the physical location of each module that resides within the operating room. This information may be used by the user interface to display a virtual map of the room, enabling the user to more easily identify which modules are present and enabled, as well as their current status. In one aspect, the mapping data collected by surgical hubs 20006 may be uploaded to the cloud, where the data may be analyzed for identifying how an operating room is physically setup, for example.

The surgical hub 20006 may be configured to determine a device's location by assessing transmission radio signal strength and direction. For Bluetooth protocols, the Received Signal Strength Indication (RSSI) is a measurement of the received radio signal strength. In one aspect, the devices of the surgical system 20002 may be equipped with USB Bluetooth dongles. The surgical hub 20006 may scan the USB Bluetooth beacons to get distance information. In another aspect, multiple high-gain antennas on a Bluetooth access point with variable attenuators may produce more accurate results than RSSI measurements. In one aspect, the hub may be configured to determine the location of a device by measuring the signal strength from multiple antennas. Alternatively, in some examples, the surgical hub 20006 may be equipped with one or more motion sensor devices configured to detect a change in the position of the surgical hub 20006.

Referring to the bottom left corner of FIG. 22, the surgical hub 20006 has been moved from its original position, which is depicted in dashed lines, to a new position closer to the device "D," which is still outside the bounds of the operating room 3000. The surgical hub 20006 in its new position, and based on the previously determined bounds of the operating room, may naturally conclude that the device "D" is a potential component of the surgical system 20002. However, the introduction of a new device may be a triggering event for reevaluation 3017 of the bounds of the operating room, as illustrated in the example algorithm of FIGS. 15, 17. After performing the reevaluation, the surgical hub 20006 may determine that the operating room bounds have changed. Based on the new bounds, at distances anew, –a new, bnew, and –bnew, the surgical hub 20006 may conclude that it has been moved and that the Device "D" is outside the newly determined bounds of its operating room. Accordingly, the surgical hub 20006 may still not pair with the Device "D." The surgical hub 20006 may also update a primary display and/or a secondary display to reflect the change.

In one aspect, one or more of the processes depicted in FIGS. 15-19 may be executed by a control circuit of a surgical hub 20006. In another aspect, one or more of the processes depicted in FIGS. 15-19 may be executed by a cloud computing system 20008. In yet another aspect, one or more of the processes depicted in FIGS. 15-19 may be executed by at least one of the aforementioned cloud computing systems 20008 and/or a control circuit of a surgical hub 20006 in combination with a control circuit of a modular device, such as the microcontroller of a surgical instrument, the control circuit of a robotic surgical, the control circuit of the surgical instruments, and/or any other suitable microcontroller.

During a surgical procedure, a surgical instrument such as an ultrasonic or an RF surgical instrument may be coupled to a generator module 140 of the surgical hub 20006. In addition, a separate surgical instrument controller such as a controller that may be controlled by a foot, a hand, a switch, and/or another activation device may be used by an operator of the surgical instrument to activate the energy flow from the generator to the surgical instrument. Multiple surgical instrument controllers and multiple surgical instruments may be used concurrently in an operating room. Pressing or activating the wrong surgical instrument controller may lead to undesirable consequences. Aspects of the present disclosure present a solution in which the surgical hub 20006 coordinates the pairing of surgical instrument controllers and surgical instruments to ensure patient and operator safety.

Aspects of the present disclosure are presented for a surgical hub 20006 configured to establish and sever pairings between components of the surgical system 20002 within the bounds of the operating room to coordinate flow of information and control actions between such components. The surgical hub 20006 may be configured to establish a pairing between a surgical instrument controller and a surgical instrument that resides within the bounds of an operating room of surgical hub 20006.

In various aspects, the surgical hub 20006 may be configured to establish and sever pairings between components of the surgical system 20002 based on operator request(s) or situational and/or spatial awareness.

Figure 20:
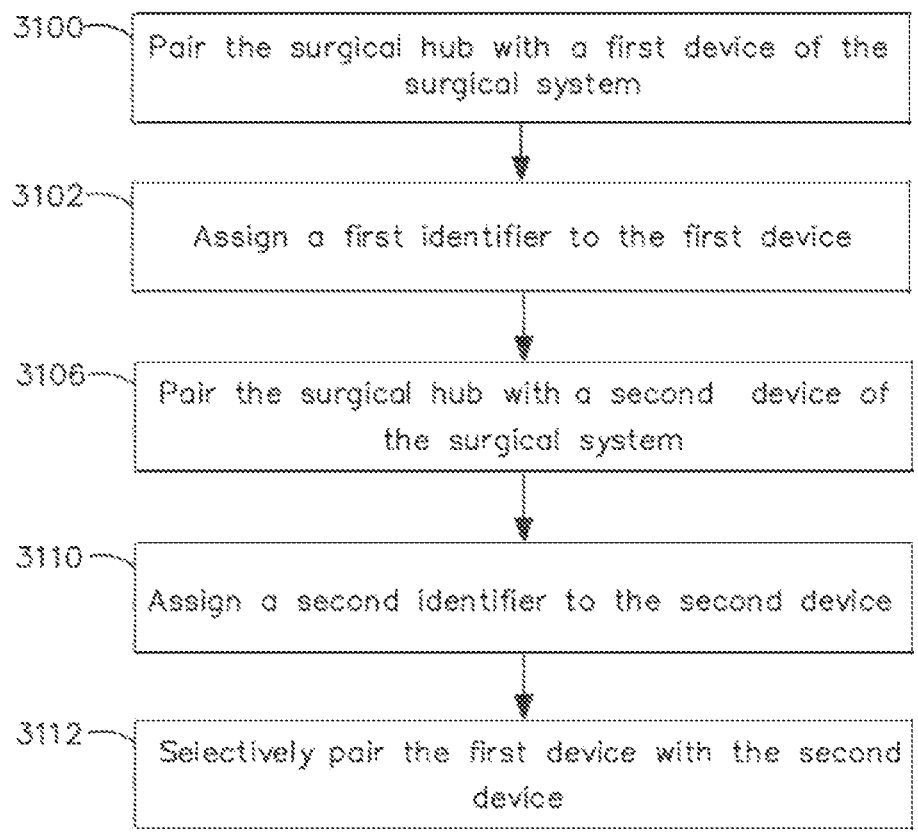
FIG. 20 is a logic flow diagram of a process depicting a control program or a logic configuration for selectively forming connections between devices of a surgical system, in accordance with at least one aspect of the present disclosure.

Aspects of the present disclosure are presented for a surgical hub for use with a surgical system in a surgical procedure performed in an operating room. The surgical hub may include a control circuit that selectively forms and severs pairings between devices of the surgical system. The surgical hub may update a primary display and/or a secondary display to reflect formed or severed pairings. In one aspect, such as shown in FIG. 20, the hub may include a control circuit that is configured to pair the hub with a first device of the surgical system at 3100, may assign a first identifier to the first device at 3102, may pair the hub with a second device of the surgical system at 3106, may assign a second identifier to the second device at 3112, and/or may selectively pair the first device with the second device at 3112. In one aspect, the surgical hub may include a storage medium, wherein the control circuit is configured to store a record indicative of the pairing between the first device and the second device in the storage medium. In one aspect, the pairing between the first device and the second device may define a communication pathway therebetween. In one aspect, the pairing between the first device and the second device may define a control pathway for transmitting control actions from the second device to the first device.

Figure 21:
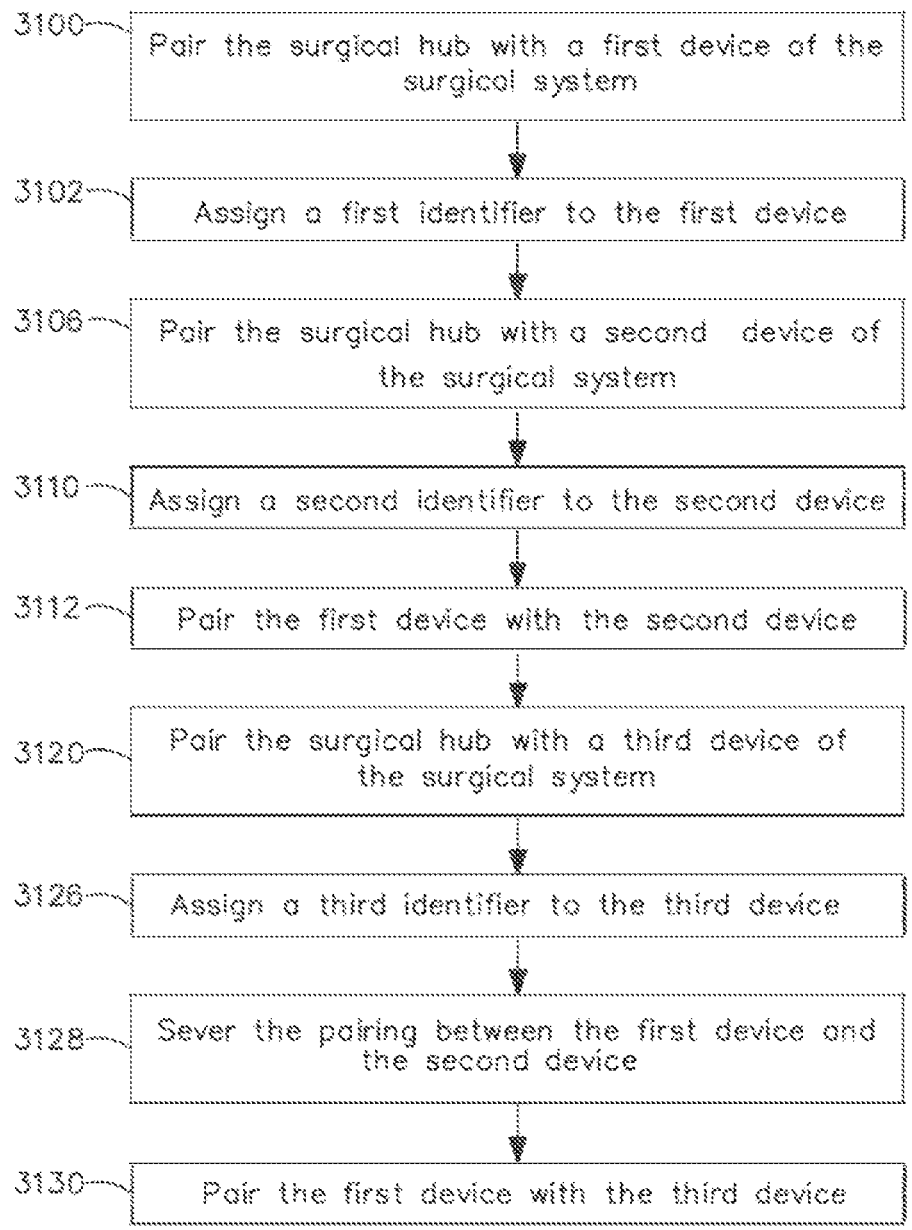
FIG. 21 is a logic flow diagram of a process depicting a control program or a logic configuration for selectively forming and severing connections between devices of a surgical system, in accordance with at least one aspect of the present disclosure.

In an aspect, such as shown in FIG. 21, the control circuit may be further configured to pair the hub with a third device of the surgical system at 3120, assign a third identifier to the third device at 3125, sever the pairing between the first device and the second device at 3128, and/or selectively pair the first device with the third device at 3130. In one aspect, the control circuit may be further configured to store a record indicative of the pairing between the first device and the third device in the storage medium. In one aspect, the pairing between the first device and the third device may define a communication pathway therebetween. In one aspect, the pairing between the first device and the third device may define a control pathway for transmitting control actions from the third device to the first device.

In various aspects, the surgical hub may include a processor and a memory coupled to the processor. The memory may store instructions executable by the processor to selectively form and sever pairings between the devices of the surgical system, as described above. In various aspects, the present disclosure may provide a non-transitory computer-readable medium storing computer-readable instructions which, when executed, cause a machine to selectively form and sever pairings between the devices of the surgical system, as described above. FIGS. 20 and 21 are logic flow diagrams of processes depicting control programs or logic configurations for selectively forming and severing pairings between the devices of the surgical system, as described herein. FIG. 20 is a logic flow diagram of a process depicting a control program or a logic configuration for selectively forming connections between devices of a surgical system, in accordance with at least one aspect of the present disclosure. FIG. 21 is a logic flow diagram of a process depicting a control program or a logic configuration for selectively forming and severing connections between devices of a surgical system, in accordance with at least one aspect of the present disclosure.

In one aspect, the surgical hub 20006 may establish a first pairing with a surgical instrument and a second pairing with the surgical instrument controller. The surgical hub 20006 may then link the pairings together, allowing the surgical instrument and the surgical instrument controller to operate with one another. The surgical hub 20006 may update the display of a primary display and/or a secondary display to reflect the linked pairings. In another aspect, the surgical hub 20006 may sever an existing communication link between a surgical instrument and a surgical instrument controller, then may link the surgical instrument to another surgical instrument controller that is linked to the surgical hub 20006. The surgical hub 20006 may update the display of a primary display and/or a secondary display to reflect the severed communication link and/or the link to another surgical instrument controller.

In one aspect, the surgical instrument controller may be paired to two sources. The surgical instrument controller may be paired to the surgical hub 20006, which includes the generator module, for control of its activation. The surgical instrument controller may also be paired to a specific surgical instrument to prevent inadvertent activation of the wrong surgical instrument.

Referring to FIG. 20, the surgical hub 20006 may cause the communication module to pair 3100 or establish a first communication link 3101 with a first device 3102 of the surgical system 20002, which may be a first surgical instrument. Then, the hub may assign 3104 a first identification number to the first device 3102. This may be a unique identification and communication sequence or number that may include the device's name and a timestamp of when the communication was first established.

In addition, the surgical hub 20006 may then cause the communication module to pair 3106 or establish a second communication link 3107 with a second device 3108 of the surgical system 20002, which may be a surgical instrument controller. The surgical hub 20006 may then assign 3110 a second identification number to the second device 3108.

In various aspects, pairing a surgical hub 20006 with a device may include detecting the presence of a new device, determining that the new device is within bounds of the operating room, as described herein, and pairing (e.g., only pairing) with the new device if the new device is located within the bounds of the operating room.

Referring to FIG. 21, the surgical hub 20006 may detect and pair 3120 or establish a third communication link 3124 with a third device 3116 of the surgical system 20002, which may be another surgical instrument controller, for example. The surgical hub 20006 may then assign 3126 a third identification number to the third device 3116. The surgical hub 20006 may update a primary display and/or a secondary display to indicate that the third device has been detected and/or paired.

In one aspect, the computer systems may utilize video/images of the OR that are external to a surgical site (e.g., an abdomen of a patient undergoing a laparoscopic procedure). In this aspect, the camera assembly capturing the images for analysis by the computer system described herein may exclude or include images from a laparoscope, thoracoscope, or another such endoscope and/or video camera utilized for visualizing the interior of a patient's body. Rather, the camera assembly may include cameras positioned about the OR to visualize how the surgical devices are being utilized and how the surgical staff is interacting with each other and the surgical devices to provide a broader context for the actions that are occurring within the OR. In another aspect, the externally captured video/images may be utilized in conjunction with video/images from endoscopes for analysis and/or to improve the control of the surgical devices in use. Further examples are disclosed in U.S. Patent. Application Publication No. 2019-0201129 A1 (U.S. patent application Ser. No. 16/182,269), titled IMAGE CAPTURING OF THE AREAS OUTSIDE THE ABDOMEN TO IMPROVE PLACEMENT AND CONTROL OF A SURGICAL DEVICE IN USE, filed Nov. 6, 2018, which is herein incorporated by reference in its entirety.

Figure 23:
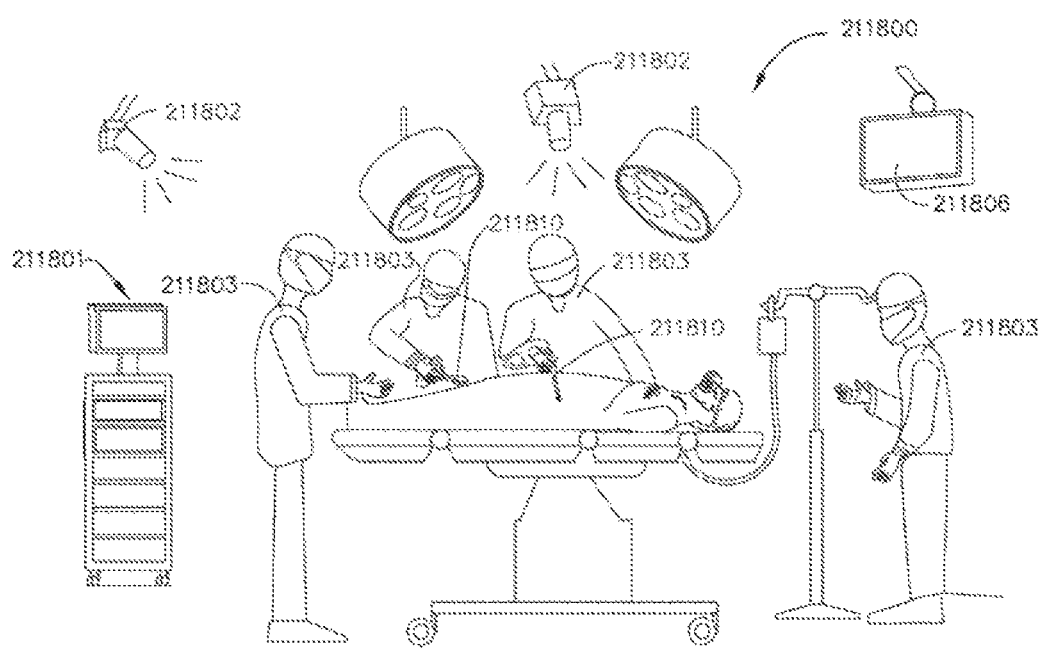
FIG. 23 is a diagram of an illustrative operating room (OR) setup, in accordance with at least one aspect of the present disclosure.

FIG. 23 is a diagram of an illustrative OR setup, in accordance with at least one aspect of the present disclosure. In various implementations, a surgical hub 211801 may be connected to one or more cameras 211802, surgical instruments 211810, displays 211806, overheard lights 211808, and other surgical devices within the OR 211800 via a communications protocol (e.g., Bluetooth), as described above under the heading SURGICAL HUBS. The cameras 211802 may be oriented in order to capture images and/or video of the surgical staff members 211803 and/or surgical instruments 211810 (or other surgical devices) within the OR 211800 during the course of a surgical procedure. The captured image(s) may include static images or moving images (i.e., video). The images of the surgical staff members 211803 and/or surgical instruments 211810 may be captured at a variety of angles and magnifications, utilize different filters, and so on. In one implementation, the cameras 211802 may be arranged within the OR 211800 so that they may collectively visualize each surgical staff member performing the procedure. Accordingly, the surgical hub 211801 may receive the captured image and/or video data from the cameras 211802 to visually analyze the surgical staff members 211803 and/or the surgical instruments 211810 during the surgical procedure. The image and/or video data may be processed utilizing a variety of machine vision, image processing, object recognition, and optical tracking techniques to track characteristics, properties, actions, and movements of the surgical staff members 211803 and/or the surgical instruments 211810.

An HCP may be a nurse, doctor, surgeon, medical technician, physician, and/or the like.

An augmented reality display may be a display that may be capable of overlaying one or more images. for example, a display may overlay a medical image over an image of a patient. In an example, a display may overlay a medical image over a video of a patient. In an example, display may overlay an indicator and or one or more instructions over an image. An augmented reality display may be a wearable device.

In examples, one or more surgical hubs may determine if an object is located (e.g., present) in the surgical operating room (OR). In examples, the surgical hub(s) may determine if an object is absent from the surgical OR. In examples, the surgical hub(s) may determine if the object is located in a room, such as a room that may be adjacent to the surgical OR. The surgical hubs may operate in concert or may operate independently. An object may be a smart device such as a smart medical instrument.

The surgical hub may use a ping (e.g., an ultrasonic ping), for example, to define the boundaries (e.g., walls) of the surgical OR. The surgical hub may be aware when objects enter or leave the surgical OR.

The surgical hub may be included in a tiered software system. The surgical hub may use spatial awareness, for example, when determining if objects are located in the surgical OR. Objects may register to the surgical hub. For example, objects may send respective identifications and/or serial numbers to the surgical hub. In examples, the surgical hub may track the objects' respective positions within the surgical OR. In examples, one or more cameras may be used to track the objects. The cameras may be in communication with the surgical hub.

In examples, the surgical hub may determine if an object is inside a patient and may indicate to remove the object. For example, a surgical hub may send a notification to a surgeon that the object is inside a patient and that the object may need to be removed. In examples, the surgical hub may track a spatial temporal component associated with each object. For example, the surgical hub may track which device is in a medical staff member's hand, for example, at a given time.

The surgical hub may overlay data on the object. For example, the object may be a medical instrument. A display may be configured for the overlaid data. The display may be included on the medical instrument. The display may be attachable to the medical instrument. The data may be depicted on the screen for a user to see. The cameras as described herein may observe a change in the surgical OR and may overlay data associated with the change to a medical instrument display.

The surgical hub may be aware of secondary objects located in a storage destination. The storage destination may be located outside the surgical OR. The surgical hub may determine when one or more secondary objects are involved in a surgery. In examples, the surgical hub may communicate to a medical staff member (e.g., a rotating nurse) to retrieve the secondary objects involved in the surgery.

The surgical hub may pinpoint an object (e.g., each object) located in the surgical OR. In examples, the surgical hub may be aware of an instrument involved in a surgery. For example, the instrument may be involved in an upcoming surgical task of the surgery. A display may be accessible to a table nurse and may be in communication with the surgical hub. The surgical hub may indicate the instrument involved in the surgery on the display. For example, the surgical hub may highlight the instrument on the display. The instrument involved in the surgery may be located in a storage destination as described herein. The surgical hub may indicate the storage destination that the instrument is located at.

Augmented reality may be used by the surgical hub to indicate the instrument. For example, the augmented reality may be associated with a secondary display overlay on another display. The surgical hub may use augmented reality to highlight the instrument involved in the surgery. The cameras as described herein may record data (e.g., metadata) associated with orientations and/or configurations of instruments. An augmented reality display may show information related to the metadata associated with each instrument. For example, an augmented reality display may be a pair of visualization glasses. The augmented reality display may show steps for a medical staff to perform. Each medical staff member may access an individual augmented reality display, for example, to see personalized steps that the medical staff has to perform. The surgical hub may determine when a medical staff member is unsure about what the next step for the surgery is and may output the step to a display accessible to the medical staff member.

In examples, the surgical hub may be aware of which instruments are sterile or not sterile. For example, the surgical hub may track whether the instrument has been touched by a non-sterile medical staff and may determine that the instrument is not sterile. The surgical hub may indicate whether the instrument is located in a sterile or a non-sterile field.

Spatial temporal data associated with an object (e.g., each object) may be collected by the surgical hub. For example, the spatial temporal data may be the number of times an instrument was exchanged. The surgical hub may analyze the spatial temporal data. For example, the spatial temporal data may indicate that the instrument was exchanged many times during a surgery. In such a case, the surgical hub may assess that the instrument is significantly involved in the surgery. The surgical hub may use the spatial temporal data to optimize the surgical OR setup.

The surgical hub may coordinate the data being exchanged between objects in the surgical OR. For example, an instrument may try to send information to a wrong display screen. In such a case, the surgical hub may identify that the display screen does not want the information and may prevent the instrument from sending the information.

An object (e.g., each object) may be associated with a power signature. The power signature may be sent to the surgical hub. The surgical hub may use the power signature to determine whether the object is powered on. The power structure signature may be used by the surgical hub to determine the identity of an object. For example, the surgical hub may identify an object based on its power signature.

The surgical hub may identify and/or verify instruments by using data clusters and/or nexuses of data points. In examples, instrument orientations and/or ergonomic information related to the instruments may be determined using data clusters and/or nexuses of data points. The surgical hub may receive data associated with a display (e.g., each display) in the surgical OR. For example, the surgical hub may receive data from a data source that may be associated with the display, such as a medical instrument.

As another example, the surgical hub may determine the data that is displayed on the screen and may modify the data on the screen, augment the data on the screen, remove data from the screen, and/or add data to the screen. For example, a display associated with a generator located in the surgical OR may send data to the surgical hub. In examples, one or more cameras may monitor the display and send data associated with the monitoring to the surgical hub. For example, the cameras may see the power levels on the generator and send data associated with the power levels to the surgical hub. For example, the cameras may see error codes on the generator and may send data associated with the error codes to the surgical hub.

The instrument may send a message to the surgical hub that notifies the hub that the instrument is located in the surgical OR. The message may include the instrument's serial number. The surgical hub may record the serial number when the hub receives the message. The instrument may include the serial number when it sends data to the surgical hub. The surgical hub may use the serial number in order to identify which instrument sent the data. The surgical hub may send a response message that indicates to the instrument that the surgical hub received the message.

In examples, boundaries of the surgical OR may be determined by camera information sent to the surgical hub. A surgical hub may identify when an object in the surgical OR moved, for example, based on the camera information. For example, the surgical OR may identify that a medical staff member bumped into a surgical robot arm based on camera information that tracked the medical staff member's movement and the surgical robot arm's movement.

The surgical hub may generate information related to the change in camera information over a period of time. The surgical hub may send the information to one or more displays accessible to the medical staff. In examples, the surgical hub may determine when a medical staff member is confused based on the camera information. In such a case, the surgical hub may determine an instrument being used by the medical staff member and, based on the instrument, the surgical hub may output a next step to a display accessible to the medical staff member.

In examples, the surgical hub may receive information associated with the patient. For example, a surgeon may be firing an energy beam on an area of the patient's body. In such a case, the surgical hub may overlay the firing location onto the monitor of the firing device being used by the surgeon. The firing information may be outputted on secondary displays accessible to the medical staff supporting the surgeon. In such a case, the medical staff may know which instrument is being fired.

The surgical hub may be aware of an indicator on each medical instrument. The camera may identify the indicator and send the indicator to the surgical hub along with the medical instrument's location (e.g., via coordinate points). In examples, the indicator may include indexing ports and/or fiducial markers. The indicator may include qualities about the instrument such as the length and thickness of the instrument shaft. The surgical hub may scale the data sent to the instrument based on the qualities. The cameras may identify indexing coordination and/or registration points of the one or more instruments.

In examples, the camera may identify the instruments based on the characteristics of the instrument. For example, the camera may use spatial recognition to model the shape of the instrument. In such a case, the camera may identify the instrument based on the shape. For example, the camera may identify a handle resembling an endocutter handle and may determine that the instrument is an endo cutter.

The camera may generate data based on a display in the surgical OR. The camera may overlay information onto the display. The information may include information from another display. For example, a surgeon may request information related to a generator power level, EKG measurements, and instrument firing status. In such a case, the instrument may include a display that shows all three of these values. A surgical hub may port the information to the display the surgeon looks at from a laparoscopic point of view.

The surgical hub may identify and/or recognize one or more devices that may not be compatible with each other. The surgical hub may standardize the data into a form that may allow data to be exchanged between the devices.

The surgical hub may include machine learning that analyzes the metadata as described herein over time. The metadata may be based on camera information sent to the surgical hub. For example, the camera may read information on a display and send the information to the surgical hub over a duration of time. The surgical hub may input the information into a machine learning model to determine, for example, what the surgeon may be doing. The machine learning model may determine suggestions for the surgeon and the surgeon may send the suggestions to the display accessible by the surgeon. The machine learning module may determine when and/or where the surgical hub should send the information. For example, the machine learning model may tell the surgical hub to send information related to ligating the IMA when the surgeon performs mobilization.

The machine learning as described herein may allow the surgical hub to customize the data exchanged based on the medical staff. For example, the surgical hub may retrieve the identity of the surgeon performing the surgery and input the identity into the machine learning model. The machine learning model may adjust the suggestions based on the identity.

The surgical hub may filter and/or coordinate the data based on what the medical staff needs at a given time. For example, the surgical hub may comprise data related to the battery level of a harmonic scalpel. The surgeon may be performing a surgical task that does not involve the harmonic scalpel. In such a case, the surgical hub may filter out the harmonic scalpel data. The surgical hub may send the filtered data to a display accessible by the surgeon.

The surgical hub may determine the amount of data that may be sent to a display screen based on what the medical staff is doing. For example, the surgeon may be performing a critical task of the surgery. The surgical hub may determine not to send a visual graph to the display screen, for example, as it may distract the surgeon.

One or more monitoring systems may be provided. Hub adaptation and/or hub control may change based on spatial awareness of objects and personnel within the surgical OR.

Hub identification and/or tracking of objects and/or tracking of personnel within the surgical OR may be used to overlay data that is custom to a user's need. A surgical hub may include a system for monitoring one or more users within the surgical OR and/or the surgical instruments entering or leaving different predefined spaces within the surgical OR, for example, throughout tasks related to the procedure being conducted. The spaces may include the stock area, the mayo stand, and/or the surgical site. Tracking of the instrument may include ensuring that the instrument is ready for use in the procedural tasks needed and/or is in a state to operate correctly. The surgical hub may attach data to the instruments based on the surgical step and/or based on the user and/or monitor viewing the device. The attached data may be via built-in displays, displays of the room and/or tablets, and/or AR gear (e.g., glasses, personal displays, and/or audible instructions.) A step for tracking may be a final step and may include cleanup that ensures there are no retained objects in the patient and the product (e.g., all the product) is disposed of properly.

Hub spatial awareness and/or surgical suite monitoring and tracking of objects and/or people may be provided. Spatial awareness of surgical product and/or instruments may include their movement, positions, and/or orientations within the surgical OR. Instrument identification, spatial registration, and/or tracking within the OR may be provided.

The location where the product came from and/or the location of where the product is detected may trigger different interactions with the HCPs. The HCP may be alerted, for example, if the device has entered the OR. In such a case, the device may be added to inventory control.

In examples, tracking if a packaging has been opened may be provided. A surgical hub may use a camera, a sensor, and/or the like to determine if a package is present in an area, such as an area of an operating room. The surgical hub may determine if the package has been opened. For example, the surgical hub may receive a signal from a sensor associated with the package indicating that the package has been opened. As another example, the surgical hub may determine using a camera that the package has been opened. When it is determined that the package has been opened, the surgical hub may lock a time associated with the package being opened. The surgical hub may note in an inventory database that the package has been opened, such that the inventory may reflect that the object has been used.

Orientation and/or environmental parameters of the products may be used to trigger interactions and/or notifications to the HCP, for example, for actions and/or cautions. For example, Gyroscope and/or 3-axis accelerometers may be used to determine device orientation and/or position.

A surgical hub may alert a device of special environmental conditions to be aware of. For example, current OR atmospheric pressure may impact device performance. In such a case, the device may be alerted of potential adjustments it may need to make for optimal performance. Hub may inform devices of special internal conditions (e.g., any special internal conditions) that the patient presents.

The instruments may comprise spatial registration markers and/or visible fiducial markers on the devices that are monitorable by the hub and/or is the hub's sensor arrays. The marks may be in a predefined pattern and the hub may use an index of the devices for their markers and/or instrument configurations. In examples, the hub may be able to use the marks to identify and/or model the instrument with the 3D computer environment the hub creates and/or records.

The marks may allow a hub to adjust images and/or projections of an instrument for translation, rotation, scale, skew, and/or perspective. For example, a hub may present an augmented reality image that may show a portion of a medical instrument that may be scaled. The hub may be enabled to detect and/or monitor the instruments, for example, if a portion of the instrument is obscured.

For visible monitoring there may be a camera calibration that may be automatically conducted, for example, when the system starts up. There may be a predefined set of markers associated with the hub camera that may be fixed and may allow the hub to calibrate the camera for distance and/or focal length. In examples, the hub may determine the exact length from the hub or another calibration preset scale, for example, that may be within the OR. The hub may use the measure and/or the scale to calibrate the camera and/or focal distance.

The hub may determine the exact distance via another measurement system integral to the hub, such as laser doppler, ultrasonic pinging, RF, and/or other energy digital communication. Distance may be inferred from active or passive electronic signal processing. By monitoring the signal strength and compensating for emission power, emitting device antenna path, fight path, receiving device antenna path, and receiver sensitivity the communication between two Bluetooth paired systems may be used to determine the distance within the room Bluetooth paired systems are apart.

UHF or HF RFID tagged object tracking may involve a combination of predefined tag and/or distances in combination with unknown tags. The tags may identify the product in question and may provide information about the product. The tags may allow the product to be tracked within the room, for example, once identified.

RFID map made from passive or active references tags with known location (e.g., landmarks) may locate an unknown tag detected by the RFID reader antennas.

The system may measure one or more distances between readers and common detected tags, for example, using a large scale path loss propagation model. In examples, the system may calculate the distance between the unknown tag and the detected landmarks (e.g., inter-tags distance).

Use of millimeter-wave radar and/or tracking of objects may be provided. Millimeter-wave radar with a micrometer accuracy may be provided. A radar operating using frequency-modulated continuous waves (FMCW) may show how frequency and/or a phase of radar beat signal may be used to determine the distance between the radar sensor and the object from which the radar signal is reflected.

Instrument identification, spatial registration, and/or tracking within the OR may be provided. Instrument tracking spatially within the OR and/or through utilization may provide guidance on steps and/or supplementation of other collected and/or streamed data. Instruments may be tracked by cameras within the OR and/or cameras inside the patient.

The hub may monitor the connectivity of attached wired and/or wireless devices, detection of the room, and/or location of the devices and/or people within the OR (e.g., via ultrasound and/or visual cameras and customization of data on the displays for the user viewing the display). In examples, room displays may be used to look at the OR and/or to look at the OR through a picture-in-picture view. The display the surgeon sees may be allowed to show the same room and scope view. In examples, the display may be allowed to show differing information respective to the scrub nurse and assistant surgeon. The differing information may allow the scrub nurse and the assistant surgeon to see their job and how the devices being used relate to their specific tasks.

Setup and cleanup instrument counting may be provided. For example, the surgical hub may track an instrument. The surgical hub may determine that the instrument may need to be set up and may send a notification and/or instructions to an HCP. The surgical hub may determine that the instrument may need to be cleaned. The surgical hub may send a notification and order instructions to the HCP.

Utilization of an HCP worn or concentric camera may monitor what devices have been brought into the OR and/or may leave the OR. For example, the HCP may be wearing a camera. The camera may be within safety glasses that may be worn by the HCP. The camera may view what the HCP may be viewing. The camera may detect that an instrument may have entered the view of the HCP. The camera may identify the instrument. The camera may determine that the instrument may have been brought into the OR.

Cameras on HCP augmented reality gear may see what instruments are being handled. It may be determined, for example, using the augmented reality gear, that an instrument may comprise a label that may provide an identity. In examples, the cameras may scan bar codes and/or QR codes, for example, to identify serial numbers and/or product specifications.

The AR device may highlight viable reloads, for example, if an instrument has been specified for a procedure through the procedure plan or having been unpackaged within the OR as the HCP looks over stock room storage of reloads. The AR device may highlight via multiple levels competitive verse recommended for the patient and/or procedure.

Product scanning devices (e.g., barcode scanning laser, radio frequency identification (RFID) handheld scanner, RFID doorway scanner, optical QR code reader or camera, and/or another inventory scanning system) may be used to track and/or tag what products have been used in an OR. These scanners may ensure that the products brought into the OR are removed.

As two items that are related are scanned in, the hub may identify the compatibility of the items and may highlight discrepancies. As the scanning system scans a reload or instrument that is not compatible, the hub, scanner, and/or other user interaction device may highlight the discrepancy before the products are removed from their sterile packaging. As the products are scanned for removal, the device may highlight the acceptable disposable and/or recovery methods for the device. The hub may update the scanners with regional information, for example, based on where the hub knows the procedure is being conducted.

In examples, the hub may communicate with the facility to determine the disposal vendors and/or the methods and/or locations the vendors for that facility want the systems to be discarded. The hub may notify the edge processing system, for example, to tabulate and/or notify the disposal. The hub may reclaim vendors, for example, if sufficient product is ready for removal.

The hub may analyze the quantity of devices, for example, which may be re-sterilized. The hub may analyze what methods are involved for a given device, for example, in order to assist hospital cleaning and/or sterilization departments with predicting capacity and/or anticipating workload.

Monitoring instruments entering or leaving the patient treatment site may be provided. For example, as sponges, sutures, instruments, etc. are moved from the Mayo cart to the surgical site, the items may be individually identified and/or monitored via optical, RFID, electromagnetic, and/or ultrasonic sensing systems. This may provide the hub situational awareness of the step or task that is underway. The hub may notify the supporting HCPs for next steps and/or anticipate participation. In examples, the hub may ensure that there are no retained surgical instruments in the patient.

The hub may track the instruments used in the surgery and may track how long the instrument may be used during the surgery, for example, to determine if the product was involved in the procedure or ended up being wasted product. Monitoring and/or annotation of other data monitoring systems with instrument proximity and usage may be provided. Instruments may be tracked by cameras within the OR and/or inside the patient.

HCPs interactions may be identified, for example, for annotating event and situational awareness. HCP tracking within the OR and/or monitoring interactions may be provided.

The hub, scanners, and/or monitoring systems may track the instruments and the users and HCPs interacting with them. In examples, the hub may track which HCP brought the inventory to the room and at what time. In examples, the hub may record the HCP that opened the sterile packaging and at what time. In examples, the hub may track how long the product has been open and under what environmental conditions.

In examples, the hub may track when the product is reliable and/or when the product effectiveness is beginning to be effected. The hub may provide one or more instructions to be taken to minimize the effect. In examples, the hub may track the HCP or surgeon that used the product.

Recorded metadata may include usage characteristics. Usage characteristics may include one or more of the following: patient, procedure, procedure step, usage amount, preference data, orientation, location, and/or the like relative to the surgical site, HCP tracking within the OR and monitoring interactions, or spatial and/or temporal tracking and recording of instrument and equipment operations and usage.

Monitoring and recording of time, position, and orientation recording of instruments during usage may be provided.

The detection, monitoring, and/or recording of the instruments with respect to each other, the surgical staff, the room equipment, furniture, and the patient may enable the data analysis of usage, ease of use, common usage grips, and/or handling, as well as the amount of time the instruments are in differing orientations.

Tracking of the instrument and the instrument's orientation and which cameras may visualize the instrument may allow the hub to overlay data and/or secondary imaging indicating a status, highlight, and/or instruction onto the instrument, for example, to assist the user of the instrument.

Overlay of data onto instrument aspects may be different for different views and/or viewers. In examples, the overlay may be changed by the system based on the user interacting with the device. In examples, the overlay may be different for different monitors of the device.

For example, a surgeon may perform a thoracic lobectomy and may be approaching the vascular transection step. The vascular endocutter may be missing from the OR mayo cart and may be present in the stock area within the cabinets at the perimeter of the room. In such a case, the space on the mayo cart may be highlighted by the hub and the hub may monitor the space and/or may display an image indicating that that the device is missing at the space. The hub may indicate to the circulation nurse where the vascular endocutter is located. The nurse may bring the device into the area and may open and drop it sterilely onto the mayo stand and the camera may automatically identify the device and may identify that the device is unloaded. The monitor for the nurse may overlay the unloaded status and the controls to actuate, for example, to begin the loading steps. In such a case, the monitor for the surgeon may show the devices and instead of loading highlight the monitor may show the tissue type compatibility, reload need, and/or the status of the device. In such a case, the overlay of data and the highlighted data may be different for different users and may be different for the different displays looking at the device. The hub may record all of the operations and tasks in time for compilation (e.g., later compilation). The displays may be personal displays such as wearables, local displays on the device, and/or AR glasses or equipment.

In examples, overlay of data onto instrument aspects may be different for different views or viewers.

Image capturing of the areas outside the abdomen (e.g., device orientation, position, and status as well as user body position, staff activities, and other actions within the OR, etc.) may improve the placement, and/or control of the surgical device in use.

Spatial awareness of system integration and connections may be provided.

Adaptive control of interactions may be based on distance, wiring linkages, and/or port attachments.

Detection of the OR room and the hub(s) within the OR may allow the systems to define the room boundaries, to know which hubs to communicate to, and/or to know what list and/or procedure needs to compare the product for authentication and/or compatibility issues.

In examples, the camera(s) may be utilized within the OR to determine the setup, location, interconnection, and/or orientation of the equipment connected to the hub, robot, or room to configure the setup of the systems.

OR cameras and displays may identify equipment. OR cameras and display may be used to setup and initiation the equipment.

In examples, the camera may guide the user in reconfiguration and/or trouble shooting of the system layout, for example, to reconfigure the interconnections of the coupling of multiple systems to achieve inter-connectivity.

Equipment that is close to each other and may interfere or inhibit function of one or more of the equipment may be identified.

Patient attached leads and/or other incorrect setup and connections may be identified and the user may be instructed on how to correct the issue.

In examples, one or more display in the room may be configured to help a health care professional. For example, one display may be configured to help a first HCP and a second display may be configured to a second HCP. In an example, a display may be configured to provide steps-for-use for a medical instrument, a procedure task, and/or the like. Information displayed based on the user. For example, a first display may display a first set of information for a first HCP based on the task and/or job performed by the second HCP, and a second display may display second set of information for a second HCP based on the task and/or job performed by the second HCP. A display or a first portion of a display may show tasks and/or locations of a surgery while another display, or a second portion of the display may show a surgical view.

Displayed information based on the user and/or the user's location within the OR may be customized.

During surgery an OR team may perform function in coordination with one another, for example, to create an atmosphere that benefits the patient. Personnel inside the OR may comprise the operating surgeon, assistants to the surgeon, a scrub person, an anesthesiologist, and/or a circulating nurse. Each member of the team may comprise different responsibilities throughout the procedure and may interact amongst each other and may be in sync with each other in order for efficiency and successful outcomes. In examples, OR rooms may be intense, high stress, and challenging environments in which a medical staff member may get distracted and/or forget important steps that may cause delays and/or disruptions in focus with individuals and/or other team members. Utilization of the OR room displays and/or tablets may be customized to help each of the healthcare providers to know which action to do (e.g., based on monitoring the viewing user), steps-for-use, procedure step that are needed, or to predict steps to optimize the efficiency and/or focus of the team. The OR displays may be unique to each staff member and each staff member's responsibilities. In such a case, the individual looking at a monitor may be identified and the monitor may display that individual's task details.

An example of an individual involved in the surgical OR may be the surgeon.

For example, during the procedure, the display or a corner of the display to not occlude the surgeons view may identify which instrument and/or device was in his hand and may provide a steps for use (e.g., either text or visual image highlight the buttons to a user). If a step is detected that the step was pressed in a wrong sequence, the display may highlight the step and may alert the user.

In examples, prior to the start of surgery, the display that the surgeon and/or assistant are looking at may show a snapshot of the gold standard and/or watch-outs for risks for that patient based on patients bio markers.

In examples, during surgery the surgeon may be picking-up or putting-down instruments on the operating table or instrument table and the screen may provide indication(s) in the corner of the screen of where the instrument is located (e.g., prior to him needing the instrument) and the surgeon may keep focus on the screen and reach for the instrument with his hands. In examples, the hub knowing the procedure steps and knowing what instruments are plugged into it may know when instruments are needed prior to use. The monitoring system may verify that a task is completed and may know which step is needed next. The notification of what instrument is needed and when it is needed may be notified to the scrub nurse and/or assistant and they may be prepared to hand to the surgeon prior to him requesting or needing the instrument, e.g., which may improve efficiency within the OR and allow the surgeon to maintain focus.

An example of an individual involved in the surgical OR may be the scrub nurse.

For example, during surgery, the scrub nurse, circulating nurse, and/or assistant may be responsible for altering the settings of the equipment for the surgeon. In such a case, the display may provide an overview of the OR room layout and may highlight the location of the piece of equipment that requires modification. The display may show a visual image of the piece of equipment and may show steps for use on how to adjunct the setting. In examples, the monitor, hub, and/or display may confirm that the correct setting is adjusted to the correct value, for example, as a verification.

For example, a scrub nurse may be responsible for ensuring tools and the field are sterile. In such a case, the display may be set up as a checklist, for example, to indicate items needed and confirm that the items are sterile. The display may provide an indication based on the procedure type, equipment required, and/or room layout. The display may indicate how the sterile field should be and may confirm that the sterile field is ready.

An example of an individual involved in the surgical OR may be the circulating nurse.

For example, a responsibility of the circulating nurse may be the accountability of the quantity of surgical items, for example, prior to the operation and after the operation to ensure no surgical items are retained in the patient. In such a case, the display may be used as a checklist and the hub knowing the procedure may create a checklist of the items involved in the surgery and may track as the surgery is performed and after the surgery is performed to ensure the items are collected. The display may highlight, for example, if there are discrepancies and may alert the team prior to starting the procedure or closing the site.

For example, a responsibility of the circulating nurse may be preparing and positing of the patient on the table. In such a case, the display may be used to indicate how the patient should be positioned on the table and the system may verify prior to starting the surgery. In examples, the patient placement may be based on surgeon preference and/or gold standard procedure data.

For example, a responsibility of the circulating nurse may be ensuring the correct site and procedure is completed on the patient. In such a case, the display may be used as guidance in preparation and/or verification of site and procedure completed.

An approach may be based on jobs and/or locations within the OR (e.g., geographically). In examples, the team may be divided into divisions according to the function of its members. One team may be a sterile OR team and may include operating surgeon, assistants to the surgeon, and scrub person(s). One team may be an Unsterile OR team and may include anesthesiologist or nurse anesthetist, circulator, and other OR members that may be needed in operating specialized machine or devices.

In examples, the sterile OR team may perform surgical hand washing (e.g., arms are included) and may prepare sterile gowns and gloves. In such a case, the displays within the OR may identify the items needed for each of the assigned staff and may use the monitoring system to confirm the task are completed, for example, before allowing the screens to go into the procedure mode. The display may highlight and notify, for example, if a staff member missed a step. The surgical OR team may enter the sterile field. In such a case, the display may show a layout of the OR room and may highlight the different sections or boundary of the sterile field to the staff. Operating rooms may differ in layout and/or boundaries or new staff members in which the monitor may be used to inform and/or remind of sterile field boundary for the OR room. The surgical OR team may handle sterile items. In such a case, the hub may monitor and provide notification on the display on who has authorization to use and/or pass a sterile instrument and if a non-sterile team member attempted to use and/or pass, the hub may provide on the display a warning and/or notification directed at that staff member.

In examples, the unsterile OR team may include an anesthesiologist, circulator, biomedical technicians, radiology technicians, and/or other staff that may set up and/or operate specialized equipment and/or devices essential in monitoring the patient during a surgical operation.

The displayed information may be customized based on the user and/or the user's location within the OR. In examples, spatial awareness may be supplemented with temporal awareness. For example, when a task is needed relative to the procedure, the supplementation may include where the hub is and how the hub is connected to other systems within the OR. Temporal as well as spatial awareness of module and system connection to the hub may be provided. Hub may track OR staff locations within the OR suite. For example, the primary and/or secondary tasks may be displayed on the monitor closest to the staffs' current position. Additional tasks may be visually shown in a list. For example, the current task may be highlighted and/or bolded. In examples, the hub may show the current instructions and may show if the staff is not following the current procedural steps.

Sub-system self-identification, indexing, and/or integration may be provided. The hub or a higher level hierarchical system may automatically identify attached devices based on the devices' ID, signature of the devices' power usage or provided data streams, and/or by visually or electronically viewing the attached devices. Automatic identification and setup of attached devices based on their data or power signatures may be provided.

In examples, the data stream being communicated from the device to the hub may be used to identify the device, the device's setup configuration, and the device's operating program by comparing the data stream with previous summaries of data streams provided by the device. The signature of the metadata, organization of the data, and/or organization of the communication packets may be specific to the function, make, and model of the device and may be used to track and automatically setup the system, for example, when the device is attached to a higher level system.

The headers, data packet details, metadata, transmission frequency, and/or hand-shake may be used to ID a specific piece of equipment relative to other similar equipment. Errors, consistence noise, and/or other individualized additive elements may create a trackable signature of data transmission and/or power usage to ID a unit.

Automatic identification and/or setup of attached devices based on their data or power signatures may be provided.

Hub identification and/or tracking of objects and/or personnel within the OR to overlay data that is custom to the user's need may be provided. For example, a surgical hub may include a system for monitoring the users within the room and the surgical instruments entering or leaving different predefined spaces within the OR throughout specific steps and/or tasks related to the procedure being conducted. The spaces may include the stock area, the mayo stand, and/or the surgical site. Tracking of the instrument may include ensuring the instrument is ready for use in the procedural steps needed and is in a state to operate correctly. In examples, the hub may attach data to the instruments based on the surgical step and/or the user or monitor viewing the device. For example, the attached data may be via the built-in displays, displays of the room and/or tablets, and/or AR gear (e.g., glasses, personal displays, or audible instructions.) One of the tasks for tracking may the finals step and cleanup insuring there are no retained objects in the patient and the product is disposed of properly.

Interaction with other facility systems and servers may be provided. OR inventory management system may be included in the hub. For example, the OR inventory management system may include billing and/or reimbursement authorization of treatment adjustments.

For example, the OR inventory management system may include adjustment of the procedure approach, instruments used, and/or medicant adjuncts based on the pre-authorization or procedure classifications.

Advanced imaging may be provided. Monitoring systems may be provided.

Hub adaptive control and/or operation of display and display interactions may be based on recognition of users, equipment, and/or usage, and user or equipment needs.

In examples, configuration of the display settings and/or displayed information may be based on the recognition of the user(s), and/or awareness of procedure, location, or usage. In examples, a surgical hub may be interconnected to display devices within the OR and may monitor and track the personnel, the procedure, and/or the patient. The hub may comprise the capability of communicating changes in each of the displays based on the situation at hand and/or the user or viewer of the display. The hub may be monitoring the procedure and/or patient, may be tracking personnel within the OR, and may be capable of relating position and/or direction of a display with the user of the display. In examples, the hub may comprise recognition algorithms that enable the hub to differentiate between users, equipment, and/or instruments within view of the hub's sensors within the OR. The hub may customize the display setting, the displayed information, and/or the instructions for the user and the step or task at hand. For example, the displays may be personal display units such as AR devices, surgical interface tables, equipment displays, local instrument displays, and/or room monitors positioned and aimed towards certain user locations.

Smart display system interaction and control may be provided. Cameras and/or sensors on one display may be used to monitor other display systems within the OR. Monitoring of one display with a camera may be used for display control and/or data collection.

In examples, a system may be used to monitor utilization, setup parameters, and/or determine which users are viewing and/or interacting with displays in the OR. A display may be monitoring information on another display for control cues and may be able to repeat or redisplay information from the other display.

In examples, the surgeon interaction display (e.g., main surgeon interaction display) may be watching patient monitoring systems such as EKG, blood pressure, sedation levels, O2 levels, etc. and may add information related to the patient monitoring system to its primary display. In such a case, the surgeon may look in one location for the compiled data (e.g., all the compiled data).

Displays may be broadcasting information in light bands outside the visual range or audible levels outside of the hearing range, for example, in order to coordinate information between displays for the users, which may be HCPs.

In examples, monitoring of multiple displays may be used as a level of confirmation of the procedure step, patient vitals, instruments in use, and/or the like. Multiple cameras may feed information into the hub system and the cameras may derive different information and may be used to confirm one another.

Assisted and/or expanded control of displays via interaction with the system verbally, visually, or physically may provide deep context to the display interaction. Assisted AI control of the display via variable inputs from the user may be provided.

Smart device control and/or interaction with smart displays may be used in order to allow the users within the room to control the displays with the devices in the users' control. For example, AR gear, smart watches, surgeon tables, and/or other instruments may be used to create individual links and/or pairing to some or all the displays in the OR, for example, in order to control what is displayed, and the parameters of the display.

Procedure, HCPs, and/or patient data may be used to determine default interaction controls for the display to allow the users intuitive interaction and control of the display and the display's data.

Voice-controlled displays may be used for changing display parameters or what is displayed or connected to the display.

AI interaction and/or direction of control parameters of the displays may be provided, for example, which may include predefined control words and/or gestures as well as ability search behavior and/or systems to interpolate commands between the predefined variables.

In examples, individualized experiences and/or responses may be used as the system may differentiate between individuals based on voice recognition, imaging of the users, and/or other electronic identification of the individuals.

Touch display supplementation of the display settings and control may enable navigation through options and may explore aspects of the displayed imaging and analyses. Assisted AI control of the display via variable inputs from the user may be provided.

A communication portal may be used by an HCP to communicate with another HCP. In examples, the verbal inputs may be utilized by the smart display to control communication outside of the OR.

The display may transcribe the spoke request and/or information and may send (e.g., digitally send) the message and/or request via SMS, email, and/or other electronic means.

Requesting a skill set and/or person may allow the display and/or hub to identify and locate the individual involved in assisting in the requested task and may send a notification to the person indicating the need for help and where the help is needed.

In examples, the system may segment the requested help or step into the system's needed tasks and may identify the available personnel (e.g., the most available personnel) with the needed skill set and notify the personnel of the need for help.

The system may make skill set and/or person recommendations to the surgeon and may highlight, rank, specify strengths or weaknesses, and/or the like of the recommendations and may allow the surgeon to choose. In such a case, the surgeon may be informed (e.g., significantly informed).

Smart display setup configurations may be based on identification of the users and/or staff, previous usage, and/or procedure or patient parameters.

Smart setup, configuration, and/or orientation control of the display may be based on user ID. In examples, previous uses may be used for improving the location, orientation, and/or displayed information.

Internal display setting may be adjusted based on the sensed users, procedure, and/or patient configuration, for example, which may increase contrast, may make the color saturation greater or less, and/or may change the background or base coloration to improve visibility and/or interpretation of the data being displayed by a user.

User interaction and utilization may include which HCPs use the displayed information, how often is the system or display used, what is the display information used for, which HCPs interact the most with the system, the orientation, utilization timing and amount, and where within the room the users are located.

Smart setup, configuration, and/or orientation control of the display may be based on user ID. Control of collected and/or communicated data by which systems may be known and the communication through which means and pipe ways may be known.

Circumstances regarding the monitored product and monitored by what object may be recorded, for example, to understand workflow and product flow through the facility.

In examples, the monitored data may include what system(s) have detected the item and where, when, and in what state the item may be in when detected.

Metadata identification of a source of the monitored data may be tied to the data. Metadata identification may include one or more of the following: measures and/or tracking, orientation, distance and/or location, height differentiation, time monitoring systems, NFC ultra-wideband (UWB) bluetooth visual visible light spectrum, multi-spectral aspects, passive thermography, surgical staff stressors, and illness task criticality.

Interaction with other facility systems and servers may be provided. OR inventory management system may be included in the hub. For example, the OR inventory management system may include billing and/or reimbursement authorization of treatment adjustments. For example, the OR inventory management system may include adjustment of the procedure approach, instruments used, and/or medicant adjuncts based on the pre-authorization or procedure classifications.

Figure 24:
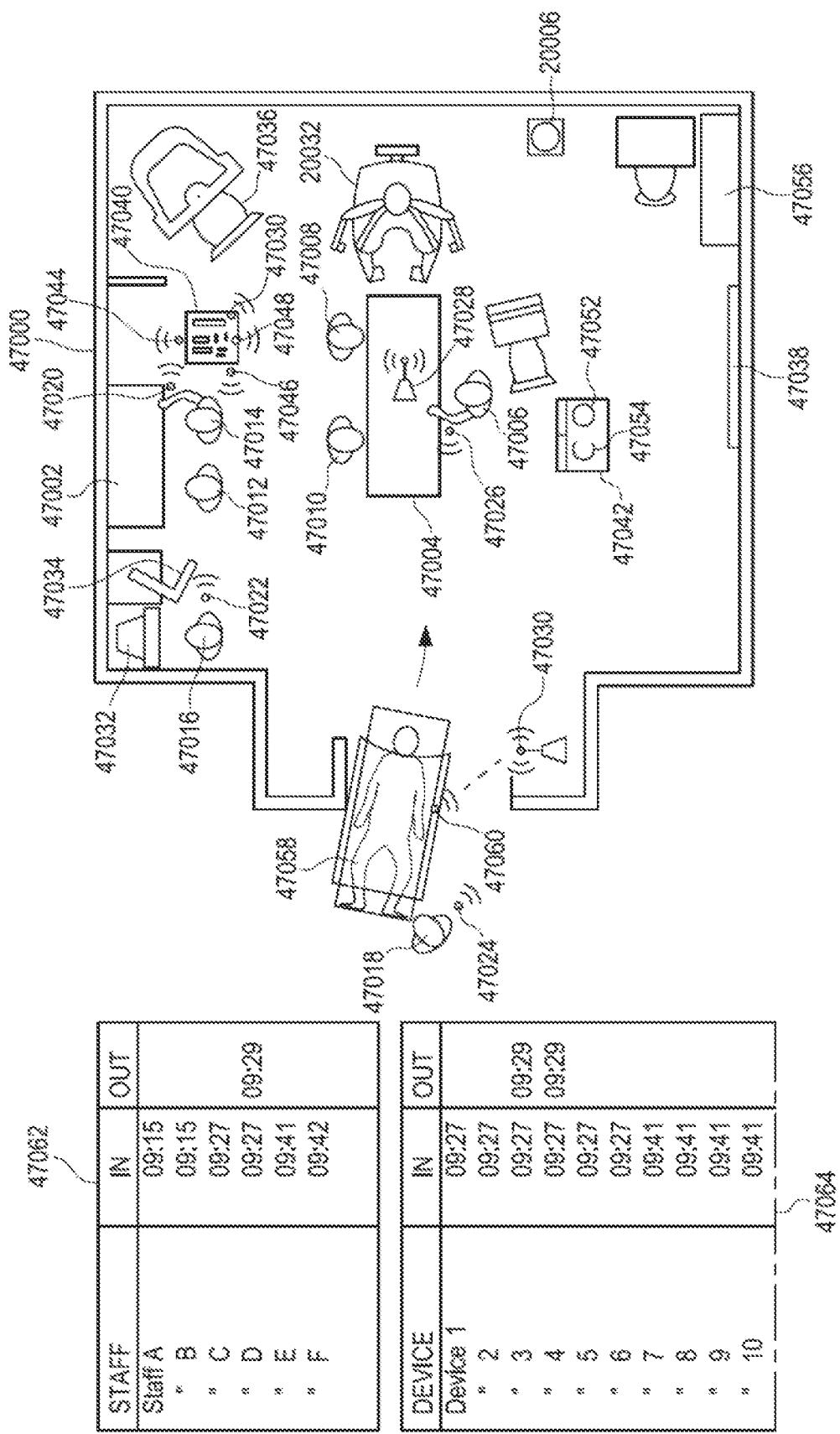
FIG. 24 depicts a diagram of an OR that may include a surgical hub for tracking patients, health care providers, surgical objects, surgical projects, and/or surgical instruments.

FIG. 24 depicts a diagram of an OR that may include a surgical hub for tracking patients, health care providers, surgical objects, surgical projects, and/or surgical instruments. As described herein, a sensor may send or receive a signal that may be used by the surgical hub 20006. For example, a sensor may be an RFID, a Bluetooth device, a computer, a wearable device, a smartphone, a smartwatch, a radio transmitter dash receiver, and/or the like.

In examples, one or more surgical hubs may determine if an object is located in the surgical OR. In examples, the surgical hub(s) may determine if an object is absent from the surgical OR. In examples, the surgical hub(s) may determine if the object is located in a room adjacent to the surgical OR. The surgical hub(s) may operate in concert or may operate independently. An object may be a smart device such as a smart medical instrument.

The operating room 47000 may include a surgical hub, such as surgical hub 20006. The surgical hub 20006 may use a ping (e.g., an ultrasonic ping), for example, to define the boundaries (e.g., walls) of the surgical OR. The surgical hub 20006 may be aware when objects enter or leave the surgical OR. The surgical hub 20006 may be connected to a number of sensors that may be used to detect the presence, absence, and/or movement of a patient, an HCP, a surgical product, a surgical instrument, and/or the like. As used herein, a surgical instrument may be referred to as a medical instrument or vice versa.

The surgical hub 20006 may include a number of sensors and/or may communicate with a number of sensors to determine one or more areas and/or spaces of the operating room. For example, the surgical hub 20006 may determine that the operating room 47000 may include a sterile field and a non-sterile field. The surgical hub 20006 may determine that the operating room 47000 may include a back table 47002 that may be used by an HCP to prepare medical instruments and/or products for surgery. The surgical hub 20006 may determine that the operating room 47000 may include an operating table 47004. The surgical hub 2006 may also determine other areas that may be associated with the operating room 47000, such as an area occupied by a patient, an area occupied by an HCP, an area outside the operating room 47000, an operating room adjacent to the operating room 47000, and/or the like. The areas may include the stock area, the mayo stand, and/or the surgical site.

The operating room 47000 may include a patient side cart 20032. The patient side cart 20032 may also be referred to as a surgical robot. The surgical hub 20006 may monitor the surgical robot 20032. The surgical hub 20006 may determine the location of the surgical robot 20032. The surgical hub 20006 may determine whether the surgical robot 20032 may be within an area that may include a sterile field. The surgical hub 20006 may determine whether the surgical robot 20032 may be within an area that may include a non-sterile field. In an example, when the surgical robot 20032 may have been in a non-sterile field and the surgical hub 20006 determines that the surgical robot 20032 may not have been prepared for surgery, the surgical hub 20006 may notify the HCP that the surgical robot 20032 is to be cleaned and/or prepared for surgery before use.

The operating room 47000 may include one or more HCPs, such as HCP 47006, HCP 47008, HCP 470010, HCP 47012, HCP 47014, HCP 47016, and/or HCP 47018. The surgical hub 20006 may use one or more sensors and/or one or more cameras within the operating room 47000 to monitor, track, and/or detect the one or more HCPS. For example, HCP 47014, HCP 47016, and/or HCP 47006 may be wearing a wearable sensor which may be detected by the surgical hub 20006. The wearable sensors may include sensor 47020 which may be associated with the HCP 47014, sensor 47022 which may be associated with the HCP 47016, sensor 47024 which may be associated with the HCP 47018, and/or sensor 47026 which may be associated with the HCP 47006. The wearable sensors may be any suitable sensor for tracking a person, such as an RFID tag, a smartwatch, a smartphone, a computer, a Bluetooth device, and/or the like.

The surgical hub 20006 may monitor and/or track HCP using a wearable device. For example, the surgical hub 20006 may receive a signal from the wearable device that may indicate the presence of the device in the room period by associating the wearable device with a person. The surgical hub 20006 may estimate and/or determine where that person may be within the OR. The surgical hub 20006 may use a location determined from a wearable device to determine an area where the associated person may be within the OR. For example, the surgical hub 20006 may determine that the HCP 47014 may be at a back table. Using contextual information, the surgical hub 2006 may determine a task that may be performed during a surgery and may associate the location of an HCP with that task. For example, the surgical hub 20006 may determine that the HCP 47014 is at the back table 47002 to prepare a medical instrument to be used in current surgical task.

The operating room may include one or more cameras. The one or more cameras may include cameras that may be on a wearable device that may be worn by an HCP. For example, the HCP may be wearing safety glasses that may include a camera. The surgical hub 20006 may utilize data from one or more cameras within the OR to determine a location of a person, such as an HCP. For example, the surgical hub 20006 may use a camera within the operating room to determine the location of the HCP 47010. As another example, the surgical hub 2006 may use a camera associated with safety glasses worn by the HCP 47010 to determine the location of the HCP 47008.

The operating room 47000 may include sensors that are associated with areas of the operating room. For example, the sensor 47028 may be placed on or near the operating table 47004 such that the surgical hub 2006 may associate the sensor 47028 with the operating table 47004. As another example, sensor 47030 may be near the entrance of the operating room 47000 such that the surgical hub 20006 may associate the sensor 47030 with the entrance of the operating room 47000.

The operating room 47000 may include one or more displays such as display 47032, display 47034, display 47036, and/or display 47038. The surgical hub 20006 may determine the presence of a display, may determine the capability of the display, and may determine what may be displayed on a display. For example, surgical hub 20006 may determine that display 47038 may be a primary display that may be used for displaying X-rays of the patient during a surgical task of the surgical procedure. The surgical hub 20006 may determine that the display 47038 is a display that may be capable of super imposing one or more images. The surgical hub 20006 may instruct display 47038 to display the X-rays of the patient along with a video stream taken from a medical instrument that is being used by HCP 47008 during a surgery. As another example, surgical hub 20006 may determine that display 47036 may be used by HCP 47014. The surgical hub 20006 may determine data that may be relevant to HCP 47014 and may send an instruction 247036 to display the data that is relevant to HCP 47014.

Operating room 47000 may include Mayo stand 47040 and Mayo stand 47042. The surgical hub 20006 may determine a terminal location of Mayo stand 47040 and/or Mayo stand 47042. For example, the surgical hub 20006 may use a camera located within the operating room 47000 to determine the location of Mayo stand 7040 and/or Mayo stand 47042. The surgical hub 20006 may determine that Mayo stand 47040 and/or Mayo stand 7042 may be located within a sterile field. Surgical hub 20006 may determine that Mayo stand 47040 may be associated with a number of medical instruments. For example, surgical hub 20006 may determine that medical instrument 47044, medical instrument 47046, medical instrument 47048, and medical instrument for 47050 may be on top of Mayo stand 47040. Surgical hub 20006 may determine that Mayo stand 47042 may be associated with a number of medical products. For example, medical product (e.g., surgical product) 47052 and medical product 47054 may be located on top of Mayo stand for 47042. Surgical hub 20006 may determine that surgical product 47054 may have entered the surgical room at a first time and may have been opened at a second time. Surgical hub 20006 may determine the surgical product 47052 may have entered the surgical room at a time and may not have been opened. Surgical hub 20006 may determine that surgical product 47052 may be associated with another surgical product which may be stored at storage 47056, and surgical hub 20006 may notify HCP that the surgical product associated with surgical product 47052 may be located at storage 47056.

Surgical hub 20006 may determine a location of a patient. For example, patient 47058 may be associated with a sensor 47060. Sensor 47060 may be a wearable device. Surgical hub 2006 may determine that patient 47058 may have entered the operating room 47000 at a time. Surgical hub 20006 may record that patient 4705 having entered the operating room 4700 at the time. Surgical hub 20006 may determine that patient 47058 may have been prepared for surgery, may be moving through a non-sterile field, and may be moving toward operating table 47004. Surgical hub 20006 may identify individuals and their objects that may come in contact with patient 47058. For example, surgical hub 20006 may log a list of medical instruments that may have been used on patient 47058; medical instruments that may be used on patient 47058; surgical products that may be used during the surgical procedure to be performed on patient 47058; HCPs that may be involved with the surgical procedure to be performed on patient 47058; HCPs that may have come in contact with patient 4705 before, during, or after the surgical procedure, and/or the like.

Surgical hub 20006 may keep a log of surgical staff that may be involved with the surgical procedure to be performed on patient 47058. For example, as shown at 47062, surgical hub 20006 may record when an HCP enters the operating room 47000 and may record when an HCP exits the operating room 47000. The surgical hub 20006 may record when patient 47058 enters or exits operating room 47000.

Surgical hub 20006 may keep a log of medical instruments, devices, and/or medical objects (e.g., medical products) that may be involved with the surgical procedure to be performed on patient 47058. For example, as shown at 47064, surgical hub 20006 may record when a medical device, such as a medical instrument, enters the operating room 47000 and may record when the medical device exits the operating room 47000.

The surgical hub 20006 may be included in a tiered software system. The surgical hub 20006 may use spatial awareness, for example, when determining if surgical objects are located in the surgical OR. As disclosed herein, a surgical object may be one or more of a surgical instrument, a surgical product, a medical device, a surgical device, a medical instrument, and/or the like. A medical object may register to the surgical hub 20006. For example, medical instrument 47046 may send a respective identification and/or serial numbers to the surgical hub 20006. The surgical hub 20006 may track medical instrument 47046 respective positions within the operating room 47000. In examples, one or more cameras may be used to track the objects. The cameras may be in communication with the surgical hub 27000.

The surgical hub 20006 may determine if an object is inside a patient and may indicate to remove the object. For example, the surgical hub 20006 may determine that surgical product 47054 has been opened and may have been placed inside patient 47058 during a surgical procedure. The surgical hub 20006 may determine and/or track a spatial temporal component associated with surgical product 47054. For example, the surgical hub 20006 may track when surgical product 47054 may have been opened and when surgical product 47054 may have been placed inside patient 47058. In an example, surgical hub 20006 may determine that surgical product 47054 is to be removed from patient 47058.

The surgical hub 20006 may determine and/or track a spatial temporal component associated with medical instrument 47044, medical instrument 47046, medical instrument 47048, and/or medical instrument 47050. The surgical hub may overlay data on medical instrument 47044, medical instrument 47046, medical instrument 47048, and/or medical instrument 47050. For example, the object may be the medical instrument 47044. A display may be configured for the overlaid data. The display may be included on the medical instrument 47044. The display may be attachable to the medical instrument 47044. The data may be depicted on the screen for a user to see. The cameras as described herein may observe a change in the surgical OR and may overlay data associated with the change to a medical instrument display.

The surgical hub 20006 may be aware of secondary objects located in a storage destination, such as storage 47056. The surgical hub may determine when one or more secondary objects are involved in a surgery. In examples, the surgical hub may communicate to an HCP (e.g., a rotating nurse) to retrieve the secondary objects from storage 47056 at a time for a surgical task to be performed.

The surgical hub 20006 may be aware of a medical instrument that may be involved in a surgery. For example, medical instrument 47044, medical instrument 47046, medical instrument 47048, and/or medical instrument 47050 may be involved in an upcoming surgical task of the surgery. The display 47034 may be accessible to a table nurse, such as HCP 47016, and may be in communication with the surgical hub 27000. The surgical hub may indicate the instrument involved in the surgery on the display. For example, the surgical hub 20006 may highlight the medical instrument 47046 on the display 47034. The instrument involved in the surgery may be located in a storage destination as described herein. The surgical hub may indicate the storage destination that the instrument is located at.

Augmented reality may be used by the surgical hub 20006 to indicate a medical instrument being used. For example, the augmented reality may be associated with a secondary display overlaid on another display. The surgical hub 20006 may use augmented reality to highlight the instrument involved in the surgery. For example, surgical hub 20006 may determine that medical instrument 47050 may be used by HCP 47008. The surgical hub 20006 may determine that HCP 47008 is wearing safety goggles that include a display. The surgical hub 20006 may send data associated with the medical instrument 450502 to the safety goggles associated with HCP 47008 such that data is overlaid over the view as HCP 47008 looks through the safety goggles.

The surgical hub 20006 may use one or more cameras within OR 47000 to analyze HCP, such as HCP 47008. Surgical hub 20006 may determine that HCP 47008 may be using medical instrument 47046. Surgical hub 20006 may determine that HCP 47008 may be unsure about the current surgical test that involves HCP 47008. For example, surgical hub 20006 may analyze HCP 47008 gestures and/or posture and may determine that HCP 47008 may be confused or may be using medical instrument 47046 inefficiently. Surgical hub 20006 may send a notification to HCP 47008 using display 47038. The notification may indicate instructions regarding the surgical task to be performed using medical instrument 47046. The surgical hub 20006 may continue to monitor HCP 47008 to determine if the instructions assisted HCP 47008.

The surgical hub 20006 may customize and/or personalize one or more displays for an HCP. For example, surgical hub 20006 may customize display 47032 for HCP 47016. As another example, surgical hub 20006 may customize display 47038 for HCP 47008.

In examples, the surgical hub 20006 may be aware of which instruments are sterile or not sterile. For example, the surgical hub 20006 may track whether an instrument has been touched by a non-sterile medical staff and may determine that the instrument is not sterile. The surgical hub may indicate whether the instrument is located in a sterile or a non-sterile field. For example, the surgical hub 20006 may determine that medical instrument 47046 was sterile, may determine that HCP 47018 has come in contact with the medical instrument 7046, and may determine that medical instrument 47046 is no longer sterile. As another example, surgical hub 20006 may determine that medical instrument 47048 may have been dropped on the floor of operating room 47000 and may no longer be sterile. As another example, surgical hub 20006 may determine that surgical product 47054 may have been opened and may no longer be sterile.

Spatial temporal data associated with a medical object may be collected by the surgical hub 20006. The spatial temporal data may be the number of times an instrument was exchanged. For example, the spatial temporal data may indicate that the medical instrument 47044 was exchanged between HCP 47008 and HCP 47014 five times. The surgical hub may analyze the spatial temporal data. For example, the surgical hub 20006 may determine that medical instrument 47044 may be involved in the surgery based on a number of exchanges between HCP 47008 and HCP 47014. The surgical hub may analyze the spatial temporal data to optimize the surgical OR setup.

The surgical hub may coordinate the data being exchanged between medical objects in the surgical OR. For example, medical instrument 47046 may try to send information to display 47038, which may be an incorrect display. In such a case, the surgical hub 20006 may identify that display 47036 may be a suitable display. The surgical hub 20006 may send data to display 47036. The surgical hub 20006 may prevent medical instrument 47046 from sending information to display 47038.

A medical instrument and/or medical product may be associated with a power signature. The surgical hub 20006 may determine the power signature and may determine that a medical instrument and/or medical product has been powered on based on the power signature.

The surgical hub 20006 may identify and/or verify medical instruments by using data clusters and/or nexuses of data points. In examples, instrument orientations and/or ergonomic information related to the instruments may be determined using data clusters and/or nexuses of data points. For example, the surgical hub 20006 may receive data associated with display 47038 and display 47036, which may be associated with a generator located in the OR 47000. The generator may not be able send data directly to the surgical hub 20006. The surgical hub 20006 may use one or more cameras to monitor the display 47036 such that the surgical hub 20006 may have an ability to read the display 47036. For example the surgical hub 20006 may determine the power level of the generator from the display 47036 and may adjust one or more medical instruments in the OR 47000 based on the determined power level of the generator. As another example, surgical hub 20006 may determine a setting of the generator and may display the setting of the generator on display 47038. As another example, surgical hub 20006 may determine that there is an error code on display 47036 and may send notification to HCP 47008 regarding the error.

The surgical hub 20006 may receive a message from a medical instrument that indicates identifying information for the medical instrument. For example, medical instrument 47046 may send a message to surgical hub 20006 that may include a serial number for the medical instrument 47046. The surgical hub 27006 may log the serial number of the medical instrument 47046. The surgical hub 27006 may identify the medical instrument 47046 using the serial number and may customize one or more settings for the medical instrument 47046 based on the identification. The surgical hub 27006 may use the serial number to determine one or more capabilities of the medical device (e.g., medical instrument) 47046.

In examples, boundaries of the surgical OR may be determined by camera information sent to the surgical hub. A surgical hub may identify when an object in the surgical OR moved, for example, based on the camera information. For example, the surgical OR may identify that a medical staff member bumped into a surgical robot arm based on camera information that tracked the medical staff member's movement and the surgical robot arm's movement. For example, surgical hub 20006 may use a camera in OR 47000 to determine that HCP 47012 may have come in contact with surgical robot 20032. Surgical hub 20006 may send a notification to HCP 47008 that indicates contact occurred between surgical robot 20032 and HCP 47012.

In examples, the surgical hub may receive information associated with the patient 47058. For example, HCP 47010 may be firing an energy beam on an area of the body of patient 47058 using medical instrument 47048. In such a case, the surgical hub 20006 may overlay the firing location onto display 47038 which may be used by HCP 47010 during the firing of medical instrument. The firing information may be outputted on secondary display, such as display 47032, which may be accessible to the HCP 47016 that may be supporting HCP 47010.

The surgical hub 20006 may identify an indicator on a medical instrument, such as medical instrument 47050. For example, the surgical hub 20006 may use a camera within OR 47000 to identify medical instrument 47050. The surgical hub 20006 may retrieve information associated with the indicator. The indicator may include indexing ports and/or fiducial markers. The indicator may include qualities about medical instrument 47050 such as the length and thickness of the instrument shaft. The surgical hub 20006 may scale the data sent to the medical instrument 47050 based on the qualities. For example, the surgical hub 20006 may determine that medical instrument 47050 may not comprise a fast processor and may reduce amount of data sent to medical device 47050 to prevent the medical device 47050 from becoming less responsive. The cameras that may be used by surgical hub 20006 may identify indexing coordination and/or registration points of the one or more instruments.

The surgical hub 20006 may use a camera to identify a medical instrument based on a characteristic of the medical instrument. For example, surgical hub 20006 may use spatial recognition, via a camera for example, to model the shape of the instrument. In such a case, the camera may identify the instrument based on the shape. For example, surgical hub 20006 may identify medical instrument 47044 as an endo cutter based on an image captured by a camera that includes a shape that resembles an endo cutter.

The surgical hub 20006 may use one or more cameras in the operation room 47000 to generate data based on a display in the operation room 47000. For example, the surgical hub 20006 may use a camera to monitor medical instrument 47046 to determine a setting being displayed on a display that is part of medical instrument 47046. The surgical hub 20006 may read the setting from medical instrument 47046 and may display the setting on display 47038. The surgical hub 20006 may overlay information onto a display. The information may include information from another display. For example, HCP 47008 may request information related to a generator power level, EKG measurements, and instrument firing status. In such a case, the surgical hub 20006 may configure a display associated with medical instrument 47048 such that the display associated with medical instrument 47048 may show the generator power level, the EKG measurement, and the instrument firing status. The instrument may include a display that shows all three of these values. The surgical hub 20006 may port the information to the display that the HCP 47008 may be viewing from a laparoscopic point of view.

The surgical hub 20006 may recognize one or more devices that may not be compatible with each other. For example, surgical hub 20006 may determine that medical instrument 47046 may not be compatible with medical product 47052.

The surgical hub 20006 may take one or more actions to allow one device to be compatible with another device. For example, the surgical hub 20006 may standardize data from medical instrument 47046 such that medical instrument 47050 may be able to exchange data with the medical instrument for 47046.

The surgical hub 20006 may include machine learning that analyzes the metadata as described herein over time. The metadata may be based on camera information sent to the surgical hub 20006. For example, the camera may read information on a display and send the information to the surgical hub 20006 over a duration of time. The surgical hub may input the information into a machine learning model to determine, for example, what an HCP, such as HCP 47010 is doing. The machine learning model may determine suggestions for the HCP 47010 and the HCP 47010 may send the suggestions to the display accessible by the HCP 47010, such as display 47038. The machine learning module may determine when and/or where the surgical hub 20006 may send the information.

The surgical hub 20006 may filter and/or coordinate the data based on what the medical staff needs at a given time. For example, the surgical hub 20006 may comprise data related to the battery level of a harmonic scalpel. The HCP 47008 may be performing a surgical task that does not involve the harmonic scalpel. In such a case, the surgical hub 20006 may filter out the harmonic scalpel data. The surgical hub 20006 may send the filtered data to a display accessible by the surgeon.

Figure 25:
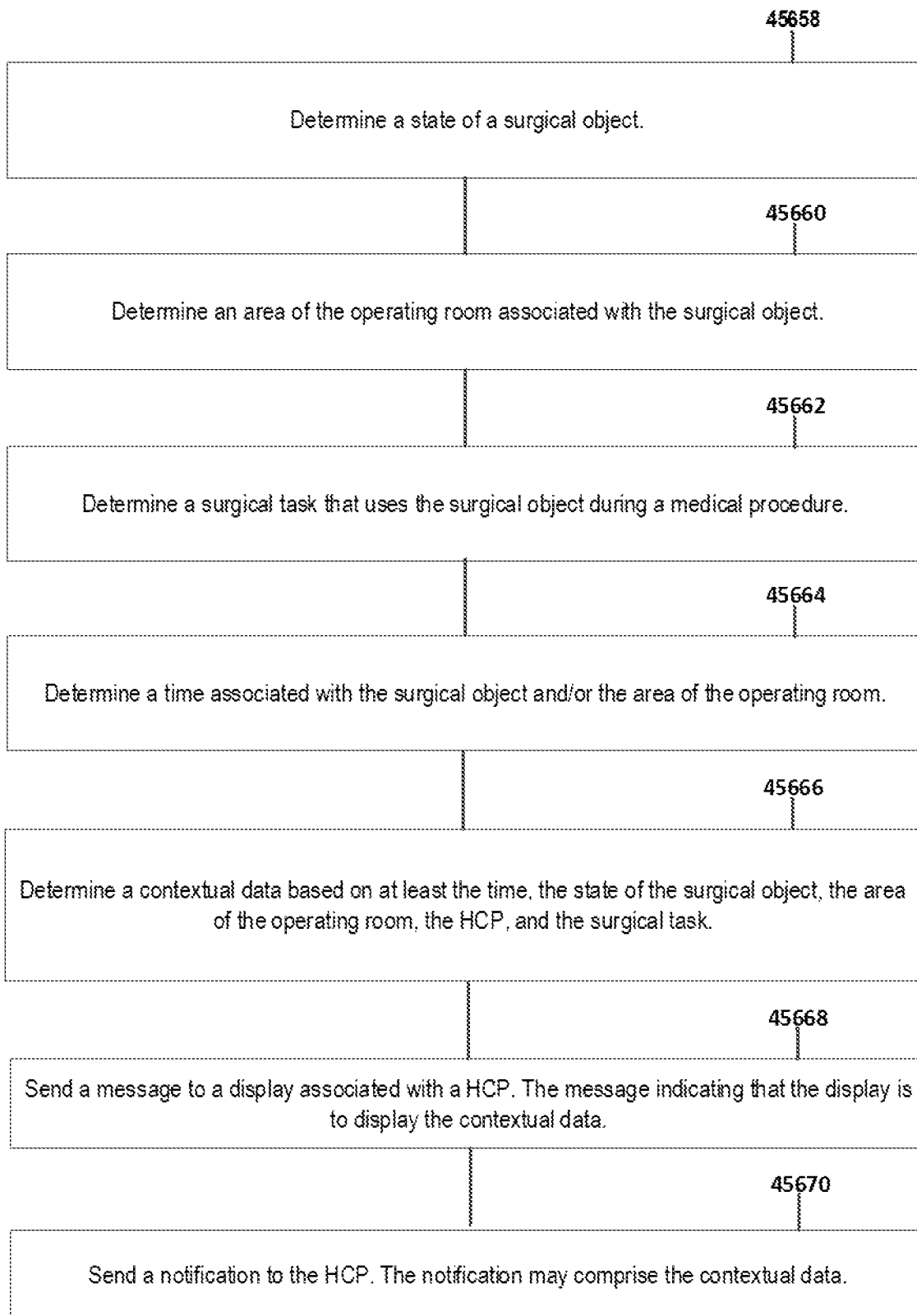

FIG. 25 depicts a method that may be performed by a surgical hub for providing adaptations and/or controls that may change based on spatial awareness of objects and personnel within the surgical OR.

In examples, the surgical hub may determine if an object is inside a patient and may indicate to remove the object. In examples, the surgical hub may track a spatial temporal component associated with each object. For example, the surgical hub may track which device is in a medical staff member's hand, for example, at a given time.

The surgical hub may overlay data on the object. For example, the object may be a medical instrument. A display may be configured for the overlaid data. The display may be included on the medical instrument. The display may be attachable to the medical instrument. The data may be depicted on the screen for a user to see. The cameras as described herein may observe a change in the surgical OR and may overlay data associated with the change to a medical instrument display.

The surgical hub may be aware of secondary objects located in a storage destination. The storage destination may be located outside the surgical OR. The surgical hub may determine when one or more secondary objects are involved in a surgery. In examples, the surgical hub may communicate to a medical staff member (e.g., a rotating nurse) to retrieve the secondary objects involved in the surgery.

The surgical hub may pinpoint each object located in the surgical OR. In examples, the surgical hub may be aware of an instrument involved in a surgery. For example, the instrument may be involved in an upcoming surgical task of the surgery. A display may be accessible to a table nurse and may be in communication with the surgical hub. The surgical hub may indicate the instrument involved in the surgery on the display. For example, the surgical hub may highlight the instrument on the display. The instrument involved in the surgery may be located in a storage destination as described herein. The surgical hub may indicate the storage destination that the instrument is located at.

As shown in FIG. 25, a method may be provided. The method may be performed by a surgical hub for providing adaptations and/or controls that may change based on spatial awareness of objects and personnel within the surgical OR. The method may comprise a number of processes that may be performed in any order. The processes may include 45658, 45660, 45662, 45664, 45666, 45668, and/or 45670.

At 45658, the state of a surgical object may be determined. For example, a surgical hub may detect a surgical object and may determine the state of the surgical object. The surgical object may be a medical instrument, a common surgical instrument, a surgical product, a medical product, a medical equipment, an object in the operation room, and/or the like.

The state of a surgical object may indicate that the surgical product may be new, may be unopen, may be opened, may be used, may need to be discarded, and the like, or any combination thereof. The state of the surgical object may indicate that the surgical instrument may be ready to be used, that the surgical instrument may need to be cleaned, that the surgical instrument may not be ready, that the surgical instrument is being used, and/or the like.

At 45660, an area of the operating room may be determined. The area of the operating room may be associated with the surgical object. The area of the operating room may be associated with a medical instrument and/or a medical equipment. The area of the operating room may be a storage area, a shelf, a surgical table, an area associated with HCP, an area associated with the patient, a Mayo cart, a surgical back table, an area for preparation of medical instruments, an area for cleaning medical instruments, a sterile field, a non-sterile field, and/or the like.

In an example, a surgical hub may determine that a Mayo cart may be present in the operating room. The surgical hub may determine that one or more medical instruments may be present on the Mayo cart. The surgical hub may determine that one or more HCPs may be near the Mayo cart.

In an example, the surgical hub may determine that a portion of the operating room may be a sterile field. The sterile field may be an area that is sterile. The surgical hub may determine that one or more objects within the sterile field are sterile. The surgical hub may determine that a medical instrument may pass from a non-sterile field to the sterile field and may determine that the medical instrument may have been cleaned and may be sterile, and that the medical instrument may be allowed in the sterile field. The surgical hub may determine that a medical instrument may not be allowed to pass from a non-sterile field to a sterile field. The medical hub may determine that the non-sterile medical instrument may have entered into the sterile field. The medical hub may notify one or more HCP's that the non-sterile medical instrument may be in the sterile field and the medical hub may indicate that an individual that may have contacted the non-sterile medical instrument may also be non-sterile.

In an example, the surgical hub may determine that a portion of the operating room may be associated with the floor of the operating room. The surgical hub may monitor the floor of the operating room to determine if an object may come in contact with the floor. For example, the surgical hub may identify a medical instrument that may have been dropped by an HCP onto the floor. The surgical hub may notify one or more HCPs that the medical instrument may be on the floor and may not be sterile. The surgical hub may indicate to an HCP to retrieve the medical instrument on the floor and may provide instructions to the HCPs on how to clean the medical instrument.

In an example, the surgical hub may have determined that a portion of the operating room may be associated with a storage area. The surgical hub may monitor the storage area. The surgical hub may determine that one or more medical instruments and/or medical products may be located within the storage area. The surgical hub may keep an inventory of the one or more medical instruments and/or medical products that may be located within the storage area. For example, the surgical hub may remove a medical instrument from the inventory when the HCP retrieves the medical instrument from the storage area.

The surgical hub may determine an area of the operating room in any one of the ways described herein. For example, the surgical hub may use an ultrasonic ping to determine one or more areas of the operating room. As another example, the surgical hub may use laser radar (lidar). The surgical hub may use electrical signals, Wi-Fi signals, wireless signals, the determination of signal strength, a determination of distances between devices, ultrasonic measurements, sensors, indicators, RFID's, and/or the like to determine one or more areas of the operating room. The surgical hub may use one or more cameras to determine areas of the operating room. For example, the surgical hub may analyze video and/or images retrieved from a camera to determine one or more areas of the operating room.

The surgical hub may determine a surgical object and may determine an area associated with the surgical object. For example, the surgical hub may use one or more sensors and/or one or more cameras to determine a surgical object, such as a medical instrument. In an example, the surgical hub may use a camera to identify a Mayo cart and may identify one or more medical instruments on the Mayo cart. In an example, the surgical hub may identify an area of the operating room that may be occupied by an HCP and may identify a medical instrument that may be held by the HCP.

The surgical hub may identify one or more objects that may be on, near, and/or in a patient. For example, the surgical hub may identify a medical instrument that may be used to perform a procedure on a patient. The surgical hub may identify that the medical instrument may have contacted the patient. The surgical hub may identify that the medical instrument may be inserted into the patient. The surgical hub may track that the medical instrument may be in the patient and may notify an HCP if the medical instrument may be left inside the patient. The surgical hub may identify a medical product that may be applied on the patient. The surgical hub may identify a medical device that may be placed inside the patient.

At 45662, a surgical task that may use the surgical object may be determined. For example, a surgical task that may use the surgical object during a medical procedure may be determined. In an example, the surgical hub may determine a surgical procedure and may determine one or more surgical tasks that may be associated with the surgical procedure. The surgical task may indicate that an HCP is to use a medical instrument to perform a task on a patient. For example, the surgical task may indicate that an HCP is to use a medical stapler to staple the patient's tissue together during a surgery. In an example, the surgical task may indicate that an HCP is to clean a medical instrument before the medical instrument may be used on a patient. In an example, the surgical task may indicate one or more instructions for an HCP to clean the medical instrument and/or prepare the medical instrument to be used.

At 45664, a time associated with the surgical object and/or the area of the operating room may be determined. For example, the time may be associated with a surgical object, such as a medical instrument and/or a medical product. The time may indicate when a medical instrument may have entered the operating room, may have been cleaned, may have been made sterile, may have been used, may have been made non sterile, may have come in contact with a patient, may have come in contact with an HCP, may have left the operating room, may have entered a patient, may have left the patient, and/or the like. The time may indicate when a medical product may have been used, may have been opened, how long the medical product has been opened, when the medical product entered the operating room, when the medical product came into contact with a patient, when the medical product may have been made sterile, when the medical product was sterile, when the medical product may not have been sterile, when the medical product became non sterile, when the medical product may have been placed inside the patient, when the medical product may have been removed from a patient, when the medical product may have come in contact with an HCP, and/or the like.

The time may be associated with an area of the operating room. For example, the time may indicate when an HCP may have entered the operating room, may have entered an area of the operating room, may have left an area of the operating room, may have exited the operating room, and/or the like. The time may indicate when a patient may have entered the operating room, may have entered an area of the operating room, may have left an area of the operating room, may have exited the operating room, and/or the like.

At 45666, contextual data may be determined. The contextual data may be based on the time, the state of the surgical object, the area of the operating room, the HCP, the surgical task, and/or the like. The contextual data may be any contextual data described herein. For example, the contextual data may indicate that a medical instrument may have come in contact with an HCP in an area of the operating room and may indicate one or more settings of the medical instrument. In an example, the contextual data may indicate one or more vital signs of a patient that may be located in an area of the operating room.

At 45668, a message may be sent to a display associated with an HCP. In an example, the display may be determined and the message may be sent to the determined display. The message may indicate that the display is to display the contextual data. The contextual data may be any contextual data described herein.

At 45670, a notification may be sent to an HCP. The notification may comprise the contextual data. A notification may be sent to an HCP to provide the HCP with instructions on how to use a medical instrument. The notification may be sent to an HCP to provide the HCP with an indication as to what settings may be applied to a medical instrument and/or what settings have been applied to a medical instrument. The notification may be sent to an HCP to provide the HCP with the contextual data, such as a vital sign of a patient and/or a suggested setting for a medical instrument.

Systems, methods, and/or instrumentalities for a surgical hub providing a health care provider (HCP) with a data overlay may be provided. A state of a surgical object and/or an area of the operating room where the surgical object is located may be determined. Determining an area of the operating room where the surgical object is located may comprise using a sensor data associated with the area, a wearable device data, sensor data associated with the HCP, an image from a camera within the operating room, an ultrasonic sensor, a laser sensor, a laser doppler sensor, a radio frequency sensor, and/or a video from the camera within the operating room. A time associated with the surgical object and/or the area of the operating room may be determined. The state of the surgical object may be determined to indicate that the surgical object is ready for use in the surgical task.

A surgical task that uses the surgical object during a medical procedure may be determined. The surgical object entering the area of the operating room during the task and/or medical procedure may be determined. In examples, determining that the surgical object has entered the operating room may be based on the area of the operating room where the surgical object is located. The time may indicate when the surgical object entered the operating room. In examples, it may be determined that the surgical object has left the area of the operating room. The time may indicate when the surgical object has left the area.

In examples, contextual data may be determined based on the state of the object, the area of the operating room, and/or the surgical task. In examples, the contextual data may be determined based on the time associated with the surgical object and/or the area of the operating room. In examples, the state of the surgical object may be determined to indicate that the surgical object has not been prepared for use in the surgical task. For example, the contextual data may comprise one or more instructions for preparing the surgical object in the surgical task. It may be determined that the surgical object has not been retained in a patient. For example, the contextual data may comprise an indication that the surgical object has not been retained in the patient. The contextual data may comprise an indication that the surgical object has been used. For example, the contextual data may comprise an instruction for cleaning the surgical object and/or an instruction for disposing of the surgical object. In examples, the surgical object may comprise a package. The package may be determined to have been opened in the area at the time. In examples, the area of the operating room may be a stock area, a mayo stand, a surgical site, a sterile field, and/or a non-sterile field.

A message may be sent to a display associated with the HCP. In examples, the message may indicate that the display is to display the contextual data. The message may be sent to a database. The message may indicate that the package has been opened. The message may comprise the contextual data. The message may indicate that the surgical object is to be removed from an inventory. In examples, it may be determined that the display is within a distance of the location of the HCP. In examples, the display may include a wearable display, a tablet, an augmented reality device, and/or a smart phone. A notification may be sent to the HCP. For example, the notification may comprise the contextual data.

In examples, a surgical instrument that is to be used to perform a surgical task during a medical procedure may be determined. An area of the operating room associated with the surgical instrument may be determined. The area of the operating room may be a stock area. The message sent to the display may comprise a notification to the HCP that guides the HCP to the surgical instrument in the stock area. An orientation of the surgical instrument may be determined. In examples, a display associated with the HCP may be determined. Contextual data may be determined based on the surgical task, the area of the surgical room, and/or the orientation of the surgical instrument. The contextual data may comprise an image and/or a status of the instrument. The message sent to the display may indicate the image and/or the status of the instrument to be overlaid on a display data being shown on the display.

The surgical instrument may comprise a fiducial marker. For example, it may be determined that the surgical instrument is using the fiducial marker. It may be determined that contextual data may comprise an orientation of the surgical instrument that may be improved. For example, the contextual data may comprise an instruction to the HCP to improve the orientation of the surgical instrument. The capability of the display associated with the HCP may be determined. For example, the contextual data may be modified based on the capability of the display.

Figure 26:
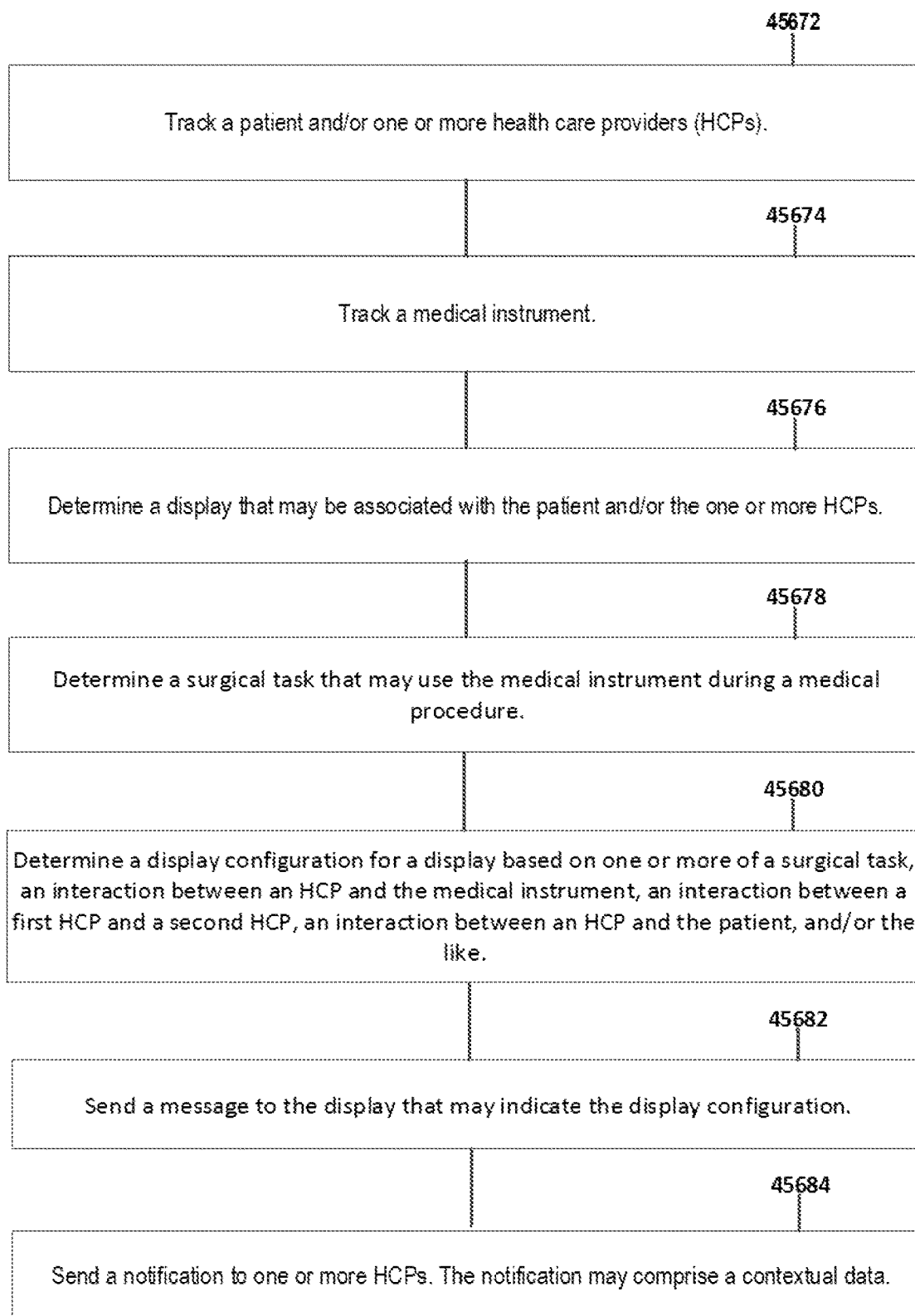
FIG. 26 depicts a method that may be performed by a surgical hub for providing adaptive control, operation of display, and/or display interactions that may be based on recognition of users, equipment, and/or usage and user or equipment needs.

FIG. 26 depicts a method that may be performed by a surgical hub for providing adaptive control, operation of display, and/or display interactions that may be based on recognition of users, equipment, and/or usage and user or equipment needs.

The surgical hub may be aware of an indicator on each medical instrument. The camera may identify the indicator and send the indicator to the surgical hub along with the medical instrument's location (e.g., via coordinate points). In examples, the indicator may include indexing points and/or fiducial markers. The indicator may include qualities about the instrument such as the length and thickness of the instrument shaft. The surgical hub may scale the data sent to the instrument based on the qualities. The cameras may identify indexing coordination and/or registration points of the one or more instruments.

In examples, the camera may identify the instruments based on the characteristics of the instrument. For example, the camera may use spatial recognition to model the shape of the instrument. In such a case, the camera may identify the instrument based on the shape. For example, the camera may identify a handle resembling an endo cutter handle and may determine that the instrument is an endo cutter.

The camera may generate data based on a display in the surgical OR. The camera may overlay information onto the display. The information may include information from another display. For example, a surgeon may request information related to a generator power level, EKG measurements, and instrument firing status. In such a case, the instrument may include a display that shows all three of these values. A surgical hub may port the information to the display the surgeon looks at from a laparoscopic point of view.

The surgical hub may identify and/or recognize that one or more devices are not compatible with each other. The surgical hub may standardize the data into a form to allow data to be exchanged between the devices.

The surgical hub may include machine learning that analyzes the metadata as described herein over time. The metadata may be based on camera information sent to the surgical hub. For example, the camera may read information on a display and send the information to the surgical hub over a duration of time. The surgical hub may input the information into a machine learning model to determine, for example, what the surgeon is doing. The machine learning model may determine suggestions for the surgeon and may send the suggestions to the display accessible by the surgeon. The machine learning module may determine when and/or where the surgical hub should send the information. For example, the machine learning model may tell the surgical hub to send information related to ligating the IMA when the surgeon performs mobilization.

As shown in FIG. 26, a method may be provided. The method may be performed by a surgical hub for providing adaptations and/or controls that may change based one or more interactions, a recognition of users, recognition of equipment, usage, a user request, an equipment request, and/or the like. The one or more interactions may include a display interaction, an interaction with a patient, an interaction with an HCP, an interaction between one or more HCPs, an interaction between an HCP and the patient, and/or the like. The method may comprise a number of processes that may be performed in any order. The processes may include 45672, 45674, 45676, 45678, 45680, 45682, and/or 45684.

At 45672, a patient and/or one or more HCPs may be tracked. For example, a surgical hub may track a patient, a first HCP, and a second HCP. The patient, the first HCP, and the second HCP may be located within an operating room. The surgical hub may track the patient, the first HCP, and the second HCP using any of the methods described herein. For example, the surgical hub may track the patient using a camera, a RFID, an ultrasonic device, a tracking device, a sensor, and/or the like. In an example, the surgical hub may track the first HCP using a device that may be associated with the HCP, such as a smart watch.

At 45674, a medical object, which may be a medical instrument and/or a medical product, may be tracked. For example, the surgical hub may track a medical instrument that may be located within the operating room. As another example, the surgical hub may track a medical instrument that may not be located within the operating room. The surgical hub may notify a user, such as an HCP, of the location of the medical product, such as the medical instrument. For example, the surgical hub may notify a user that the medical instrument may be located within the operating room, such as an area that indicates a Mayo cart, and may indicate a status of the medical instrument, such as that the medical instrument may need to be cleaned in order to be used.

At 45676, a display that may be associated with the patient and/or the one or more HCP's may be determined. For example, the surgical hub may determine that an HCP is near a display. The surgical hub may determine the identity of the display and may send data to be viewed by the HCP to the display associated with the HCP. In an example, the surgical hub may determine that the patient may be near a display that is likely to be viewed by an HCP. The surgical hub may determine data that may be sent to the display that may be near the patient such that an HCP may be able to view the data.

At 45678, a surgical task that may use a medical object during a medical procedure may be determined. The medical object may be a medical instrument and/or a medical product. The surgical task may be a task that may be part of the medical procedure that may be performed by an HCP. For example, the task may indicate that a surgeon may use a stapler on the patient. In an example, the task may indicate that a nurse may need to clean a medical instrument before the medical instrument may be provided to a surgeon. In an example, the task may indicate that a medical instrument may need to be retrieved from an area outside the operating room by a first HCP, that the medical instrument may need to be provided to a second HCP that may prepare and clean the medical instrument, and that a third HCP may use the medical instrument to perform the medical procedure on the patient.

At 45680, a display configuration for a display may be determined. For example, the display configuration for the display may be determined based on one or more of a surgical task, an interaction between an HCP and the medical object, an interaction between a first HCP and a second HCP, an interaction between an HCP and the patient, an interaction between the patient and a medical object, and/or the like. A medical object may be a medical instrument, a medical product, a surgical instrument, a surgical product, a medical equipment, and/or the like.

The configuration may be customized for an HCP. For example, the surgical hub may have determined that the surgical task may require the HCP to use the medical instrument on the patient. The surgical hub may determine that the medical instrument may comprise one or more settings. The surgical hub may determine that the HCP may prefer to view a portion of the one or more settings. The surgical hub may determine that the HCP may have one or more preferred settings for the medical instrument. The surgical hub may determine a configuration for the display such that the display may display the HCP's preferred settings for the medical instrument and the surgical hub may configure the medical instrument according to the HCP preferred settings.

The surgical hub may determine one or more settings based on an analysis of patient outcome. For example, the surgical hub may analyze the history of surgeries performed and may determine that display settings and/or medical instrument settings may result in improved outcomes. The surgical hub may use these display settings and/or medical instrument settings to determine the display configuration and may provide that display configuration to a display and/or a medical instrument.

At 45682, a message may be sent to a display that may indicate the display configuration. The message may include an indication and/or instruction for the display. For example, the message may indicate that the display is to display data according to the display configuration. In an example, the message may indicate that the display is to display data that may be included in the display configuration. In an example, the message may indicate that the display is to coordinate with another device, such as another display or a medical instrument, in accordance with the display configuration.

In an example, the message may be sent to an augmented reality display. For example, an HCP may be wearing safety glasses that may include a device that is able to provide an augmented display to the HCP. The message may indicate to the augmented safety glasses that data may be overlaid on the view that the HCP is viewing. For example, the HCP may be viewing the patient through the safety glasses and the safety glasses may overlay vital signs for the patient on or near the patient. In an example, the HCP may be viewing the patient through the safety glasses and the safety glasses may overlay a medical image of the patient on or over the patient.

At 45684, a notification may be sent to one or more HCP's. The notification may comprise contextual data. The contextual data may be the contextual data described herein. For example, the contextual data may include data that may be associated with the surgical task, the patient, a setting for the medical instrument, a vital sign for the patient, a medical image, and/or the like. The notification may be sent to the HCP via a display, a speaker, an email, a message, and/or the like. For example, the notification may be sent to a smartwatch that may be worn by the HCP. In an example, the notification may be sent to a speaker such that the HCP may be able to listen to a voice that speaks the data to the HCP.

Systems, methods, and/or instrumentalities for a surgical hub configuring a display may be provided. In examples, a health care provider (HCP) and/or a medical instrument may be tracked within an operating room. In examples, a first HCP and a second HCP may be tracked within an operating room. In examples, an HCP and/or a patient may be tracked within an operating room. A surgical task that uses the medical instrument during a medical procedure may be determined.

A display configuration for the display may be determined, for example, based on the surgical task and/or an interaction between the HCP and the medical instrument. In examples, a first display configuration may be determined based on a first interaction between the HCP and the medical instrument. For example, a second interaction may be determined between the HCP and the medical instrument, the HCP and the display, and/or the HCP and the patient. The display configuration may be modified based on the second interaction. The display configuration for the display may be determined based on the surgical task and an interaction between a first HCP and a second HCP. For example, the interaction between the first HCP and the second HCP may be a verbal communication. The verbal communication may be determined to be a request from the first HCP for assistance from the second HCP in performing the surgical task. The display configuration may be modified such that the display configuration may configure the display with one or more preferences that are relevant to the second HCP.

In examples, a third HCP that is able to assist in performing the surgical task may be determined. The third HCP may be outside the operating room. In examples, the interaction between the HCP and the patient may be determined to indicate that the surgical task is being performed. A notification may be sent to the third HCP. For example, the notification may indicate that the third HCP has been requested to assist in the operating room with the surgical task. In examples, determining the interaction between the first HCP and the second HCP may comprise the first HCP providing the medical instrument to the second HCP. For example, the display may include an augmented reality display, a personal display, a display associated with a surgical interface table, an equipment display, a medical instrument display, a room monitor, a primary monitor, and/or a secondary monitor. In examples, the display configuration may comprise contextual data, medical instrument data, patent data, an instruction associated with the surgical task, a notification for the HCP regarding the patient, a notification for the HCP regarding the medical instrument, a notification for the HCP regarding the surgical task, and/or a status of the medical instrument. The display configuration may comprise one more preferences for the second HCP.

In examples, the orientation of the display in relation to the HCP may be determined. For example, the orientation may comprise a position of the display in relation to the HCP, a direction of the display in relation to the HCP, and/or a distance between the display and the HCP. A position and/or orientation of the HCP may be determined. The display configuration may be modified, for example, based on the orientation and/or position of the HCP. In examples, a message may be sent to the display. The message may comprise the display configuration. The message to the display may comprise an instruction associated with the surgical task, patient data, a status of the medical instrument, and/or a parameter associated with the medical instrument. In examples, a first message may be sent to a first display. For example, it may be determined that an HCP has viewed a second display. Displayed data being displayed on the second display may be determined. A second message may be sent to the first display. For example, the second message may instruct the first display to display the displayed data.

A location of the operating room where the display is positioned may be determined. A direction between the display and the HCP may be determined. In examples, the display configuration may be modified based on the location of the operating room and/or the direction between the display and the HCP. In examples, a capability of the display may be determined using a camera within the operating room. The display configuration may be modified based on the capability of the display.

In examples, patient data associated with the surgical task may be determined. The display configuration may be modified based on the patient data. A voice command provided by the HCP may be received. For example, the voice command may indicate that a setting of the display is to be changed. The display configuration may be modified, for example, based on the voice command.

The invention claimed is:

1. A surgical hub for configuring a display, the surgical hub comprising:
 a processor, the processor configured to:
  track a health care provider (HCP) and a medical instrument within an operating room;
  determine a surgical task that uses the medical instrument during a medical procedure;
  determine an interaction between the HCP and the medical instrument, wherein the interaction comprises a verbal communication indicating a request for assistance in performing the surgical task;
  based on the surgical task and the interaction between the HCP and the medical instrument, determine a display configuration for the display; and
  send a message to the display, wherein the message comprises the display configuration.

2. The surgical hub of claim 1, wherein the display is at least one of an augmented reality display, a personal display, a display associated with a surgical interface table, an equipment display, a medical instrument display, a room monitor, a primary monitor, or a secondary monitor.

3. The surgical hub of claim 1, wherein the display configuration further comprises at least one of contextual data, medical instrument data, patent data, an instruction associated with the surgical task, a notification for the HCP regarding a patient, a notification for the HCP regarding the medical instrument, a notification for the HCP regarding the surgical task, or a status of the medical instrument.

4. The surgical hub of claim 1, wherein the processor is further configured to:
 determine an orientation of the display in relation to the HCP, the orientation comprising at least one of a position of the display in relation to the HCP, a direction of the display in relation to the HCP, or a distance between the display and the HCP.

5. The surgical hub of claim 1, wherein the processor is further configured to:
 determine a location of the operating room where the display is positioned;
 determine a direction between the display and the HCP; and
 modify the display configuration based on the location of the operating room and the direction between the display and the HCP.

6. The surgical hub of claim 1, wherein the interaction is a first interaction, and wherein the processor is further configured to:
 determine a second interaction between at least one of the HCP and the medical instrument, the HCP and the display, or the HCP and a patient; and
 modify the display configuration based on the second interaction.

7. The surgical hub of claim 1, wherein the processor is further configured to:
 determine a capability of the display using a camera within the operating room; and
 modify the display configuration based on the capability of the display.

8. A surgical hub for configurating a display, the surgical hub comprising:
 a processor, the processor configured to:
  track a first health care provider (HCP), a second HCP, and a medical instrument within an operating room;
  determine a surgical task to be performed by the first HCP during a medical procedure;
  based on the first HCP, the second HCP, and the medical instrument, determine an interaction between the first HCP and the second HCP, wherein the interaction comprises the first HCP providing the medical instrument to the second HCP;
  based on the surgical task and the interaction between the first HCP and the second HCP, determine a display configuration for the display; and
  send a message to the display, wherein the message comprises the display configuration.

9. The surgical hub of claim 8, wherein the interaction between the first HCP and the second HCP further comprises a verbal communication, and wherein the processor is further configured to:
 determine that the verbal communication is a request from the first HCP for assistance from the second HCP in performing the surgical task; and
 modify the display configuration such that the display configuration configures the display with one or more preferences that are relevant to the second HCP.

10. The surgical hub of claim 8, wherein the interaction between the first HCP and the second HCP further comprises a verbal communication, and wherein the processor is further configured to:
 determine that the verbal communication is a request for assistance in performing the surgical task;
 based on the determination that the verbal communication is the request for assistance in performing the surgical task, determine that a third HCP is able to assist in performing the surgical task, wherein the third HCP is outside the operating room; and
 based on the determination that the third HCP is able to assist in performing the surgical task, send a notification to the third HCP, wherein the notification indicates that the third HCP has been requested to assist in the operating room with the surgical task.

11. The surgical hub of claim 8, wherein the display configuration comprises one or more preferences for the second HCP.

12. The surgical hub of claim 8, wherein the interaction is a first interaction, and wherein the processor is further configured to:
 track a patient;
 determine a second interaction between the second HCP and the patient; and
 modify the display configuration for the display based on the second interaction.

13. The surgical hub of claim 12, wherein the message to the display further comprises at least one of an instruction associated with the surgical task, patient data, a status of the medical instrument, or a parameter associated with the medical instrument.

14. A surgical hub for configuring a display, the surgical hub comprising:
 a processor, the processor configured to:
  track a health care provider (HCP) and a patient within an operating room;
  determine an interaction between the HCP and the patient;
  determine a surgical task to be performed during a medical procedure;
  based on the interaction between the HCP and the patient, determine a display associated with the HCP;
  determine a display configuration for the display based on the surgical task and the interaction between the HCP and the patient; and
  send a message to the display, the message comprising the display configuration.

15. The surgical hub of claim 14, wherein the processor is further configured to determine that the interaction between the HCP and the patient indicates that the surgical task is being performed.

16. The surgical hub of claim 14, wherein the processor is further configured to:
  determine patient data associated with the surgical task; and
  modify the display configuration based on the patient data.

17. The surgical hub of claim 14, wherein the processor is further configured to:
  receive a voice command provided by the HCP, the voice command indicating that a setting of the display is to be changed; and
  modify the display configuration based on the voice command.

18. The surgical hub of claim 14, wherein the processor is further configured to:
  determine an orientation of the HCP and a position of the HCP; and
  modify the display configuration based on the orientation of the HCP and the position of the HCP.

19. The surgical hub of claim 14, wherein the message is a first message, wherein the display is a first display, and wherein the processor is further configured to:
  determine that the HCP has viewed a second display;
  determine displayed data that is being displayed on the second display; and
  send a second message to the first display, the second message instructing the first display to display the displayed data.

20. The surgical hub of claim 14, wherein the HCP is a first HCP, wherein the interaction is a first interaction, and wherein the processor is further configured to:
  track a second HCP in the operating room;
  based on the first HCP, determine a first position of the first HCP relative to the patient;
  based on the second HCP, determine a second position of the second HCP relative to the patient;
  determine a second interaction between the second HCP and the patient;
  based on the first position, the second position, the first interaction, and the second interaction, determine that the second HCP is to perform the surgical task during the medical procedure; and
  modify the display configuration such that the display configuration configures the display with one or more preferences that are relevant to the second HCP.

* * * * *